United States Patent
Ohashi et al.

(10) Patent No.: US 8,691,490 B2
(45) Date of Patent: Apr. 8, 2014

(54) SULFONIUM SALT, POLYMER, METHOD FOR PRODUCING THE POLYMER, RESIST COMPOSITION AND PATTERNING PROCESS

(75) Inventors: Masaki Ohashi, Jyoetsu (JP); Satoshi Watanabe, Jyoetsu (JP); Youichi Ohsawa, Jyoetsu (JP); Keiichi Masunaga, Jyoetsu (JP); Takeshi Kinsho, Jyoetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 210 days.

(21) Appl. No.: 13/013,506

(22) Filed: Jan. 25, 2011

(65) Prior Publication Data
US 2011/0189607 A1    Aug. 4, 2011

(30) Foreign Application Priority Data
Feb. 2, 2010   (JP) .................. 2010-021078

(51) Int. Cl.
G03F 7/004   (2006.01)
C07C 69/54   (2006.01)
C07C 309/67  (2006.01)

(52) U.S. Cl.
USPC ........ 430/270.1; 430/921; 430/925; 560/219; 560/221; 560/222; 560/223; 562/109; 562/110; 562/113

(58) Field of Classification Search
None
See application file for complete search history.

(56) References Cited

U.S. PATENT DOCUMENTS

| | | | |
|---|---|---|---|
| 5,650,483 A | 7/1997 | Malik et al. |
| 5,945,250 A | 8/1999 | Aoai et al. |
| 6,048,672 A | 4/2000 | Cameron et al. |
| 6,280,898 B1 | 8/2001 | Hasegawa et al. |
| 6,312,867 B1 | 11/2001 | Kinsho et al. |
| 7,833,694 B2 | 11/2010 | Hasegawa et al. |
| 8,062,831 B2 | 11/2011 | Shinachi et al. |
| 2002/0102491 A1 | 8/2002 | Kodama et al. |
| 2003/0013039 A1 | 1/2003 | Kobayashi et al. |
| 2004/0197697 A1 | 10/2004 | Korionoff et al. |
| 2004/0260031 A1 | 12/2004 | Takeda et al. |
| 2006/0228648 A1 | 10/2006 | Ohsawa et al. |
| 2007/0078269 A1 | 4/2007 | Harada et al. |
| 2007/0148594 A1 | 6/2007 | Funatsu et al. |
| 2007/0149702 A1 | 6/2007 | Ando et al. |
| 2007/0160929 A1 | 7/2007 | Hasegawa et al. |
| 2007/0231738 A1 | 10/2007 | Kaneko et al. |
| 2007/0264596 A1 | 11/2007 | Ohsawa et al. |
| 2008/0026331 A1 | 1/2008 | Hasegawa et al. |
| 2008/0085469 A1 | 4/2008 | Ohsawa et al. |
| 2008/0090172 A1 | 4/2008 | Hatakeyama et al. |
| 2008/0096128 A1 | 4/2008 | Takeda et al. |
| 2008/0102407 A1 | 5/2008 | Ohsawa et al. |
| 2008/0118860 A1 | 5/2008 | Harada et al. |
| 2008/0153030 A1 | 6/2008 | Kobayashi et al. |
| 2008/0305411 A1 | 12/2008 | Koitabashi et al. |
| 2009/0069521 A1 | 3/2009 | Nagai et al. |
| 2009/0081588 A1 | 3/2009 | Hatakeyama et al. |
| 2009/0208867 A1 | 8/2009 | Harada et al. |
| 2009/0208873 A1 | 8/2009 | Harada et al. |
| 2009/0233223 A1 | 9/2009 | Tachibana et al. |
| 2009/0233242 A1 | 9/2009 | Hasegawa et al. |
| 2009/0274978 A1 | 11/2009 | Ohashi et al. |
| 2009/0274984 A1 | 11/2009 | Shinachi et al. |
| 2009/0280434 A1 | 11/2009 | Harada et al. |
| 2009/0318652 A1 | 12/2009 | Nagai et al. |
| 2010/0075256 A1 | 3/2010 | Joo et al. |
| 2010/0099042 A1 | 4/2010 | Ohashi et al. |
| 2010/0112482 A1 | 5/2010 | Watanabe et al. |
| 2010/0136478 A1 | 6/2010 | Kawaue et al. |

(Continued)

FOREIGN PATENT DOCUMENTS

| | | |
|---|---|---|
| CA | 2049772 A1 | 2/1992 |
| JP | A-03-501970 | 5/1991 |

(Continued)

OTHER PUBLICATIONS

Jul. 17, 2012 Notification of Reasons for Refusal issued in Japanese Application No. 2010-021078 (with partial translation).

(Continued)

*Primary Examiner* — Sin J. Lee
(74) *Attorney, Agent, or Firm* — Oliff PLC

(57) ABSTRACT

There is disclosed a sulfonium salt represented by the following general formula (1). In the formula, X and Y each represents a group having a polymerizable functional group; Z represents a divalent hydrocarbon group having 1 to 33 carbon atoms optionally containing a hetero atom; $R^1$ represents a divalent hydrocarbon group having 1 to 36 carbon atoms optionally containing a hetero atom; and $R^2$ and $R^3$ each represents a monovalent hydrocarbon group having 1 to 30 carbon atoms optionally containing a hetero atom or $R^2$ and $R^3$ may be bonded with each other to form a ring together with a sulfur atom in the formula. There can be provided a sulfonium salt usable as a resist composition providing high resolution and excellent in LER in photolithography using a high energy beam such as an ArF excimer laser, an EUV light and an electron beam as a light source, a polymer obtained from the sulfonium salt, a resist composition containing the polymer and a patterning process using the resist composition.

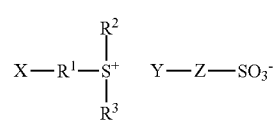

(1)

2 Claims, 4 Drawing Sheets

(56) References Cited

U.S. PATENT DOCUMENTS

| | | | |
|---|---|---|---|
| 2010/0136482 A1 | 6/2010 | Harada et al. | |
| 2010/0143830 A1 | 6/2010 | Ohashi et al. | |
| 2010/0159392 A1* | 6/2010 | Hatakeyama et al. | 430/286.1 |
| 2010/0248149 A1 | 9/2010 | Tsuchimura et al. | |
| 2010/0297560 A1 | 11/2010 | Seshimo et al. | |
| 2010/0304294 A1 | 12/2010 | Ichikawa et al. | |
| 2011/0014566 A1 | 1/2011 | Ichikawa et al. | |
| 2011/0189607 A1 | 8/2011 | Ohashi et al. | |
| 2012/0065291 A1 | 3/2012 | Matsumura et al. | |
| 2012/0308920 A1 | 12/2012 | Domon et al. | |
| 2012/0308932 A1 | 12/2012 | Sagehashi et al. | |

FOREIGN PATENT DOCUMENTS

| | | |
|---|---|---|
| JP | A-4-230645 | 8/1992 |
| JP | A-11-282168 | 10/1999 |
| JP | A-2000-159758 | 6/2000 |
| JP | A-2000-336121 | 12/2000 |
| JP | A-2002-214774 | 7/2002 |
| JP | A-2003-66612 | 3/2003 |
| JP | A-2004-2252 | 1/2004 |
| JP | A-2004-115630 | 4/2004 |
| JP | A-2004-531749 | 10/2004 |
| JP | B2-3613491 | 11/2004 |
| JP | A-2005-8766 | 1/2005 |
| JP | A-2005-84365 | 3/2005 |
| JP | A-2006-178317 | 7/2006 |
| JP | A-2006-306856 | 11/2006 |
| JP | A-2007-145797 | 6/2007 |
| JP | A-2007-197718 | 8/2007 |
| JP | A-2007-297590 | 11/2007 |
| JP | A-2007-304490 | 11/2007 |
| JP | A-2008-31298 | 2/2008 |
| JP | A-2008-80474 | 4/2008 |
| JP | A-2008-106045 | 5/2008 |
| JP | A-2008-111103 | 5/2008 |
| JP | A-2008-122932 | 5/2008 |
| JP | A-2008-133448 | 6/2008 |
| JP | A-2008-158339 | 7/2008 |
| JP | A-2009-7323 | 1/2009 |
| JP | A-2009-98638 | 5/2009 |
| JP | A-2009-191151 | 8/2009 |
| JP | A-2009-192784 | 8/2009 |
| JP | A-2009-242789 | 10/2009 |
| JP | A-2009-269953 | 11/2009 |
| JP | A-2009-276363 | 11/2009 |
| JP | A-2010-002599 | 1/2010 |
| JP | A-2010-107695 | 5/2010 |
| JP | A-2010-134012 | 6/2010 |
| JP | A-2010-155824 | 7/2010 |
| JP | B2-4539865 | 7/2010 |
| JP | A-2010-250290 | 11/2010 |
| JP | A-2010-271501 | 12/2010 |
| JP | A-2011-006398 | 1/2011 |
| JP | A-2011-026300 | 2/2011 |
| JP | A-2011-37834 | 2/2011 |
| JP | A-2011-037836 | 2/2011 |
| JP | A-2011-085878 | 4/2011 |
| WO | WO 89/03389 A1 | 4/1989 |
| WO | WO 2007/069640 A1 | 6/2007 |
| WO | WO 2010/119910 A1 | 10/2010 |

OTHER PUBLICATIONS

Devoe et al., "Photochemistry and Photophysics of 'Onium Salts*," *Advances in Photochemistry*, vol. 17, pp. 313-355, 1992, John Wiley & Sons.

Dammel et al., "193 nm Immersion Lithography—Taking the Plunge," *Journal of Photopolymer Science and Technology*, vol. 17, No. 4, pp. 587-602, 2004.

Arimitsu et al., "Sensitivity Enhancement of Chemical-Ampflication-Type Photoimaging Materials by Acetoacetic Acid Derivatives," *Journal of Photopolymer Science and Technology*, vol. 8, No. 1, pp. 43-46, 1995.

Arimitsu et al., "Effect of Phenolic Hydroxyl Residues on the Improvement of Acid-Proliferation-Type Photoimaging Materials, " *Journal of Photopolymer Science and Technology*, vol. 9, No. 1, pp. 29-30, 1996.

Lowe, "Synthesis of sulphonium salts," *The Chemistry of the Sulphonium Group*, Ed. Stirling et al., Chapter 11, pp. 267-312, 1981, John Wiley & Sons Ltd.

Jul. 17, 2013 Office Action issued in U.S. Appl. No. 13/476,629.

Sep. 12, 2013 Office Action issued in U.S. Appl. No. 13/476,700.

Sep. 30, 2013 European Search Report issued in European Application No. 12003989.6.

Dec. 16, 2013 Office Action issued in U.S. Appl. No. 13/476,700.

* cited by examiner

SULFONIUM SALT, POLYMER, METHOD FOR PRODUCING THE POLYMER, RESIST COMPOSITION AND PATTERNING PROCESS

BACKGROUND OF THE INVENTION

1. Field of the Invention

The present invention relates to a novel sulfonate advantageously usable as a photoacid generator and the like in a resist composition, a polymer using the same, a method for producing the polymer, a resist composition, and a patterning process.

2. Description of the Related Art

As LSI progresses toward a higher integration and a further acceleration in speed, a finer pattern rule is being requested. In such a movement, a deep-ultraviolet lithography is drawing an attention as the promising next-generation fine processing technology.

In recent years, technologies utilizing a KrF excimer laser having a high brightness and an ArF excimer laser having a further shorter wavelength have been drawing an attention as the light sources of a deep-ultraviolet ray. In addition, an ArF immersion lithography, which can be designed to have 1.0 or more of the numerical aperture (NA) of a projection lens by inserting a liquid having a higher refractive index than that of an air, such as water, ethylene glycol, and glycerin between the projection lens and a wafer, thereby attaining a high resolution, is rapidly drawing a growing attention (see, for example, Journal of Photopolymer Science and Technology Vol. 17, No. 4, p 587 (2004)). A further fine processing technology is sought due to shifting toward a shorter wavelength of the exposure light and attaining a higher resolution in the resist composition.

From this view point, a chemically amplified resist composition catalyzed by an acid, which has been developed recently, has excellent properties in sensitivity, resolution, and dry-etching resistance, and thus is a promising resist composition, particularly for a deep-ultraviolet lithography. In this chemically amplified resist composition, there are a positive type in which an exposed area is removed with leaving an unexposed area unremoved and a negative type in which an unexposed area is removed with leaving an exposed area unremoved.

In a chemically amplified positive resist composition using an alkaline developer, a resin and/or a compound whose part or all of alkaline-soluble phenol group or carboxylic acid group is protected by an acid-unstable protection group (an acid-labile group) is catalytically decomposed, by an acid generated by an exposure, to generate a phenol or a carboxylic acid in the exposed area, thereby removing this exposed area by an alkaline developer. On the other hand, in a chemically amplified negative resist composition, a resin and/or a compound having an alkaline-soluble phenol or carboxylic acid is crosslinked, by an acid generated by an exposure, with a compound (acid-crosslinker) that can link (crosslink) the resin or the compound by the acid to insolubilize the exposed part in an alkaline developer, thereby removing the unexposed part by the alkaline developer.

In the chemically amplified positive resist composition, a base resin having the acid-labile group and a compound generating the acid by radiation irradiation (hereinafter referred to as an photoacid generator for short) are dissolved in a solvent, and the resist solution thus prepared is applied on a substrate by various ways, heated if necessary and then the solvent is removed, to form a resist film. Subsequently, the formed resist film is exposed to a light source such as a deep-ultraviolet ray by radiation irradiation through a prescribed mask pattern. Further, as appropriate, a post exposure bake (PEB) is done after the exposure to carry out an acid-catalyzed reaction, and the development by an alkaline solution is done to remove the exposed area of the resist film to obtain a positive pattern profile. After the substrate is etched by various ways, the remaining resist film is removed by dissolving in a stripping solution or by asking to form a pattern profile on the substrate.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. An ArF immersion lithography, which can be designed to have 1.0 or more of the numerical aperture (NA) of a projection lens by inserting a liquid having a higher refractive index than that of an air, such as water, ethylene glycol, and glycerin between the projection lens and a wafer, thereby attaining a high resolution, is rapidly drawing a growing attention (see, for example, Journal of Photopolymer Science and Technology Vol. 17, No. 4, p 587 (2004)).

In the ArF lithography, a high sensitivity resist composition capable of achieving a high resolution at a small dose of exposure is required to prevent deterioration of precise and expensive optical system materials. Among several measures for realizing such a composition, the most common is to select each component which is highly transparent at the wavelength of 193 nm. For example, polyacrylic acid and derivatives thereof, norbornene-maleic anhydride alternating copolymers, polynorbornene, ring-opening metathesis polymers, hydrogenated ring-opening metathesis polymers and the like have been proposed as the base resin. This choice is effective to some extent in that the transparency of a resin alone is increased.

Studies have also been made on photoacid generators. In this case, when photoacid generators capable of generating alkane- or arene-sulfonic acid as used for conventional chemically amplified resist compositions for lithography using KrF excimer laser as a light source are used for a component of the above ArF chemically amplified resist compositions, it has been found that an acid strength to scissor acid labile groups on the resin is insufficient, resolution cannot be performed at all or sensitivity is low, and thus, these photoacid generators are not suited for the fabrication of devices.

For the above reason, photoacid generators capable of generating perfluoroalkanesulfonic acid having a high acid strength are generally used in ArF chemically amplified resist compositions. These photoacid generators capable of generating perfluoroalkanesulfonic acid have already been developed for use in the KrF resist compositions. For example, Japanese Patent Laid-Open (kokai) No. H11-282168 describes photoacid generators capable of generating perfluorohexanesulfonic acid, perfluorooctanesulfonic acid, perfluoro-4-ethylcyclohexanesulfonic acid, and perfluorobutanesulfonic acid. Japanese Patent Laid-Open (kokai) No. 2002-214774 describes novel photoacid generators capable of generating perfluoroalkyl ether sulfonic acids.

Among these compositions described above, perfluorooctanesulfonic acid derivatives (PFOS) have environmental problems such as nondegradability and concentration in the environment, so that manufacturers have made efforts to develop partially fluorinated alkane sulfonic acids having a reduced degree of fluorine substitution for alternatives. For example, Japanese Patent Application Publication No. 2004-531749 discloses a salt of α,α-difluoroalkanesulfonic acid, which is developed by using α,α-difluoroalkene and a sulfur compound, and resist compositions including a photoacid generator capable of generating the sulfonic acid by exposure, specifically, di(4-tert-butylphenyl)iodonium 1,1-difluoro-2-(1-naphthyl)ethanesulfonate, and furthermore, above-described Japanese Patent Laid-Open (kokai) No. 2002-214774 discloses difluorosulfoacetic acid alkyl esters, difluorosulfoacetic acid amides and the like in the text even though it does not describe a synthesis method of them.

However, in the case that a fine pattern with a pitch less than 200 nm is to be formed, problems regarding size difference (dependency on density) between an isolated pattern and a dense pattern having different optical contrast from each other and LER (line edge roughness) which shows roughness of a pattern have become larger. As a further finer pattern rule is being requested, remedial measures for avoiding deterioration of resolution and LER in addition to providing an excellent performance in sensitivity, an adhesion property with a substrate and etching resistance have been needed.

In such a movement, for improving line edge roughness, there is attempted an incorporation of acroyloxyphenyldiphenylsulfonium salt monomers in a base resin (see Japanese Patent Laid-Open (kokai) No. 20005-84365). However, in the above attempt, the monomers are bonded to the polymer at their cation side and therefore, a sulfonic acid generated by high energy beam irradiation is not different from a sulfonic acid generated from a conventional photoacid generator and they are not sufficient for solving the above problems. Moreover, there is also disclosed a sulfonium salt in which anion side such as polystyrene sulfonic acid is incorporated in a main chain of a polymer for improving sensitivity and resist pattern profile (see Japanese Patent No. 3613491). However, each generated acids is a derivative of an arene sulfonic acid or an alkyl sulfonic acid and has low acid strength and therefore, the generated acids are insufficient to scissor acid labile groups, especially acid labile groups of ArF chemically amplified resist compositions. Japanese Patent Laid-Open (kokai) No. 2006-178317 discloses many polymers having a partially fluorinated sulfonic acid anion as a polymerizable unit and resist compositions. Moreover, Japanese Patent Laid-Open (kokai) No. 2007-197718 describes three kinds of anions specifically, but these anions are expected to be highly hydrolyzable and low in stability because they are carboxylic acid ester of a strong acid. In addition, solubility of obtained copolymers in a resist solvent is not sufficient. Furthermore, Japanese Patent Laid-Open (kokai) No. 2008-133448 also discloses a sulfonium salt having a partially fluorinated alkanesulfonic acid anion as a polymerizable unit, but resolution is insufficient even though LER is improved a little, and therefore, it has been impossible to satisfy both of these parameters.

As an exposure technology after ArF lithography, electron beam (EB) lithography, $F_2$ lithography, EUV (extreme ultraviolet beam) lithography, X ray lithography and the like are drawing an attention as a promising technology. However, a sulfonic acid generated during exposure vaporizes due to a necessity of performing exposure under vacuum (under reduced pressure) and thereby there are a problem that a good pattern profile cannot be obtained and a possibility that the vaporized sulfonic acid damages an exposure apparatus. In addition, in EB and EUV lithography, it has been desired that resist compositions which can further suppress an impact of acid diffusion and provide a high resolution are developed for keeping up with a further pattern miniaturization in recent years.

The foregoing is essential also as a mask patterning process especially in an electron beam lithography, which is drawing an attention as an ultra-miniaturization process technology with 0.1 μm or less dimension. Deterioration of the pattern profile on a mask blanks becomes a serious problem in processing of the photomask blanks, because it also causes a pattern collapse as the integrated circuit pattern progresses toward further miniaturization in recent years.

SUMMARY OF THE INVENTION

The present invention was made in view of the situation as mentioned above and has an object to provide a sulfonium salt having a polymerizable functional group and being useful as a monomer for a base resin in a resist composition providing high resolution and excellent in LER in photolithography using a high energy beam such as an ArF excimer laser, an EUV light and an electron beam as a light source, a polymer obtained from the sulfonium salt, a method for producing the polymer, a resist composition including the polymer, and a patterning process using the resist composition.

In order to solve the above problems, the present invention provides a sulfonium salt represented by the following general formula (1).

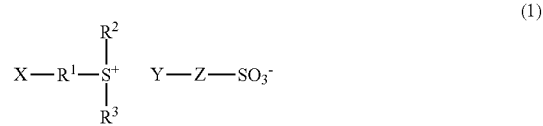

(1)

(In the formula, X and Y each represents a group having a polymerizable functional group; Z represents a divalent hydrocarbon group having 1 to 33 carbon atoms optionally containing a hetero atom; $R^1$ represents a divalent hydrocarbon group having 1 to 36 carbon atoms optionally containing a hetero atom; and $R^2$ and $R^3$ each represents a monovalent hydrocarbon group having 1 to 30 carbon atoms optionally containing a hetero atom or $R^2$ and $R^3$ may be bonded with each other to form a ring together with a sulfur atom in the formula.)

The sulfonium salt of the present invention represented by the foregoing general formula (1) is a novel sulfonate useful as an acid generator and has a feature of having a polymerizable functional group at an anion part and cation part thereof, and a base resin including a repeating unit obtained by using the sulfonium salt as a monomer forms crosslinkage moieties by an ionic bond among polymer chains. Therefore, at an exposed part after high energy beam irradiation, as an acid generates, the crosslinkage moieties are dissociated and molecular weight decreases, so that large contrast to an unexposed part can be obtained. In addition, such a sulfonium salt represented by the foregoing general formula (1) can be easily prepared. Therefore, a resist composition using a polymer, into which the sulfonium salt is introduced as a repeating unit, as a base resin is excellent in resolution and line edge roughness and thereby extremely useful as the resist composition for a fine and precision processing. In addition, the fluorine substitution rate of the sulfonium salt of the present invention is low, so that it exhibits a higher combustibility even upon disposal by combustion.

Further, it is preferable that the sulfonium salt is represented by the following general formula (2).

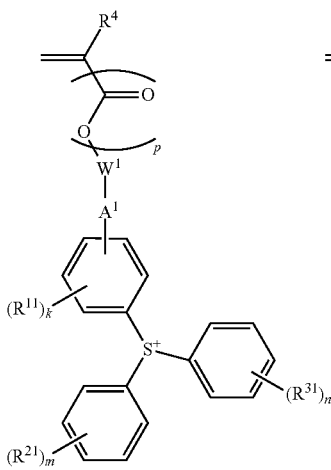

(2)

(In the formula, $W^1$ represents a single bond or a divalent hydrocarbon group having 1 to 30 carbon atoms optionally containing a hetero atom; $W^2$ represents a single bond or a divalent hydrocarbon group having 1 to 33 carbon atoms optionally containing a hetero atom; $A^1$ represents a single bond, an ether bond or an ester bond; each $R^{11}$, $R^{21}$ and $R^{31}$ independently represents a linear, a branched, or a cyclic alkyl group or alkoxy group having 1 to 10 carbon atoms; $R^{21}$ and $R^{31}$ may be bonded with each other to form a ring together with a sulfur atom in the formula; each $R^4$ and $R^5$ independently represents a hydrogen atom, a fluorine atom, a methyl group or a trifluoromethyl group; k represents 0 to 4; each m and n independently represents 0 to 5; and each p and q independently represents 0 or 1.)

As above, the sulfonium salt represented by the foregoing general formula (2) can be enumerated as a preferable embodiment of the sulfonium salt represented by the foregoing general formula (1).

Further, it is preferable that the sulfonium salt is represented by the following general formula (3).

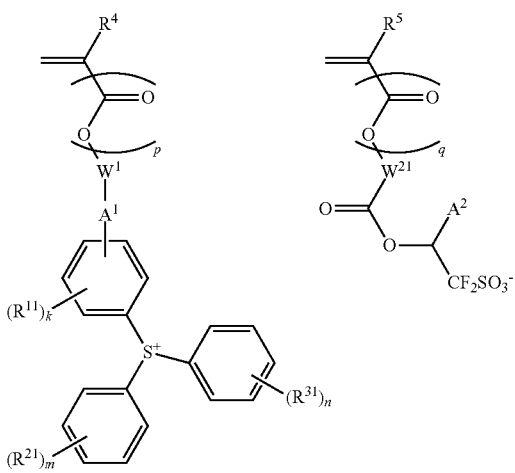

(3)

(In the formula, each $W^1$ and $W^{21}$ independently represents a single bond or a divalent hydrocarbon group having 1 to 30 carbon atoms optionally containing a hetero atom; $A^1$ represents a single bond, an ether bond or an ester bond; $A^2$ represents a hydrogen atom or a trifluoromethyl group; each $R^{11}$, $R^{21}$ and $R^{31}$ independently represents a linear, a branched, or a cyclic alkyl group or alkoxy group having 1 to 10 carbon atoms; $R^{21}$ and $R^{31}$ may be bonded with each other to form a ring together with a sulfur atom in the formula; each $R^4$ and $R^5$ independently represents a hydrogen atom, a fluorine atom, a methyl group or a trifluoromethyl group; k represents 0 to 4; each m and n independently represents 0 to 5; and each p and q independently represents 0 or 1.)

As above, the sulfonium salt represented by the foregoing general formula (3) can be enumerated as a preferable embodiment of the sulfonium salt represented by the foregoing general formula (1) and the foregoing general formula (2).

Further, the present invention provides a polymer including a repeating unit represented by the following general formula (4).

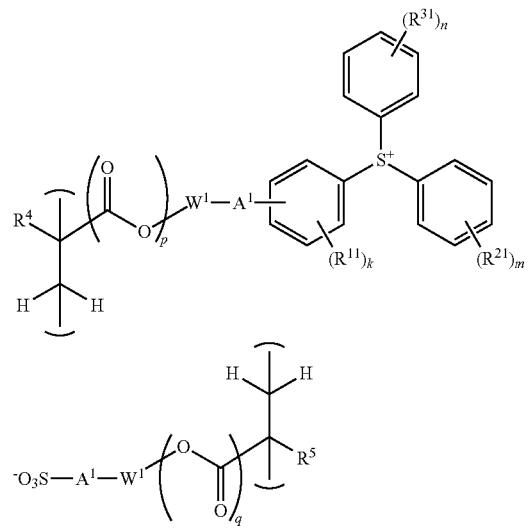

(4)

(In the formula, $W^1$ represents a single bond or a divalent hydrocarbon group having 1 to 30 carbon atoms optionally containing a hetero atom; $W^2$ represents a single bond or a divalent hydrocarbon group having 1 to 33 carbon atoms optionally containing a hetero atom; $A^1$ represents a single bond, an ether bond or an ester bond; each $R^{11}$, $R^{21}$ and $R^{31}$ independently represents a linear, a branched, or a cyclic alkyl group or alkoxy group having 1 to 10 carbon atoms; $R^{21}$ and $R^{31}$ may be bonded with each other to form a ring together with a sulfur atom in the formula; each $R^4$ and $R^5$ independently represents a hydrogen atom, a fluorine atom, a methyl group or a trifluoromethyl group; k represents 0 to 4; each m and n independently represents 0 to 5; and each p and q independently represents 0 or 1.)

A radiation-sensitive resist composition using such a polymer of the present invention as a base resin can largely improve a resist property such as resolution performance and LER and thereby it is extremely useful for a fine and precision processing.

Further, it is preferable that the polymer includes a repeating unit represented by the following general formula (5).

(5)

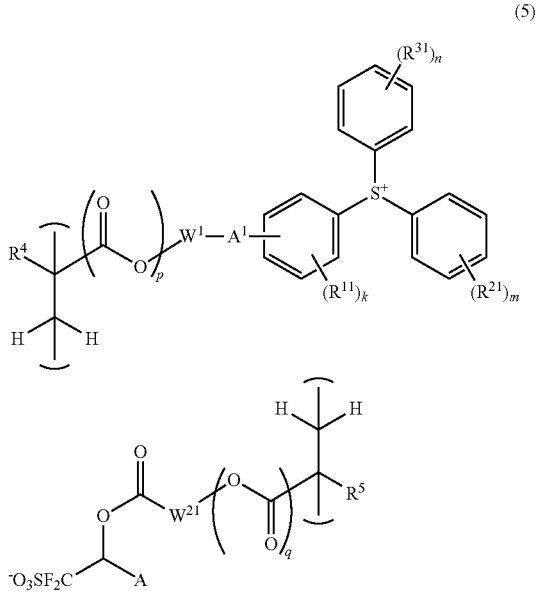

(In the formula, $W^{21}$ represents a single bond or a divalent hydrocarbon group having 1 to 30 carbon atoms optionally containing a hetero atom; $A^2$ represents a hydrogen atom or a trifluoromethyl group; and $W^1$, $A^1$, $R^{11}$, $R^{21}$, $R^{31}$, $R^4$, $R^5$, k, m, n, p and q represent the same as before.)

As above, among repeating units represented by the foregoing general formula (4), preferable is the polymer having a repeating unit represented by the foregoing general formula (5).

Further, the polymer can further include any one or more kinds of repeating units represented by the following general formulae (6) to (10).

(6)

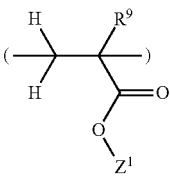

(7)

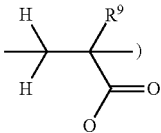

(8)

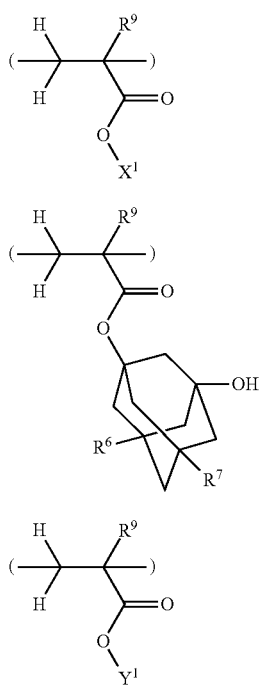

(9)

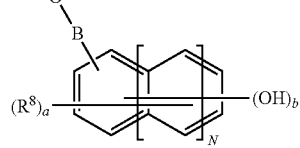

(10)

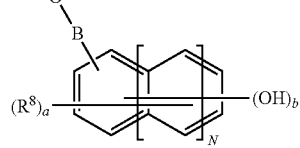

(In the formula, each $R^6$ and $R^7$ independently represents a hydrogen atom or a hydroxyl group; $R^8$ represents a hydrogen atom or an alkyl group having 1 to 10 carbon atoms; each $R^9$ independently represents a hydrogen atom, a fluorine atom, a methyl group or a trifluoromethyl group; $X^1$ represents an acid-labile group; $Y^1$ represents a substituent having a lactone structure; $Z^1$ represents a hydrogen atom, a fluoroalkyl group having 1 to 15 carbon atoms or a fluoroalcohol-containing substituent having 1 to 15 carbon atoms; N represents an integer of 0 to 2; B represents a single bond or a divalent organic group having 1 to 10 carbon atoms, which may be substituted by an oxygen atom; a represents an integer of 0 to 3; and b represents an integer of 1 to 3.)

As above, the polymer of the present invention can further include any one or more kinds of repeating units represented by the foregoing general formulae (6) to (10) in addition to a repeating unit represented by the foregoing general formula (4), preferably a repeating unit represented by the foregoing general formula (5).

Further, the polymer of the present invention can further include any one or more kinds of repeating units represented by the following general formulae (11) to (15).

(11)

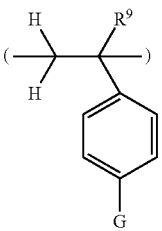

(12)

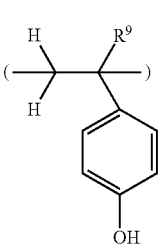

-continued

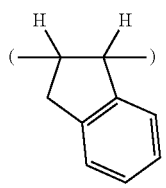 (13)

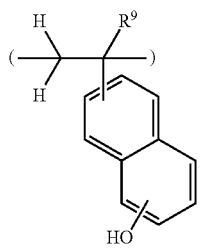 (14)

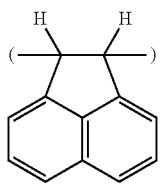 (15)

(In the formula, each $R^9$ independently represents a hydrogen atom, a fluorine atom, a methyl group or a trifluoromethyl group; $X^1$ represents an acid-labile group; G represents an oxygen atom or a carbonyloxy group (—C(=O)O—).)

As above, the polymer of the present invention can further include any one or more kinds of repeating units represented by the foregoing general formulae (11) to (15) in addition to a repeating unit represented by the foregoing general formula (4), preferably a repeating unit represented by the foregoing general formula (5).

Further, the present invention provides a method for producing a polymer, wherein at least, the polymer is obtained by copolymerizing a monomer represented by the following general formula (2-1) and a monomer represented by the following general formula (2-2).

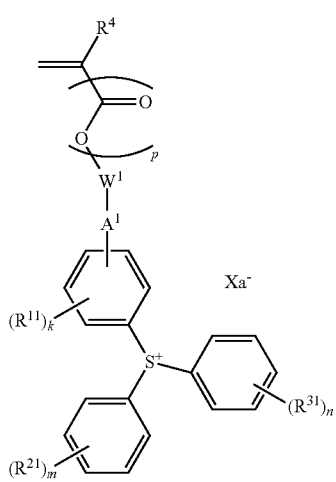 (2-1)

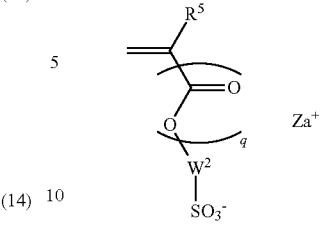 (2-2)

(In the formula, $Xa^-$ represents a non-nucleophilic anion; $Za^+$ represents a lithium ion, a sodium ion, a potassium ion, an ammonium ion, an iodonium ion or a sulfonium ion; $R^4$, $R^5$, $R^{11}$, $R^{21}$, $R^{31}$, $W^1$, $W^2$, $A^1$, p, q, k, m and n represent the same as before.)

As above, in the case that a monomer represented by the foregoing general formula (2-1) and a monomer represented by the foregoing general formula (2-2) are copolymerized, there exist two kinds of anions and two kinds of cations mixedly in the polymer matrix, and thus it is considered that an onium salt formed of a combination of the cation in the general formula (2-1) and the anion in the general formula (2-2) can exist. That is, a polymer including a repeating unit represented by the foregoing general formula (4) can be obtained by copolymerizing a monomer represented by the foregoing general formula (2-1) and a monomer represented by the foregoing general formula (2-2).

Further, the present invention provides a method for producing a polymer, wherein the polymer is obtained by blending a polymer containing a repeating unit represented by the following general formula (2-1)' and a polymer containing a repeating unit represented by the following general formula (2-2)'.

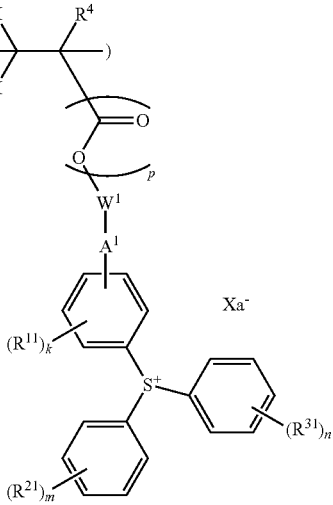 (2-1)'

-continued

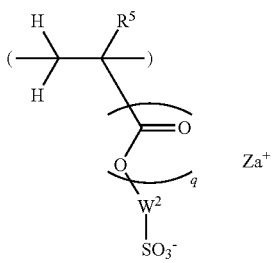

(2-2)'

(In the formula, $Xa^-$ represents a non-nucleophilic anion; $Za^+$ represents a lithium ion, a sodium ion, a potassium ion, an ammonium ion, an iodonium ion or a sulfonium ion; $R^4$, $R^5$, $R^{11}$, $R^{21}$, $R^{31}$, $W^1$, $W^2$, $A^1$, p, q, k, m and n represent the same as before.)

As above, a polymer including a repeating unit represented by the foregoing general formula (2-1)' and a polymer including a repeating unit represented by the foregoing general formula (2-2)' are each prepared and thereafter blended with each other, a polymer including a repeating unit represented by the foregoing general formula (4) can also be obtained.

Further, the present invention provides a resist composition, which contains the polymer as a base resin.

The polymer of the present invention can be used as a base resin of a resist composition, and the resist composition can largely improve a resist property such as resolution performance and LER and thereby extremely useful for a fine and precision processing.

Further, the present invention provides a resist composition, which contains the above polymer and a polymer not containing a repeating unit represented by the foregoing general formula (4) as a base resin.

As above, for preparation of the resist composition of the present invention, in addition to the above-described polymer of the present invention, other polymer such as a resin whose dissolution rate in an alkaline developer changes by action of an acid can be added as appropriate to prepare a base resin.

Further, the resist composition can further contain an acid generator other than an acid generator composed of a sulfonium salt represented by the following general formula (1).

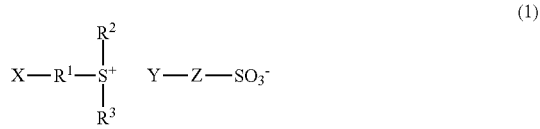

(1)

(In the formula, X and Y each represents a group having a polymerizable functional group; Z represents a divalent hydrocarbon group having 1 to 33 carbon atoms optionally containing a hetero atom; $R^1$ represents a divalent hydrocarbon group having 1 to 36 carbon atoms optionally containing a hetero atom; and $R^2$ and $R^3$ each represents a monovalent hydrocarbon group having 1 to 30 carbon atoms optionally containing a hetero atom or $R^2$ and $R^3$ may be bonded with each other to form a ring together with a sulfur atom in the formula.)

An acid generator other than an acid generator composed of the sulfonium salt represented by the foregoing general formula (1) can be added to the resist composition of the present invention as appropriate.

Further, the resist composition can further contain a quencher.

As above, when a quencher is added, resist sensitivity can be controlled easily, and in addition, because a diffusion rate of an acid in a resist film can be suppressed, resolution can be improved, a sensitivity change after exposure can be suppressed, dependence on a substrate and an environment can be reduced, and an exposure margin, a pattern profile and the like can be improved.

Further, the resist composition can further contain a surfactant that is insoluble in water and soluble in an alkaline developer.

In the resist composition of the present invention, in the case of the immersion exposure using water, especially when a resist top coat is not used, a surfactant having a function to reduce water penetration and leaching by orientating on a resist surface after spin coating may be added. This surfactant is of a polymer type having a property to be dissolved in an alkaline developer but not in water, and in particular the one giving a high water-repellent property with an improved sliding property is preferable.

Further, the present invention provides a patterning process comprising, at least, a step of coating the resist composition onto a substrate; a step of heat-treatment; a step of exposing by using a high energy beam via a photomask; and a step of developing by using a developer.

Such a patterning process of the present invention enables a pattern excellent in resolution and line edge roughness to be formed.

Further, the present invention provides a patterning process comprising, at least, a step of coating the resist composition onto a substrate; a step of heat-treatment; a step of coating a top coat which is insoluble in water and soluble in an alkaline developer; a step of inserting water between a projection lens and the substrate and exposing by using a high energy beam via a photomask; and a step of developing by using a developer.

As above, exposure can be done by a usual exposure method, and an immersion method in which the space between a projection lends and a substrate is immersed with a liquid can also be used. In that case, a top coat insoluble in water and soluble in an alkaline developer can also be used.

Further, the present invention provides a patterning process comprising, at least, a step of coating the resist composition onto a substrate; a step of heat-treatment; a step of performing a lithography by an electron beam; and a step of developing by using a developer.

As above, a pattern excellent in resolution and line edge roughness can also be formed by coating the resist composition onto a substrate and then performing a direct lithography by an electron beam without via a mask.

Further, a patterning process comprising, at least, a step of coating the resist composition onto a mask blanks on which a chrome compound film is formed; a step of heat-treatment; a step of performing a lithography by an electron beam; and a step of developing by using a developer is provided.

As above, in manufacturing a photomask by performing the above-mentioned pattern-forming on a photomask blanks, especially when used for processing of the photomask blanks having a chromium material on the outermost surface, the resist pattern is not easily affected based on the substrate dependency, and thus the patterning process of the present invention can be applied advantageously.

As explained above, the sulfonium salt of the present invention has a feature of having a polymerizable functional group at an anion part and cation part thereof, and a base resin including the sulfonium salt as a monomer forms crosslinkage moieties by an ionic bond among polymer chains. Therefore, at an exposed part after high energy beam irradiation, as an acid generates, the crosslinkage moieties are dissociated and molecular weight decreases, so that large contrast to an unexposed part can be obtained. As a result, a radiation-sensitive resist composition using the polymer of the present invention as a base resin can much improve resist properties such as resolution and LER and thereby it is extremely useful for a fine and precision processing. In addition, the fluorine substitution rate of the sulfonium salt of the present invention is low, so that it exhibits a higher combustibility even upon disposal by combustion.

DETAILED DESCRIPTION OF THE PREFERRED EMBODIMENTS

Figure 1:
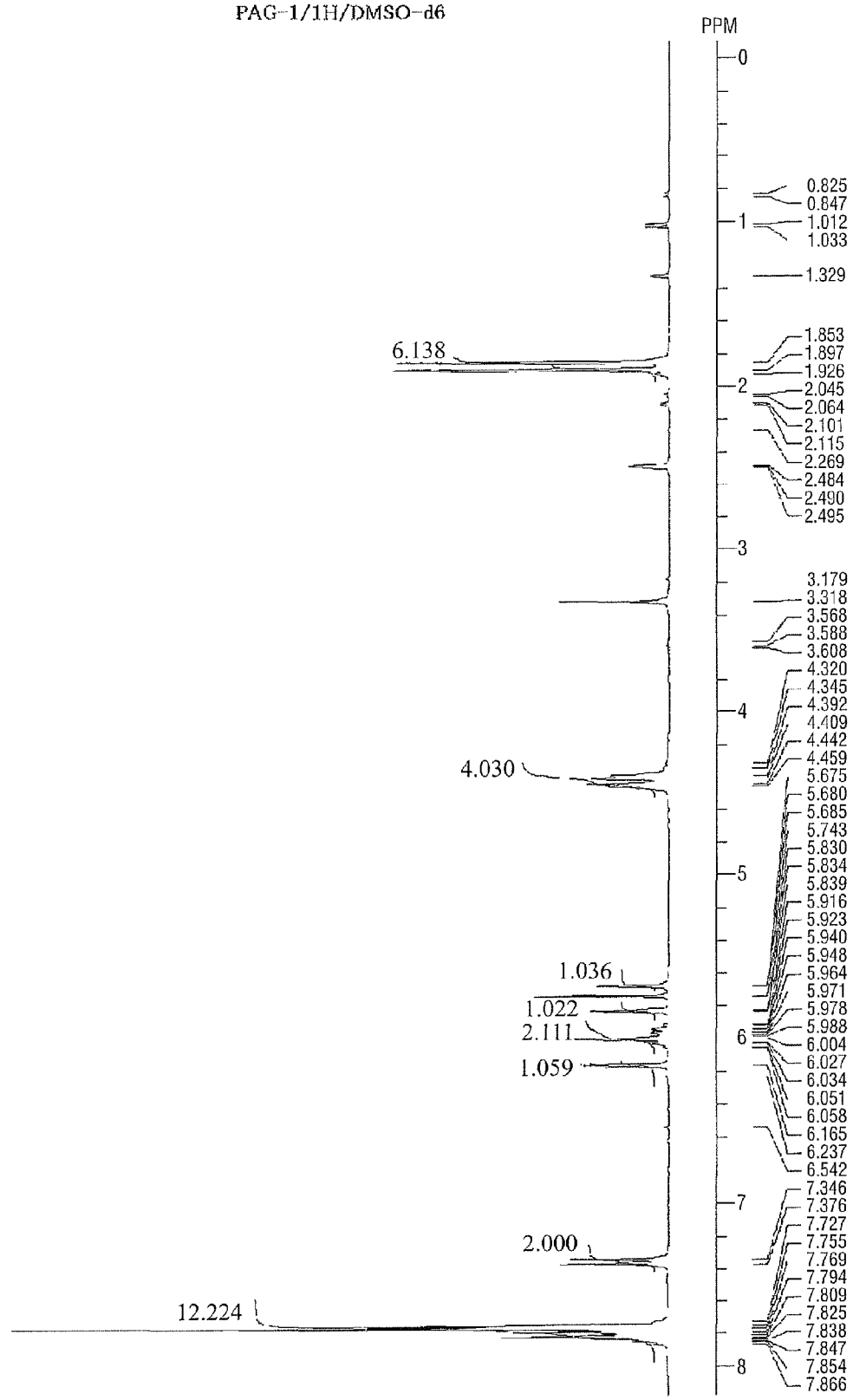
FIG. 1 is a diagram showing the $^1$H-NMR spectrum of PAG-1 in Synthesis Example 1-3.

As described above, heretofore, a resist composition excellent in both resolution and line edge roughness has been required.

In order to accomplish the above object, inventors of the present invention investigated extensively. As a result, they found that a sulfonium salt represented by the general formula (1) described later can be easily prepared, and a resist composition using a polymer, into which this sulfonium salt is introduced as a repeating unit, as a base resin is excellent in properties such as resolution and line edge roughness and extremely useful as a resist composition for a fine and precision processing, thereby succeeded in accomplishing the present invention.

That is, the present invention relates to (1) a sulfonium salt having a polymerizable functional group useful as a photoacid generator and starting materials of a sulfonic acid polymer, (2) a polymer containing the sulfonium salt as a monomer and generating a sulfonic acid by responding to high energy beam or heat and a method for producing the polymer, (3) a resist composition including the polymer, and (4) a patterning process using the resist composition.

Meanwhile, in the present invention, high energy beam includes ultraviolet ray, deep-ultraviolet ray, electron beam, EUV, X-ray, excimer laser, gamma-ray, synchrotron radiation and the like.

Hereinafter, the present invention will be described more specifically.

The sulfonium salt of the present invention having a polymerizable cation and a polymerizable anion is represented by the following general formula (1).

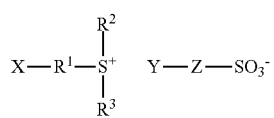

(In the formula, X and Y each represents a group having a polymerizable functional group; Z represents a divalent hydrocarbon group having 1 to 33 carbon atoms optionally containing a hetero atom; $R^1$ represents a divalent hydrocarbon group having 1 to 36 carbon atoms optionally containing a hetero atom; and $R^2$ and $R^3$ each represents a monovalent hydrocarbon group having 1 to 30 carbon atoms optionally containing a hetero atom or $R^2$ and $R^3$ may be bonded with each other to form a ring together with a sulfur atom in the formula.)

In the foregoing general formula (1), each X and Y independently represents a group having a polymerizable functional group. Examples of the polymerizable functional group include a substituent having a group such as vinyl, allyl, alkenyl, acryloyl, methacryloyl, styryl, and derivatives thereof. Among these polymerizable functional groups, an acryloyl group, a methacryloyl group and a styryl group are especially preferable in view of polymerizability and degree of difficulty in manufacturing.

Z represents a divalent hydrocarbon group having 1 to 33 carbon atoms optionally containing a hetero atom, and may have a linear, a branched, or a cyclic structure. Preferable examples of a hetero atom include oxygen, nitrogen, sulfur, fluorine and the like. Here, examples having a chain structure include methylene, ethylene, propylene, isopropylene, butylene, isobutylene, pentylene, 1,1-difluoroethoxycarbonylethylene and the like, while examples having a cyclic structure include an alkylene and an arylene as enumerated below.

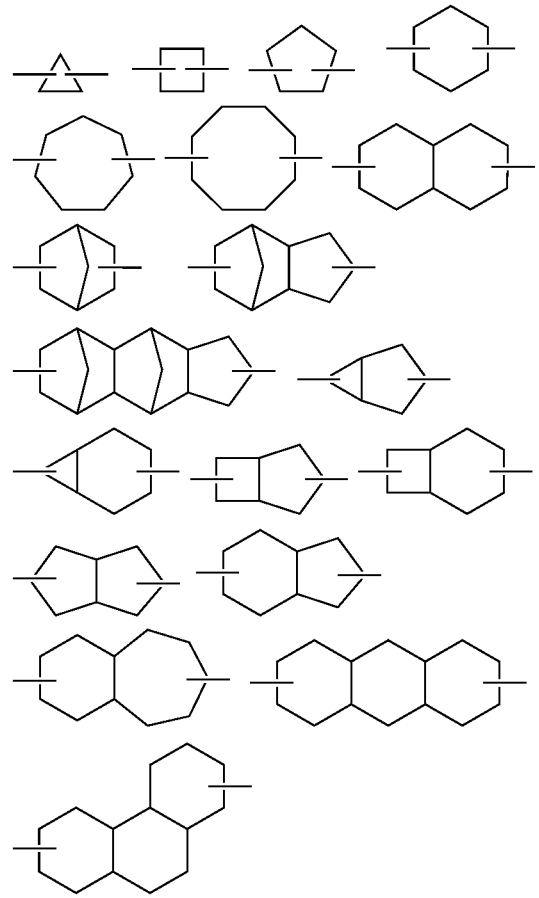

-continued

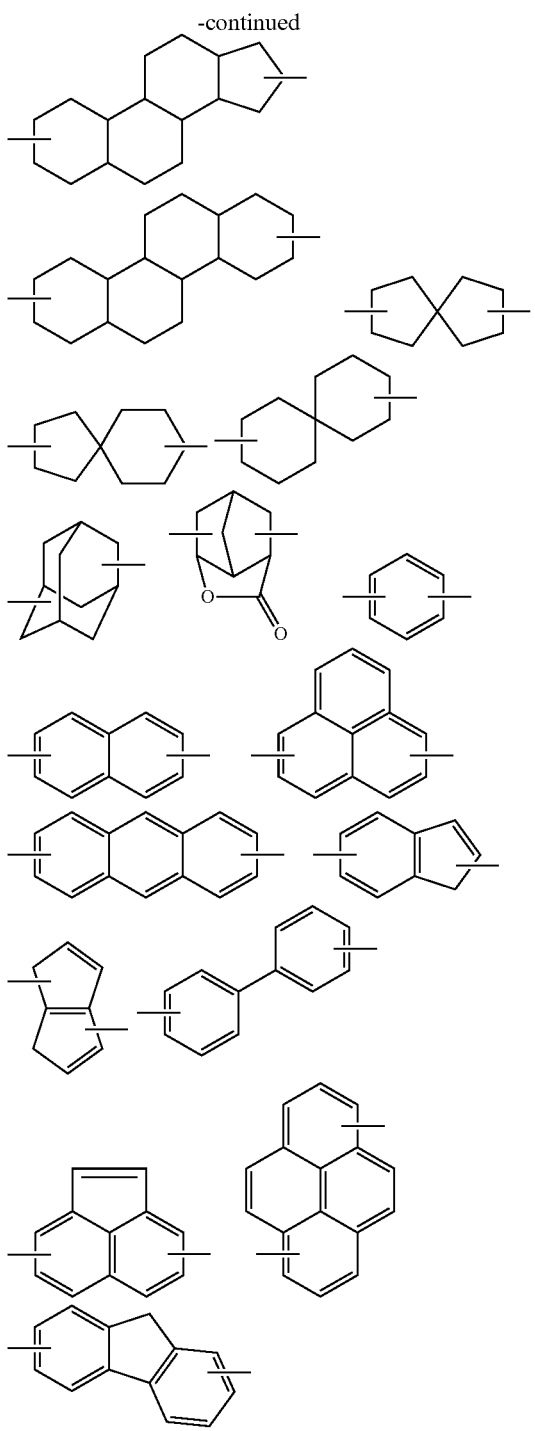

In addition, a composition in which a part of hydrogen atoms thereof are substituted with a hydroxyl group, an alkoxy group, a carboxyl group, an alkoxycarbonyl group, an oxo group, an amino group, an alkylamino group, a cyano group, a mercapto group, an alkylthio group, a sulfa group and the like is also exemplified.

In the foregoing formula (1), $R^1$ represents a divalent hydrocarbon group having 1 to 36 carbon atoms optionally containing a hetero atom, and may have a chain structure or a cyclic structure. Specifically, an alkylene group or an arylene group can be exemplified as $R^1$ as well as Z.

In the foregoing formula (1), each $R^2$ and $R^3$ represents a monovalent hydrocarbon group having 1 to 30 carbon atoms optionally containing a hetero atom, or $R^2$ and $R^3$ may be bonded with each other to form a ring together with a sulfur atom in the formula.

As for specific examples of a monovalent hydrocarbon group having 1 to 30 carbon atoms, examples of alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, adamantyl and the like. Examples of alkenyl groups include vinyl, allyl, propenyl, butenyl, hexenyl, cyclohexenyl and the like. Examples of oxoalkyl groups include 2-oxocyclopentyl, 2-oxocyclohexyl, 2-oxopropyl, 2-oxoethyl, 2-cyclopentyl-2-oxoethyl, 2-cyclohexyl-2-oxoethyl, 2-(4-methylcyclohexyl)-2-oxoethyl and the like. Examples of aryl groups include phenyl, naphthyl, thienyl and the like; alkoxyphenyl groups such as 4-hydroxyphenyl, 4-methoxyphenyl, 3-methoxyphenyl, 2-methoxyphenyl, 4-ethoxyphenyl, 4-tert-butoxyphenyl and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl and 2,4-dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Examples of aralkyl groups include benzyl, 1-phenylethyl and 2-phenylethyl. Examples of aryloxoalkyl groups include 2-aryl-2-oxoethyl groups such as 2-phenyl-2-oxoethyl, 2-(1-naphthyl)-2-oxoethyl, and 2-(2-naphthyl)-2-oxoethyl. When $R^2$ and $R^3$ are bonded with each other to form a ring structure via a sulfur atom, groups listed below are enumerated.

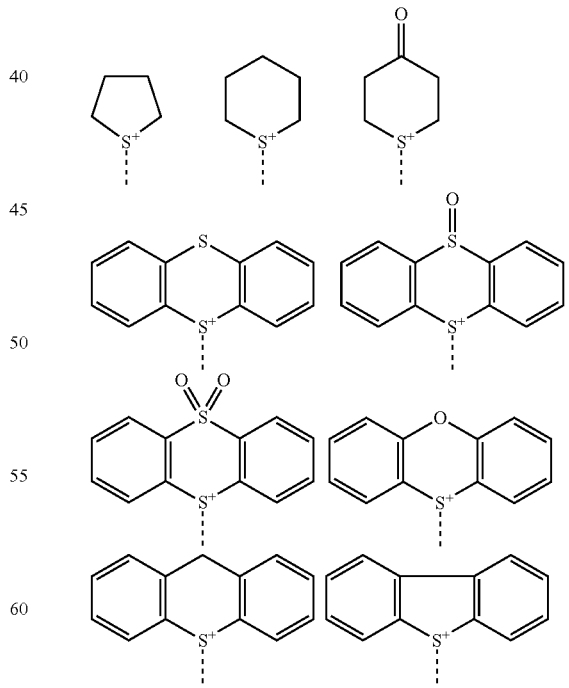

Preferable embodiments of the sulfonium salt represented by the foregoing general formula (1) can be represented by the following general formula (2).

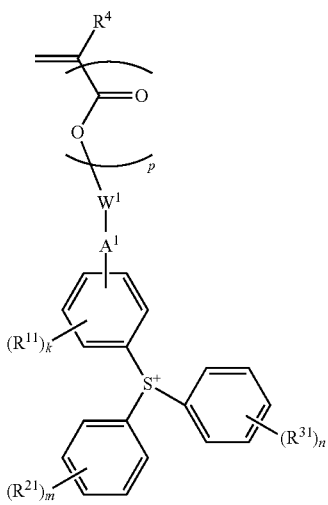

(2)

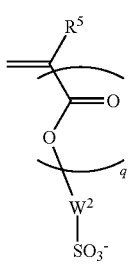

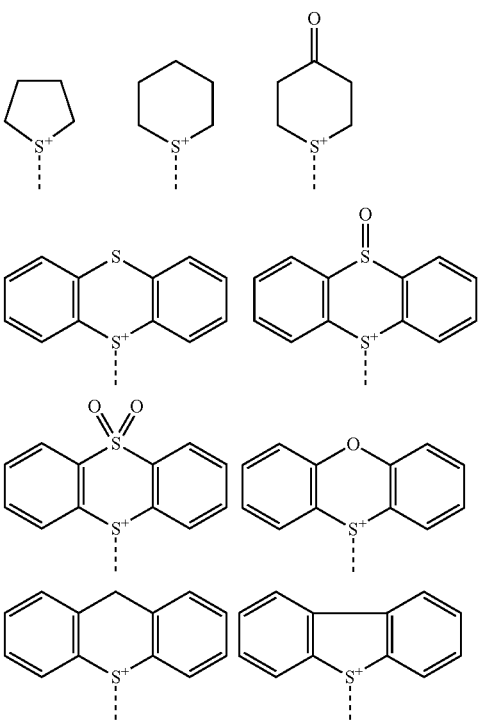

(In the formula, $W^1$ represents a single bond or a divalent hydrocarbon group having 1 to 30 carbon atoms optionally containing a hetero atom; $W^2$ represents a single bond or a divalent hydrocarbon group having 1 to 33 carbon atoms optionally containing a hetero atom; $A^1$ represents a single bond, an ether bond or an ester bond; each $R^{11}$, $R^{21}$ and $R^{31}$ independently represents a linear, a branched, or a cyclic alkyl group or alkoxy group having 1 to 10 carbon atoms; $R^{21}$ and $R^{31}$ may be bonded with each other to form a ring together with a sulfur atom in the formula; each $R^4$ and $R^5$ independently represents a hydrogen atom, a fluorine atom, a methyl group or a trifluoromethyl group; k represents 0 to 4; each m and n independently represents 0 to 5; and each p and q independently represents 0 or 1.)

$W^1$ represents a single bond or a divalent hydrocarbon group having 1 to 30 carbon atoms optionally containing a hetero atom. $W^2$ represents a single bond or a divalent hydrocarbon group having 1 to 33 carbon atoms optionally containing a hetero atom. Both of them may have a chain or a cyclic structure, and specifically, an alkylene group and an arylene group can be exemplified as $W^1$ and $W^2$ as well as Z in the foregoing general formula (1).

Each $R^{11}$, $R^{21}$ and $R^{31}$ independently represents a linear, a branched, or a cyclic alkyl group or alkoxy group having 1 to 10 carbon atoms. $R^{21}$ and $R^{31}$ may be bonded with each other to form a ring together with a sulfur atom in the formula. Examples of alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, adamantyl and the like, and examples of alkoxy groups include methoxy, ethoxy, propoxy, butoxy, t-butoxy, pentyloxy, hexyloxy, cyclohexyloxy and the like. In addition, when any two or more of $R^{11}$, $R^{21}$, and $R^{31}$ are bonded with each other to form a ring via a sulfur atom, groups listed below are enumerated.

Preferable embodiments of the sulfonium salt represented by the foregoing general formulae (1) and (2) can be represented by the following general formula (3).

(3)

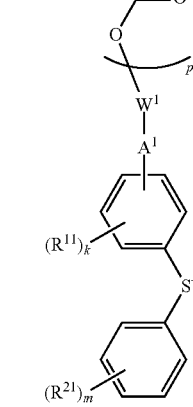
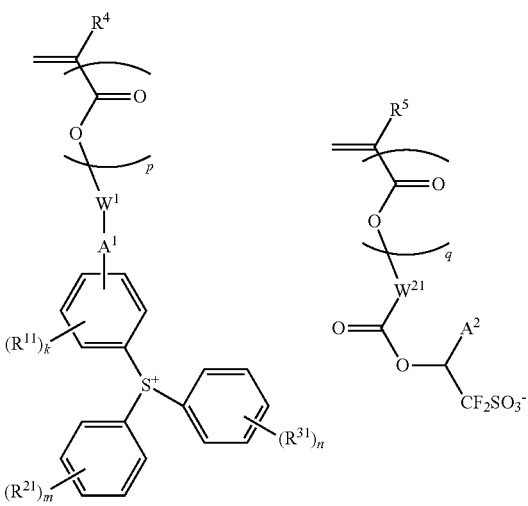

(In the formula, each $W^1$ and $W^{21}$ independently represents a single bond or a divalent hydrocarbon group having 1 to 30 carbon atoms optionally containing a hetero atom; $A^1$ represents a single bond, an ether bond or an ester bond; $A^2$ represents a hydrogen atom or a trifluoromethyl group; each $R^{11}$, $R^{21}$ and $R^{31}$ independently represents a linear, a branched, or a cyclic alkyl group or alkoxy group having 1 to 10 carbon atoms; $R^{21}$ and $R^{31}$ may be bonded with each other to form a ring together with a sulfur atom in the formula; each $R^4$ and $R^5$ independently represents a hydrogen atom, a fluorine atom, a methyl group or a trifluoromethyl group; k represents 0 to 4; each m and n independently represents 0 to 5; and each p and q independently represents 0 or 1.)

As a cation part structure in the sulfonium salt represented by the foregoing general formulae (1) to (3), structures listed below are exemplified specifically, but a cation of the sulfonium salt of the present invention is not limited thereto.

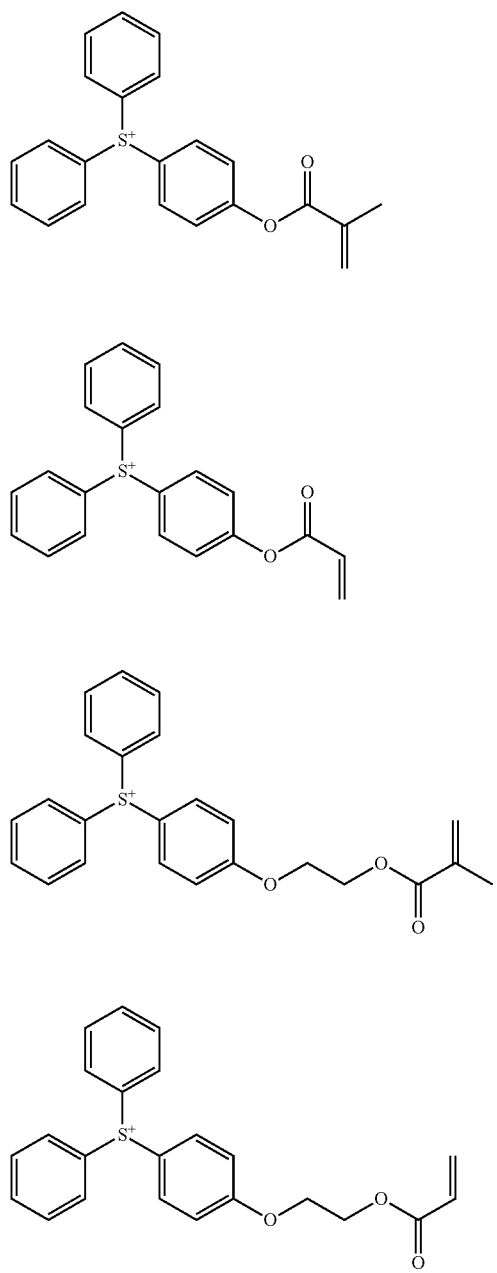

21
-continued
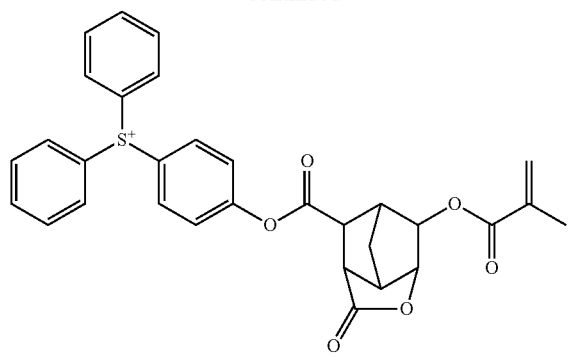
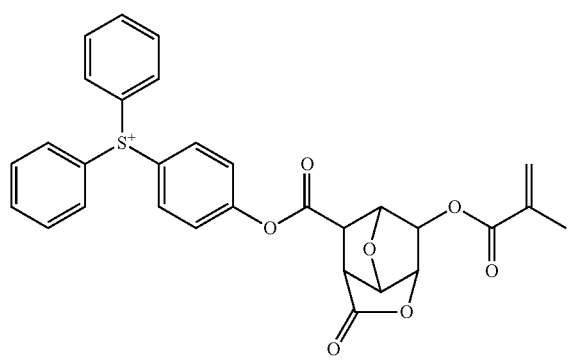
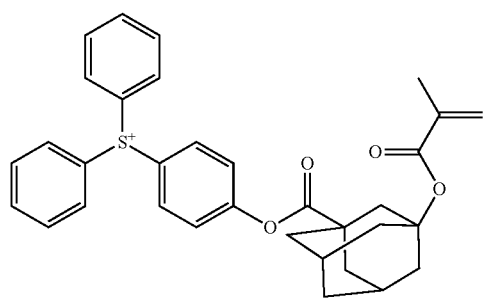
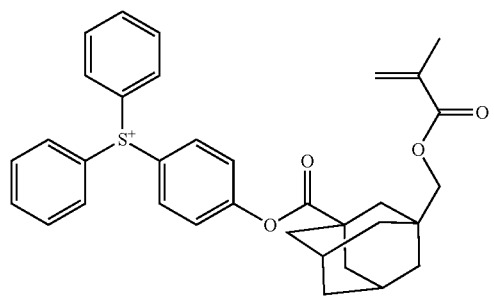
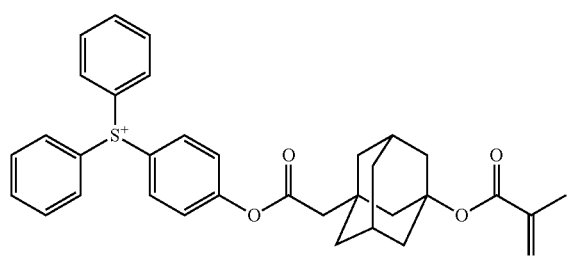
22
-continued
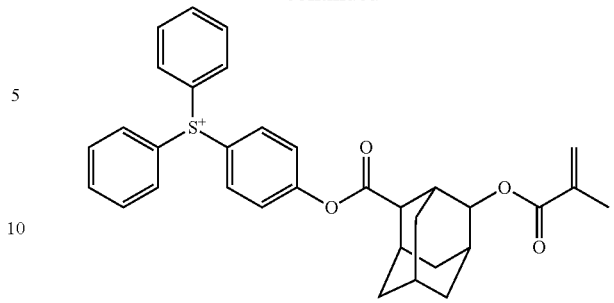
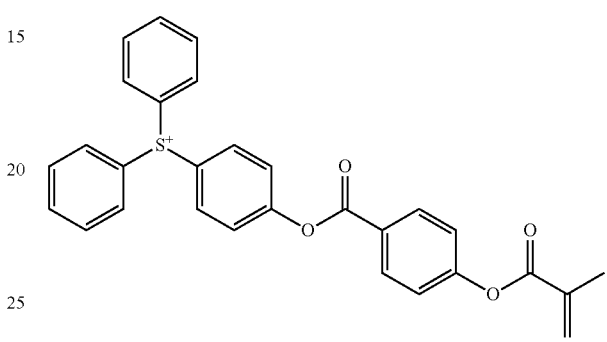
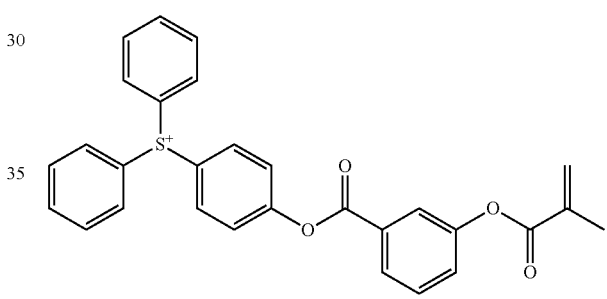
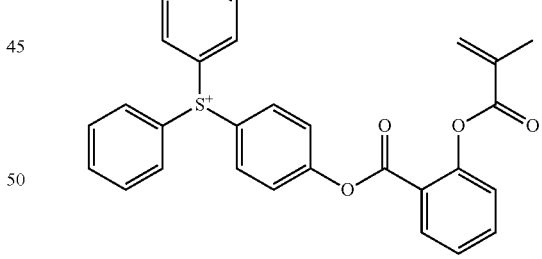
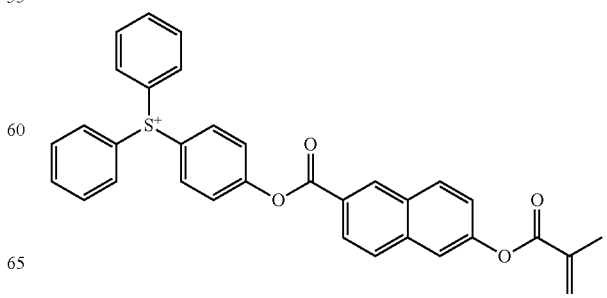

23
-continued
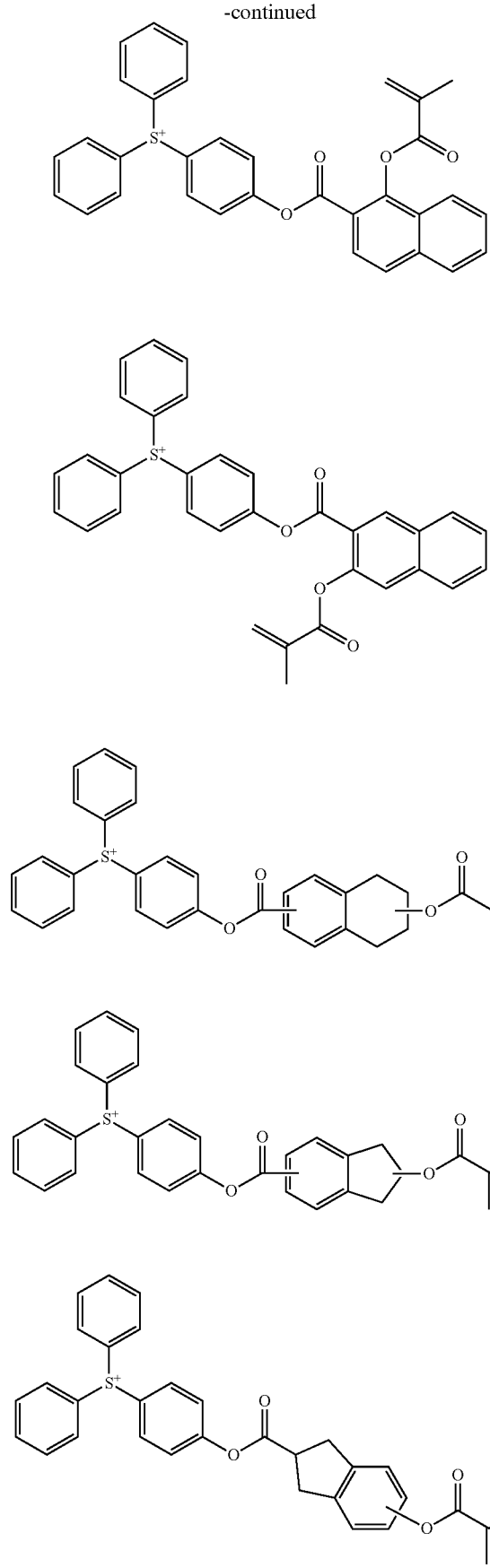
24
-continued
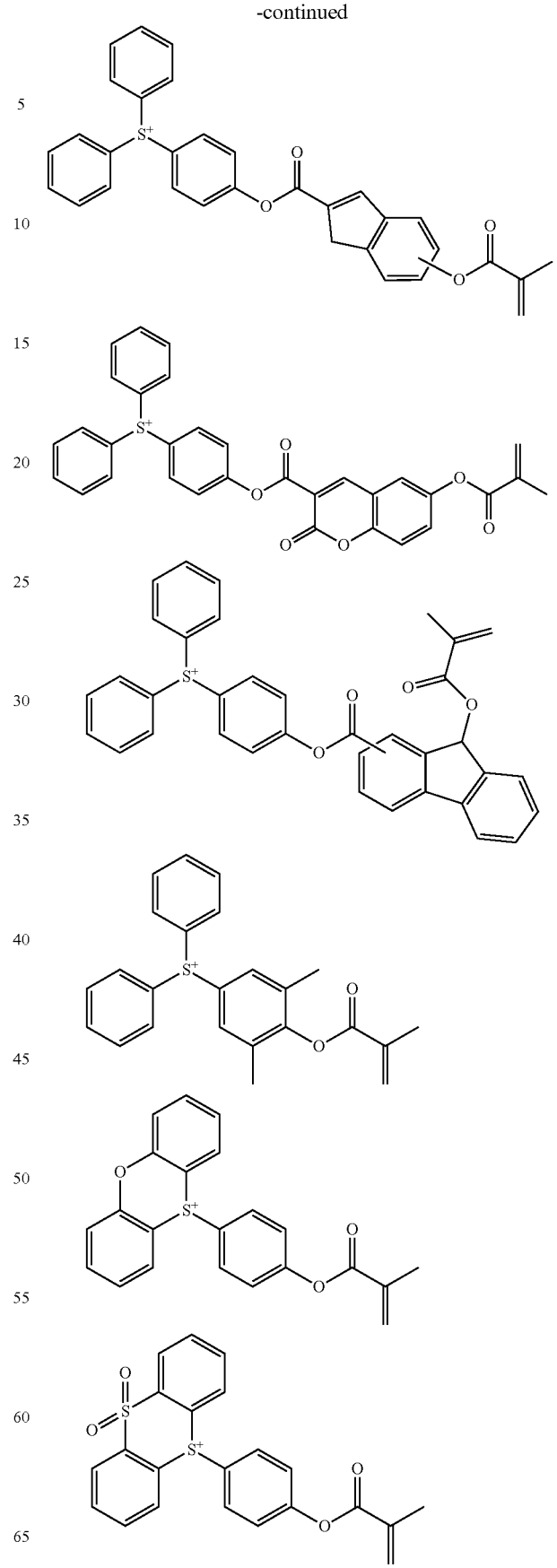

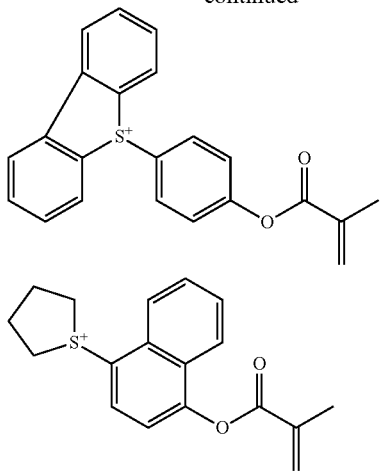
As an anion part structure of the sulfonium salt represented by the foregoing general formulae (1) to (3), structures listed below are exemplified specifically, but an anion of the sulfonium salt of the present invention is not limited thereto.
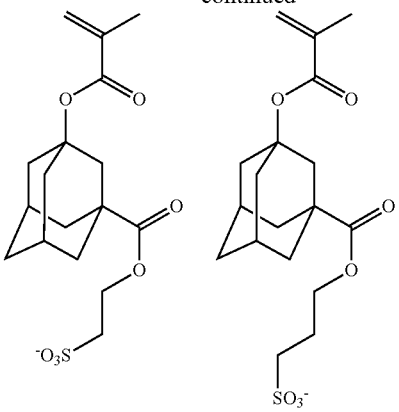
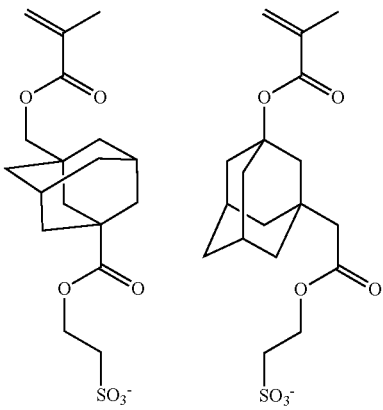
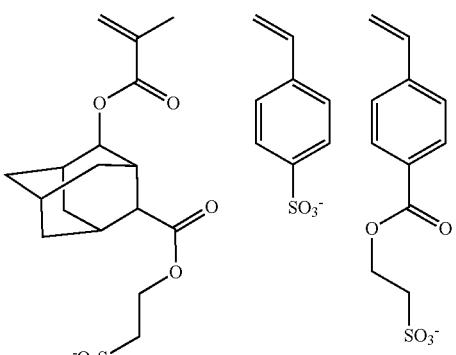
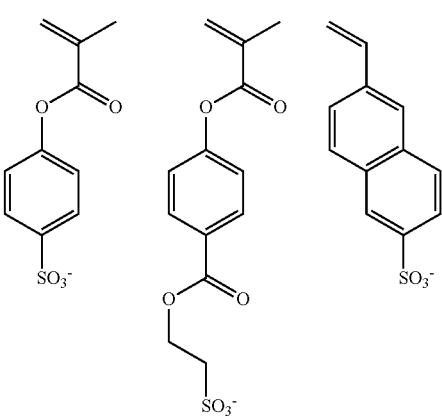

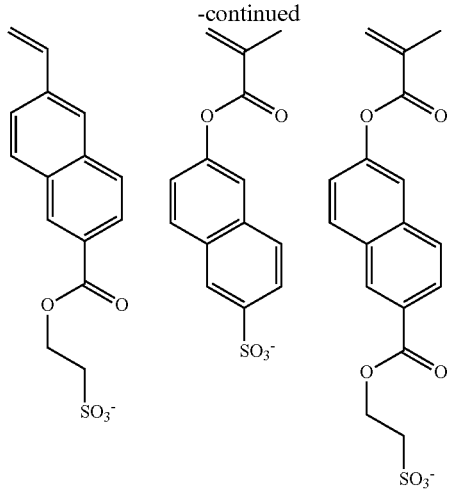
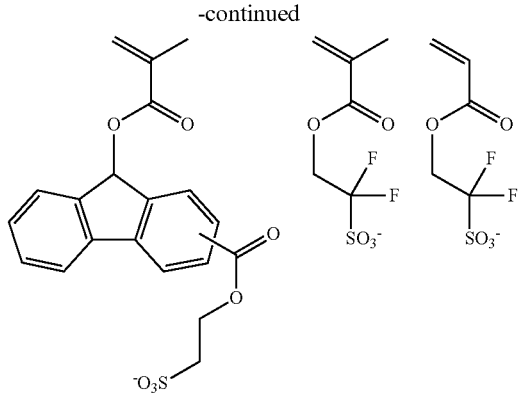
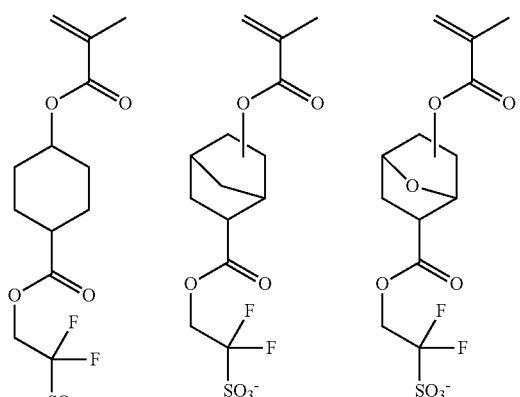
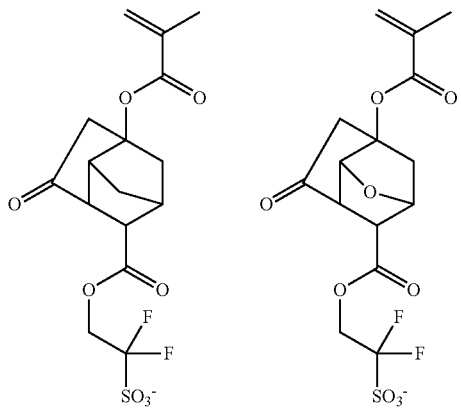
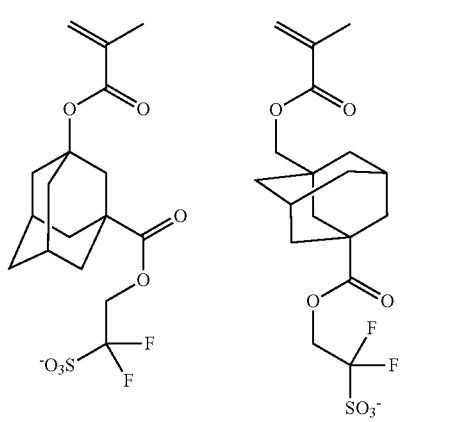

-continued
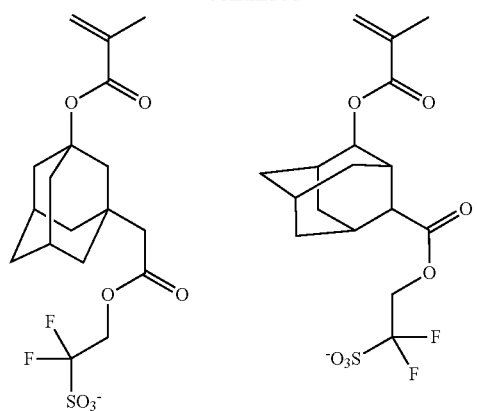
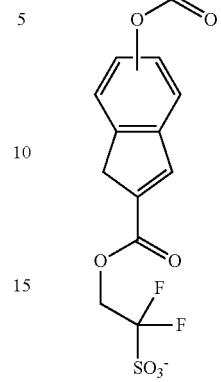
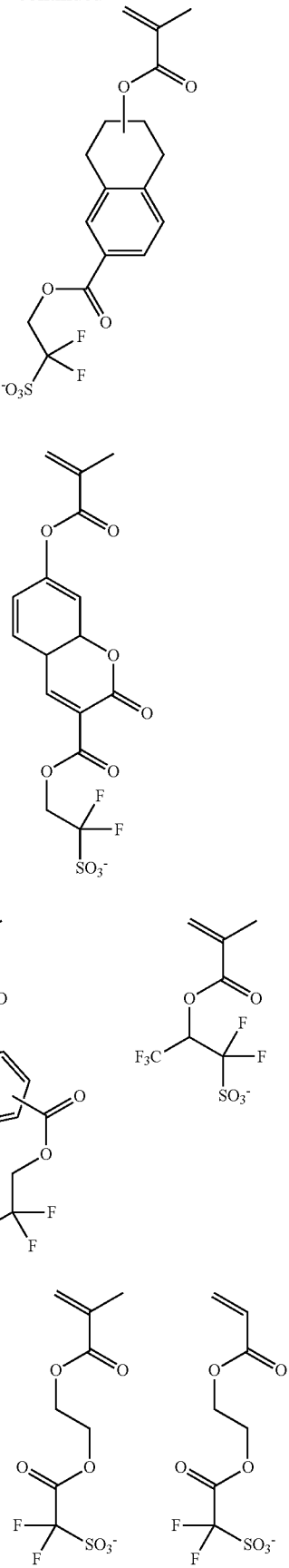

31
-continued
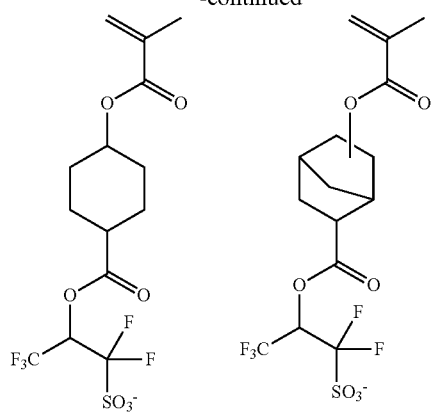
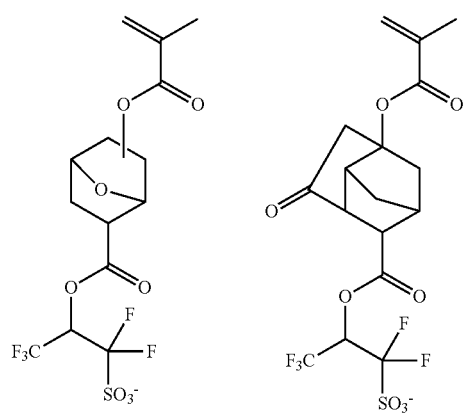
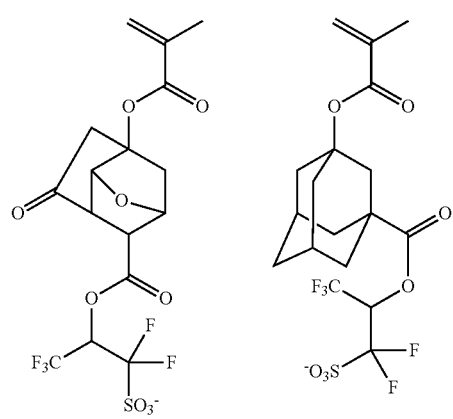
32
-continued
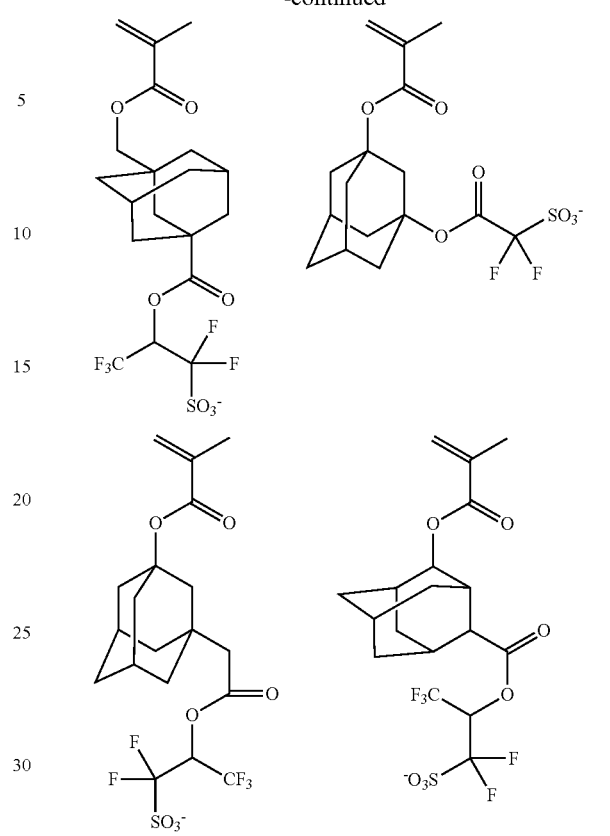
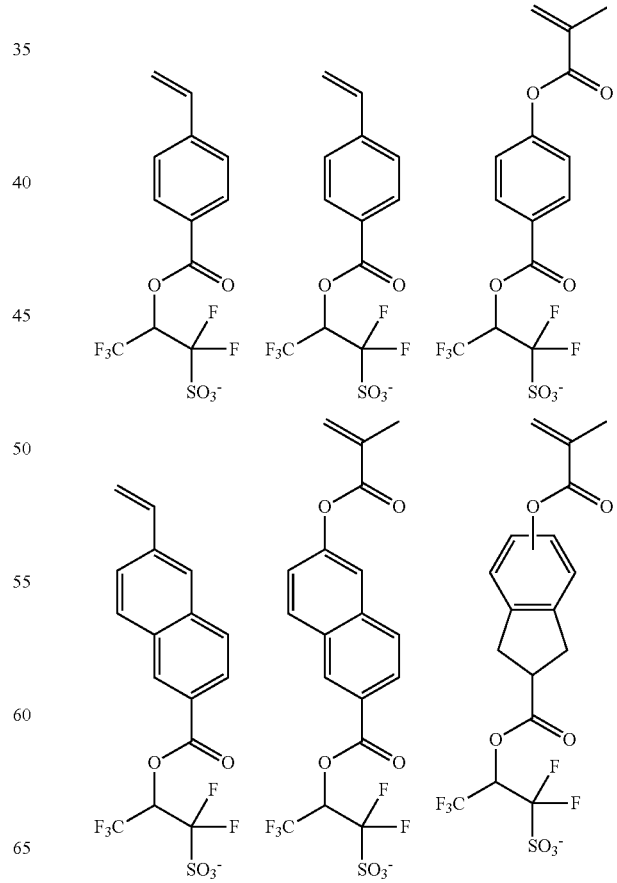

-continued

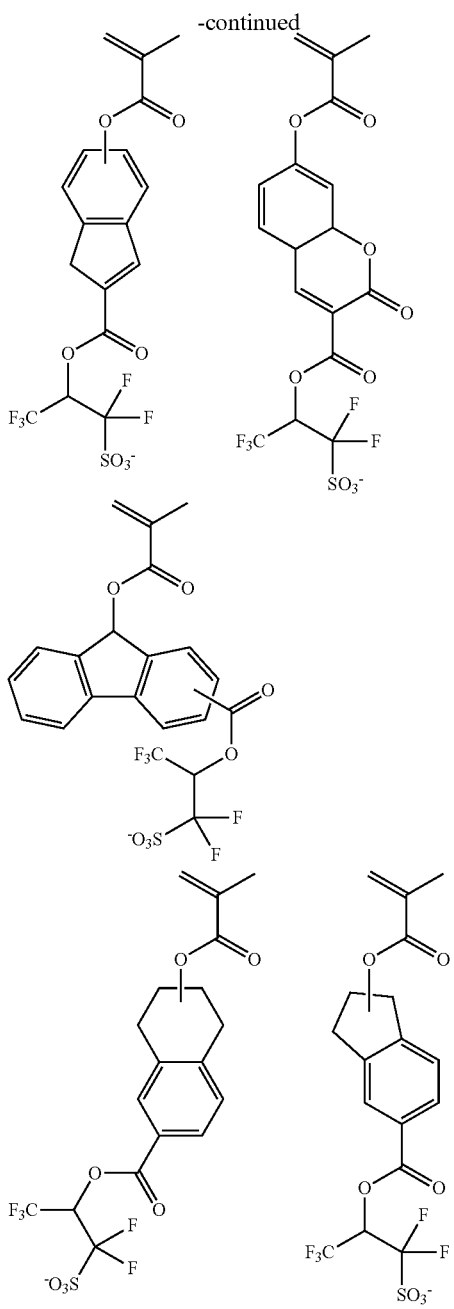

Examples of the sulfonium salt represent by the foregoing general formula (1) to (3) include a combination of the cation(s) with the anion(s) mentioned above. However, the sulfonium salt applicable to the present invention is not limited thereto.

Next, described below is how to synthesize the sulfonium salt represented by the foregoing general formula (1) of the present invention.

The sulfonium salt represented by the foregoing general formula (1) of the present invention can be synthesized in a manner that, for example, a sulfonium halide which has a polymerizable functional group such as a (meth)acryloyl group and a vinyl group and a sulfonic acid or sulfonate which also has a polymerizable functional group such as a (meth) acryloyl group and a vinyl group are mixed and ion-exchanged.

Meanwhile, the ion-exchange reaction is elaborated in Japanese Patent Laid-Open (kokai) No. 2007-145797 and so on. For example, a mixture of the sulfonate and the sulfonium halide is reacted in a bilayer system of dichloromethane-water, the water layer is removed, and then the organic layer is concentrated. In this way, the intended sulfonium salt can be synthesized and recovered. The sulfonate as a starting material may be ion-exchanged after once isolated or as a crude substance.

The sulfonium salt as starting materials can be synthesized by referring to "The Chemistry of sulfonium group Part 1", chap. 11, 267-312, John-Wiley & Sons (1981), "Advanced Photochemistry", vol. 17, 313-355, John-Wiley & Sons (1992), and the like. Further, the onium cation having an acryloyloxy group or a methacryloyloxy group as a polymerizable substituent can be synthesized by reacting an existing hydroxyphenyldiphenylsulfonium halide with acryloyl chloride or methacryloyl chloride under a basic condition by a method described in Japanese Patent Laid-Open (kokai) No. H4-230645, Japanese Patent Laid-Open (kokai) No. 2005-84365, and the like.

For an alternative method, the sulfonium salt represented by the foregoing general formula (1) of the present invention can also be synthesized by preparing a sulfonium salt having a polymerizable functional group at the anion part and then modifying the cation part with a polymerizable functional group. In addition, the intended substance can also be synthesized in an opposite manner of preparing a sulfonium salt having a polymerizable cation part and then modifying the anion part with a polymerizable functional group lastly.

Various methods for modifying a cation or an anion with a polymerizable functional group can be enumerated. For example, a sulfonium salt having an acryloyloxy group or a methacryloyloxy group, which is a polymerizable substituent, can be synthesized by reacting an anion or a cation having a hydroxyl group with acryloyl chloride or methacryloyl chloride under a basic condition.

Described below is how to synthesize a sulfonium salt represented by the foregoing general formula (3) of the present invention under a condition that $A^2$ is a trifluoromethyl group.

A carboxylic acid compound having a polymerizable functional group such as a (meth)acryloyl group and a vinyl group is turned into an acid chloride, and the acid chloride is reacted with triphenylsulfonium 1,1,3,3,3-pentafluoro-2-hydroxypropanesulfonate synthesized by the inventors of the present invention under a basic condition, and thereby the sulfonium salt in which $A^2$ of the foregoing general formula (3) is a trifluoromethyl group can be obtained.

Meanwhile, briefly described below is how to synthesize triphenylsulfonium 1,1,3,3,3-pentafluoro-2-hydroxypropanesulfonate. 1,1,3,3,3-pentafluoro-2-acyloxypropanesulfonate or 1,1,3,3,3-pentafluoro-2-arenecarbonyloxypropanesulfonate is obtained by reacting a 1,1,3,3,3-pentafluoropropene-2-yl aliphatic carboxylic acid ester or a 1,1,3,3,3-pentafluoropropene-2-yl aromatic carboxylic acid ester, which is typified by 1,1,3,3,3-pentafluoropropene-2-yl benzoate developed by using 1,1,1,3,3,3-hexafluoro-2-propanol as starting materials, in water respectively. Then, triphenylsulfonium 1,1,3,3,3-pentafluoro-2-acyloxypropanesulfonate or triphenylsulfonium 1,1,3,3,3-pentafluoro-2-arenecarbonyloxypropanesulfonate can be obtained by ion-exchanging with an arbitrary sulfonium salt. Moreover, a carboxylic acid ester moiety of the sulfonate is hydrolyzed by alkaline such as sodium hydrate and potassium hydrate or solvolyzed by an alcohol and a base. In this way, intended triphenylsulfonium 1,1,3,3,3-pentafluoro-2-hydroxypropanesulfonate can be obtained. Other sulfonium salts than triphenylsulfonium salts can also be synthesized in a similar way.

The reaction that a polymerizable anion is synthesized can be easily carried out by known methods, but it is preferable that a sulfonium salt such as triphenylsulfonium 1,1,3,3,3-pentafluoro-2-hydroxypropanesulfonate is dissolved in a solvent such as methylene chloride, tetrahydrofuran and acetonitrile and then, a base such as triethylamine, pyridine and 4-dimethylamino pyridine and an acid chloride compound containing a polymerizable functional group are added sequentially or at the same time, and furthermore, the mixture are cooled, heated or the like as appropriate to carry out the reaction.

Described below is how to synthesize a sulfonium salt represented by the foregoing general formula (3) of the present invention under a condition that $A^2$ is a hydrogen atom.

A carboxylic acid compound having a polymerizable functional group such as a (meth)acryloyl group and a vinyl group is turned into an acid chloride, and the acid chloride is reacted with triphenylsulfonium 1,1-difluoro-2-hydroxyethanesulfonate under a basic condition, and thereby the sulfonium salt having a polymerizable anion, in which $A^2$ of the foregoing general formula (3) is a hydrogen atom, can be obtained. It is preferable to use methylene chloride, tetrahydrofuran, acetonitrile and the like as a reaction solvent and to use triethylamine, pyridine, 4-dimethylamino pyridine and the like as a base. In addition, during the reaction, it is preferable that the mixture are cooled, heated or the like as appropriate.

Moreover, the sulfonium salt in which $A^2$ of the foregoing general formula (3) is a hydrogen atom can also be synthesized in a manner described below.

Triphenylsulfonium 1,1-difluoro-2-hydroxyethanesulfonate is reacted with chloroalkyl carboxylic acid chloride under a basic condition to prepare triphenylsulfonium 2-(chloroalkylcarbonyloxy)-1,1-difluoro-2-hydroxyethanesulfonate. Then, this prepared substance is reacted with a metal salt of a carboxylic acid having a polymerizable functional group such as a (meth)acryloyl group and a vinyl group or reacted with the carboxylic acid under a basic condition, and thereby, the sulfonium salt in which $A^2$ of the foregoing general formula (3) is a hydrogen atom can be obtained.

Here, briefly described below is how to synthesize triphenylsulfonium 1,1-difluoro-2-hydroxyethanesulfonate.

2-bromo-2,2-difluoroethanol and carboxylic chloride are reacted with each other to obtain 2-bromo-2,2-difluoroethylalkane carboxylate or 2-bromo-2,2-difluoroethylarene carboxylate, then the bromo group is turned into sodium sulfinate by a sulfur compound such as sodium dithionite, and then the sulfinic acid is turned into sulfonic acid by an oxidizing agent such as hydrogen peroxide.

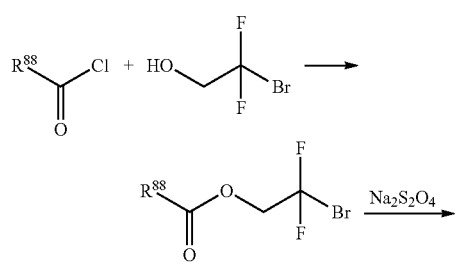

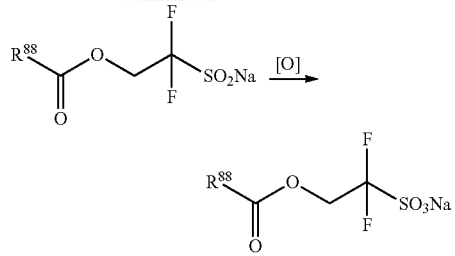

(In the above formula, $R^{88}$ represents a linear, a branched, or a cyclic alkyl group having 1 to 20 carbon atoms optionally containing a hetero atom.)

The esterification, the conversion from the halogenated alkane into the sodium sulfinate, and the conversion into sulfonic acid are well known, the latter two procedures are detailed in the Japanese Patent Laid-Open (kokai) No. 2004-2252 and the like. The intended sulfonium salt can be obtained by an ion-exchange reaction between the obtained sodium sulfonate and a sulfonium salt compound. The ion-exchange reaction is detailed in Japanese Patent Laid-Open (kokai) No. 2007-145797 or the like.

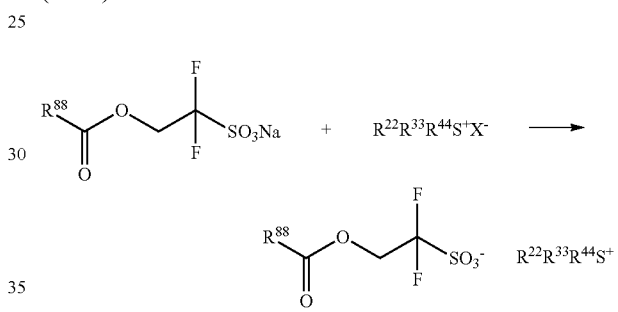

(In the above formula, each $R^{22}$, $R^{33}$ and $R^{44}$ independently represents a substituted or unsubstituted linear or branched alkyl group, alkenyl group, or oxoalkyl group having 1 to 10 carbon atoms, or a substituted or unsubstituted aryl group, aralkyl group, or aryloxoalkyl group having 6 to 18 carbon atoms, or alternatively, two or more of $R^{22}$, $R^{33}$ and $R^{44}$ may be bonded with each other to form a ring together with a sulfur atom in the formula. $R^{88}$ represents the same as before.)

Furthermore, triphenylsulfonium 1,1-difluoro-2-hydroxyethanesulfonate can be synthesized by ester hydrolyzing or solvolyzing an acyl group represented by $R^{88}CO$— as introduced in the above manner. The outline of the process is shown below.

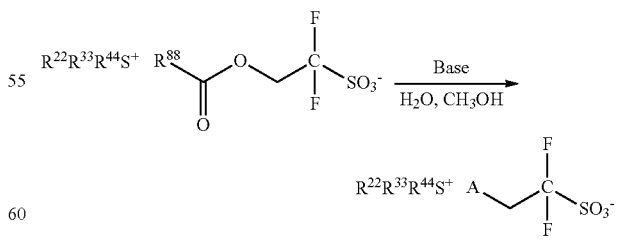

(In the above formula, $R^{22}$, $R^{33}$, $R^{44}$ and $R^{88}$ represent the same as before.)

A polymer of the present invention has a feature of including a repeating unit represented by the following general formula (4).

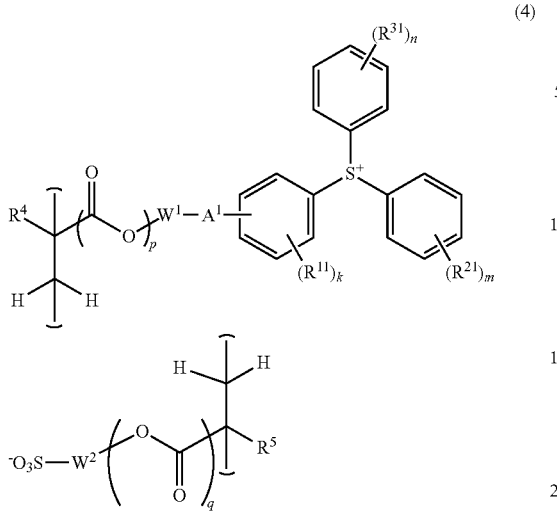

(In the formula, $W^1$ represents a single bond or a divalent hydrocarbon group having 1 to 30 carbon atoms optionally containing a hetero atom; $W^2$ represents a single bond or a divalent hydrocarbon group having 1 to 33 carbon atoms optionally containing a hetero atom; $A^1$ represents a single bond, an ether bond or an ester bond; each $R^{11}$, $R^{21}$ and $R^{31}$ independently represents a linear, a branched, a cyclic alkyl group or alkoxy group having 1 to 10 carbon atoms; $R^{21}$ and $R^{31}$ may be bonded with each other to form a ring together with a sulfur atom in the formula; each $R^4$ and $R^5$ independently represents a hydrogen atom, a fluorine atom, a methyl group or a trifluoromethyl group; k represents 0 to 4; each m and n independently represents 0 to 5; and each p and q independently represents 0 or 1.)

The above-described sulfonium salt of the present invention has a distinguishing feature of including polymerizable functional groups at both of its anion moiety and cation moiety. When this sulfonium salt is used as a repeating unit of a polymer included in a resist resin (base resin), it is presumable that a polymer chain obtained by a reaction of the polymerizable functional group of the anion moiety is occasionally different from a polymer chain obtained by a reaction of the polymerizable functional group of the cation moiety. However, it is considered that these different polymer chains are crosslinked by an ionic bond between the anion and the cation, and thereby they become substantially the same polymer chain. (See the following figure.)

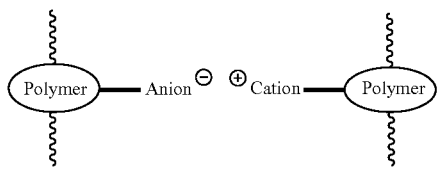

Therefore, when a pattern is formed by a photolithography step using such a resist composition of the present invention, a molecular weight of the resin at an exposed part decreases compared with that of before exposure because the crosslink shown in the above figure is uncoupled by generation of an acid from the sulfonium salt of the present invention. That is, environment of the exposed part is largely different from the unexposed part not only in a polar character because of deprotection of an acid labile group, but also in a molecular size. Therefore, as a result, a pattern having a large contrast and high resolution and being excellent in LER can be formed.

In addition, a polymer including a repeating unit represented by the foregoing general formula (4) of the present invention can also be obtained at least by copolymerizing a monomer represented by the following general formula (2-1) and a monomer represented by the following general formula (2-2).

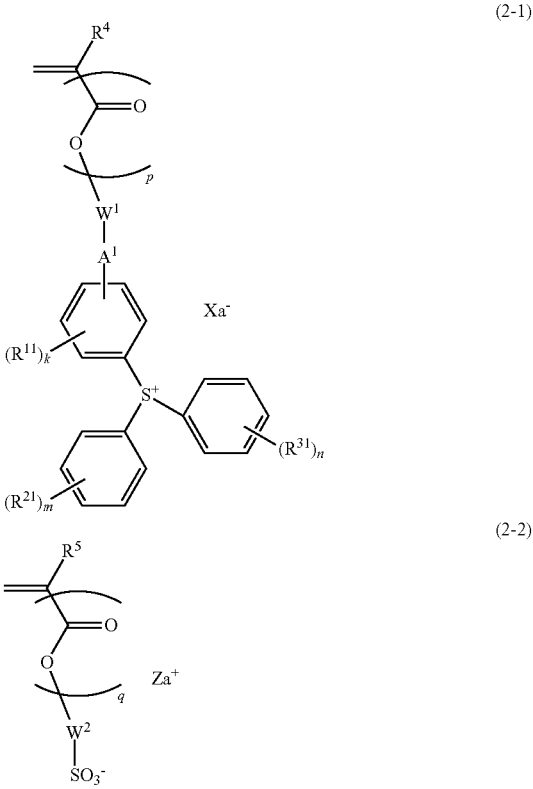

(In the formula, $Xa^-$ represents a non-nucleophilic anion; $Za^+$ represents a lithium ion, a sodium ion, a potassium ion, an ammonium ion, an iodonium ion or a sulfonium ion; $R^4$, $R^5$, $R^{11}$, $R^{21}$, $R^{31}$, $W^1$, $W^2$, $A^1$, p, q, k, m and n represent the same as before.)

In the foregoing general formula (2-1), the non-nucleophilic anion represented by $Xa^-$ is an organic anion or an inorganic anion, and more preferably an organic anion having a carbon atom.

Preferable examples of the non-nucleophilic anion represented by Xa include sulfonic acid anion, carboxylic acid anion, imidic acid anion, methide acid anion, $BE_4^-$, $PF_6^-$, $SbF_6^-$ and the like, and more preferably, sulfonic acid anion, carboxylic acid anion, imidic acid anion, methide acid anion and the like can be enumerated.

As a preferable monovalent non-nucleophilic anion represented by $Xa^-$, non-nucleophilic organic anions shown in the following constitutional formulae can be enumerated.

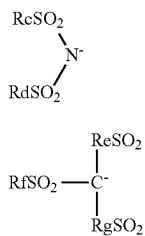

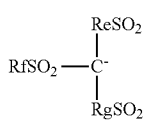

In the above constitutional formulae, each Ra, Rb, Rc, Rd, Re, Rf and Rg independently represents a monovalent hydrocarbon group. As for specific examples of a monovalent hydrocarbon group having 1 to 30 carbon atoms, examples of alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, adamantyl and the like. Examples of alkenyl groups include vinyl, allyl, propenyl, butenyl, hexenyl, cyclohexenyl and the like. Examples of oxoalkyl groups include 2-oxocyclopentyl, 2-oxocyclohexyl, 2-oxopropyl, 2-oxoethyl, 2-cyclopentyl-2-oxoethyl, 2-cyclohexyl-2-oxoethyl, 2-(4-methylcyclohexyl)-2-oxoethyl and the like. Examples of aryl groups include phenyl, naphthyl, thienyl and the like; 4-hydroxyphenyl; alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; dialkoxynaphthyl groups such as dimethoxynaphthyl and diethoxynaphthyl, and the like. Examples of aralkyl groups include benzyl, 1-phenylethyl, 2-phenylethyl and the like. Examples of aryloxoalkyl groups include 2-aryl-2-oxoethyl groups such as 2-phenyl-2-oxoethyl, 2-(1-naphthyl)-2-oxoethyl, 2-(2-naphthyl)-2-oxoethyl and the like. In addition, a part of hydrogen atoms thereof may be substituted with a fluorine atom or a trifluoromethyl group. Furthermore, a group, in which a plurality of these monovalent hydrocarbon groups are bonded by a functional group such as an ether bond, an ester bond, a sulfide bond, a sulfone bond, an amide bond and a carbonate bond, can be enumerated.

Rc and Rd, and Re, Rf and Rg may be bonded with each other to form a ring. As a group which is to form a ring, an alkylene group and an arylene group and the like are enumerated.

Among the foregoing general formulae (Xa-1) to (Xa-4), especially preferable is an anion represented by the general formula (Xa-1).

In the general formula (2-2), $Za^+$ represents a lithium ion, a sodium ion, a potassium ion, an ammonium ion, an iodonium ion or a sulfonium ion.

When $Za^+$ is an ammonium ion, a sulfonium ion, or an iodonium ion, $Za^+$ is represented by the following general formula (Za-1).

$(R^{41})_{m'}A'^{+}$ (Za-1)

(In the formula, A' represents a nitrogen atom, a sulfur atom or an iodine atom. Each $R^{41}$ independently represents a hydrogen atom, a substituted or unsubstituted linear, branched or cyclic alkyl group, alkenyl group or oxoalkyl group having 1 to 10 carbon atoms, or a substituted or unsubstituted aryl group, aralkyl group or aryloxoalkyl group having 6 to 18 carbon atoms, or alternatively, any two or more of $R^{41}$ may be bonded with each other to form a ring together with A' in the formula. Meanwhile, in the case that A' is a sulfur atom or an iodine atom, $R^{41}$ is not a hydrogen atom. In addition, in the case that A' is a nitrogen atom, sulfur atom and an iodine atom, m' is 4, 3 and 2 respectively.)

As a substituent in $R^{41}$, a hydroxy group, an alkoxy group, a halogen atom, a carbonyl group and the like are enumerated, while as $R^{41}$, groups listed below are enumerated specifically.

Examples of alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, adamantyl and the like. Examples of alkenyl groups include vinyl, allyl, propenyl, butenyl, hexenyl, cyclohexenyl and the like. Examples of oxoalkyl groups include 2-oxocyclopentyl, 2-oxocyclohexyl, 2-oxopropyl, 2-oxoethyl, 2-cyclopentyl-2-oxoethyl, 2-cyclohexyl-2-oxoethyl, 2-(4-methylcyclohexyl)-2-oxoethyl and the like. Examples of aryl groups include phenyl, naphthyl, thienyl and the like; alkoxyphenyl groups such as 4-hydroxyphenyl, p-methoxyphenyl, m-methoxyphenyl, o-methoxyphenyl, p-ethoxyphenyl, p-tert-butoxyphenyl and m-tert-butoxyphenyl; alkylphenyl groups such as 2-methylphenyl, 3-methylphenyl, 4-methylphenyl, ethylphenyl, 4-tert-butylphenyl, 4-butylphenyl and 2,4-dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; dialkoxynaphthyl groups such as dimethoxynaphthyl and diethoxynaphthyl, and the like. Examples of aralkyl groups include benzyl, 1-phenylethyl, 2-phenylethyl and the like. Examples of aryloxoalkyl groups include 2-aryl-2-oxoethyl groups such as 2-phenyl-2-oxoethyl, 2-(1-naphthyl)-2-oxoethyl and 2-(2-naphthyl)-2-oxoethyl, and the like.

When A' is a nitrogen atom and any two or more of $R^{41}$ are bonded with each other to form a ring together with the nitrogen atom, a structure such as piperidine, morpholine, pyridine, quinoline, acridine, imidazole and benzimidazole, and the like are enumerated, and the nitrogen atom may be protonated or alkylated. Further, an aryl group having a polymerizable substituent group such as acryloyloxy and methacryloyloxy is enumerated, and specifically, 4-(acryloyloxy)phenyl, 4-(methacryloyloxy)phenyl, 4-vinyloxyphenyl, 4-vinylphenyl and the like are enumerated. In addition, when A' is a sulfur atom and any two of $R^{41}$ are bonded with each other to form a ring together with the sulfur atom, a structure such as tetrahydrothiophene, 1,4-thioxane, dibenzothiophene and phenoxathiin is enumerated.

As examples of more specific $(R^{41})_{m'}A'^{+}$, when A' is a nitrogen atom, ammonium, trimethylammonium, tetramethylammonium, triethylammonium, tributylammonium, tetrabutylammonium, trioctylammonium, anilinium, 2,6-dimethylanilinium, N,N-dimethylanilinium, benzyltrimethylammonium, benzyltriethylammonium, benzyltripropylammonium, N-benzyl-N,N-dimethylanilinium N-(p-methoxy)benzyl-N,N-dimethylanilinium and the like are enumerated. When A' is a sulfur atom, triphenylsulfonium, 4-hydroxyphenyldiphenylsulfonium, bis(4-hydroxyphenyl)phenylsulfonium, tris(4-hydroxyphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-ditert-butoxyphenyl)diphenylsulfonium, bis (3,4-ditert-butoxyphenyl)phenylsulfonium, tris(3,4-ditert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, dimethyl-2-naphthylsulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl2-thienylsulfonium, 4-n-butoxynaphthyl-1-thiacyclopentanium, 2-n-butoxynaphthyl-1-thiacyclopentanium, 4-methoxy naphthyl-1-thiacyclopentanium, 2-methoxynaphthyl-1-thiacyclopentanium, 4-methylphenyldiphenylsulfonium, 4-ethylphenyldiphenylsulfonium, 4-tert-butylphenyldiphenylsulfonium, 4-cyclohexylphenyldiphenylsulfonium, 4-n-hexylphenyldiphenylsulfonium, 4-n-octylphenyl diphenylsulfonium, 4-methoxyphenyldiphenylsulfonium, 4-ethoxyphenyldiphenylsulfonium, 4-cyclohexyloxyphenyldiphenylsulfonium, 4-n-hexyloxyphenyldiphenylsulfonium, 4-n-octyloxyphenyldiphenylsulfonium, 4-dodecyloxyphenydiphenylsulfonium, 4-trifluoromethylphenyldiphenylsulfonium, 4-trifluoromethyloxyphenyl diphenylsulfonium, 4-tert-butoxycarbonylmethyloxyphenyldiphenylsulfonium, 10-phenylphenoxthinium and the like are enumerated. More preferably triphenylsulfonium, 4-tert-butylphenyldiphenylsulfonium, 4-tert-butoxyphenyldiphenylsulfonium, tris(4-tert-butylphenyl)sulfonium, (4-tert-butoxycarbonylmethyloxyphenyl)diphenylsulfonium, diphenylmethylsulfonium, dimethylphenylsulfonium, 2-oxo-2-phenylethylthiacyclopentanium, 10-phenylphenoxthinium and the like are enumerated. When A' is an iodine atom, bis(4-methylphenyl)iodonium, bis(4-ethylphenyl)iodonium, bis(4-tert-butylphenyl)iodonium, bis(4-(1,1-dimethylpropyl)phenyl)iodonium, 4-methoxyphenylphenyliodonium, 4-tert-butoxyphenylphenyliodonium, 4-acryloyloxyphenylphenyliodonium, 4-methacryloyloxyphenylphenyliodonium and the like are enumerated.

In the case that a monomer represented by the foregoing general formula (2-1) and a monomer represented by the foregoing general formula (2-2) are copolymerized, there exist two kinds of anions and two kinds of cations mixedly in the polymer matrix, and thus it is considered that an onium salt formed of a combination of the cation in the general formula (2-1) and the anion in the general formula (2-2), that is a polymer including a repeating unit represented by the foregoing general formula (4), can exist. Therefore, a polymer including a repeating unit represented by the foregoing general formula (4) can be manufactured by copolymerizing a monomer represented by the foregoing general formula (2-1) and a monomer represented by the foregoing general formula (2-2). In addition, the exchanged onium salt may be removed by a cleansing operation using water after polymerization or the copolymer may also be a resist composition without a particular removal.

For the reason mentioned above, even if a polymer containing a repeating unit represented by the following general formula (2-1)' and a polymer containing a repeating unit represented by the following general formula (2-2)' are each prepared and thereafter blended with each other, a polymer including a repeating unit represented by the foregoing general formula (4) can also be obtained. Also in this case, the exchanged onium salt may be removed by a cleansing operation using water after polymerization or the copolymer may also be a resist composition without a particular removal.

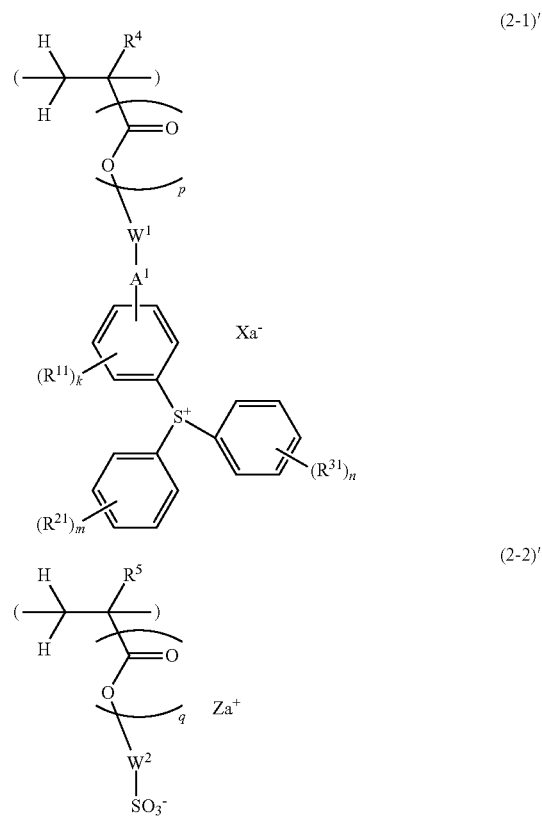

In addition, as preferable embodiment among polymers having a repeating unit represented by the foregoing general formula (4), a polymer having a repeating unit represented by the following general formula (5) is enumerated.

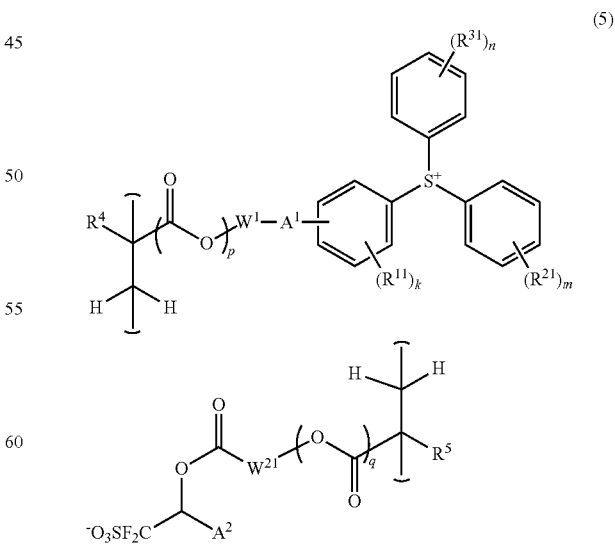

(In the formula, $W^{21}$ represents a single bond or a divalent hydrocarbon group having 1 to 30 carbon atoms optionally containing a hetero atom; $A^2$ represents a hydrogen atom or a trifluoromethyl group; and $W^1$, $A^1$, $R^{11}$, $R^{21}$, $R^{31}$, $R^4$, $R^5$, k, m, n, p and q represent the same as before.)

Further, the polymer of the present invention can include any one or more kinds of repeating units represented by the following general formulae (6) to (10) in addition to a repeating unit represented by the foregoing general formula (4), preferably a repeating unit represented by the foregoing general formula (5).

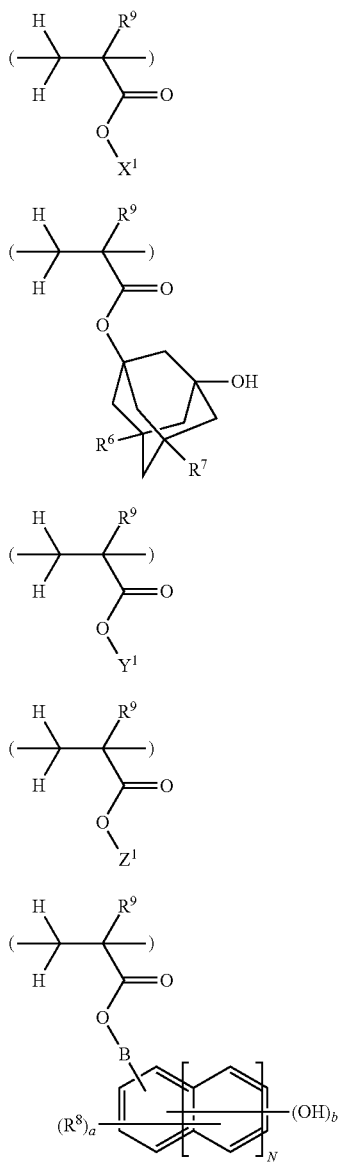

(In the formula, each $R^6$ and $R^7$ independently represents a hydrogen atom or a hydroxyl group; $R^8$ represents a hydrogen atom or an alkyl group having 1 to 10 carbon atoms; each $R^9$ independently represents a hydrogen atom, a fluorine atom, a methyl group or a trifluoromethyl group; $X^1$ represents an acid-labile group; $Y^1$ represents a substituent having a lactone structure; $Z^1$ represents a hydrogen atom, a fluoroalkyl group having 1 to 15 carbon atoms or a fluoroalcohol-containing substituent having 1 to 15 carbon atoms; N represents an integer of 0 to 2; B represents a single bond or a divalent organic group having 1 to 10 carbon atoms, which may be substituted by an oxygen atom; a represents an integer of 0 to 3; and b represents an integer of 1 to 3.)

A polymer including a repeating unit represented by the foregoing general formula (6) is decomposed by action of an acid to generate a carboxylic acid thereby giving an alkaline-soluble polymer. $X^1$ represents an acid-labile group.

Various groups can be used as the acid-labile group $X^1$. Specific examples of $X^1$ may include groups represented by any one of the following general formulae (L1) to (L4) and (L2-2), tertiary alkyl groups having 4-20, preferably 4-15 carbon atoms, trialkylsilyl groups whose each alkyl group has 1-6 carbon atoms, oxoalkyl groups having 4-20 carbon atoms and the like.

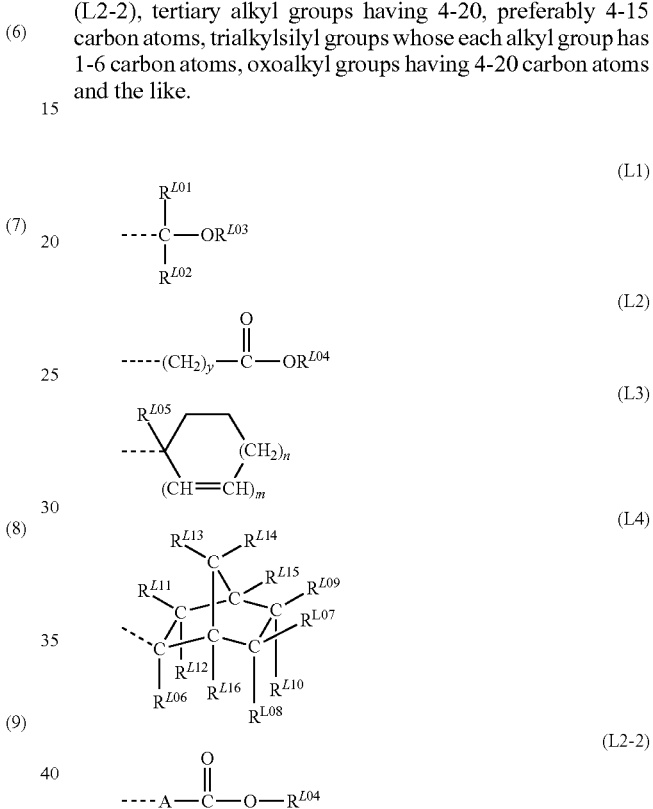

Here, the broken lines represent bonding hands (hereinafter same as this).

In addition, in the formula (L1), $R^{L01}$ and $R^{L02}$ represent a hydrogen atom, or a linear, a branched, or a cyclic alkyl group having 1 to 18, preferably 1 to 10 carbon atoms, specifically such as methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl and adamantyl. $R^{L03}$ represents a monovalent hydrocarbon group having 1 to 18, preferably 1 to 10 carbon atoms, optionally containing a hetero atom such as oxygen. A linear, a branched, or a cyclic alkyl group, and a group in which part of hydrogen atoms thereof is substituted with hydroxyl group, an alkoxy group, oxo group, amino group, an alkylamino group and the like are given, and specifically, following substituted alkyl groups and the like are exemplified.

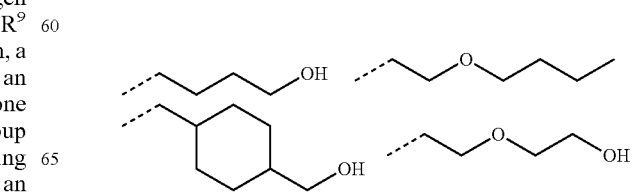

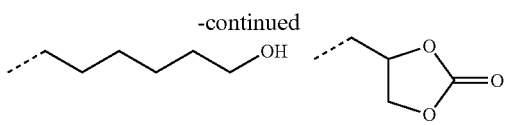

$R^{L01}$ and $R^{L02}$, $R^{L01}$ and $R^{L03}$, and $R^{L02}$ and $R^{L03}$ may be bonded with each other to form a ring together with a carbon atom or oxygen atom to which they are bonded. When they form a ring, each $R^{L01}$, $R^{L02}$ and $R^{L03}$ related to the ring formation represents a linear or a branched alkylene group having 1 to 18, preferably 1 to 10 carbon atoms.

In the formula (L2), $R^{L04}$ represents a tertiary alkyl group having 4 to 20, preferably 4 to 15 carbon atoms, a trialkylsilyl group whose each alkyl group has 1 to 6 carbon atoms, an oxoalkyl group having 4 to 20 carbon atoms, or the group represented by the foregoing general formula (L1). As the tertiary alkyl group, specifically, tert-butyl, tert-amyl, 1,1-diethylpropyl, 2-cyclopentylpropane-2-yl, 2-cyclohexylpropane-2-yl, 2-(bicyclo[2.2.1]heptane-2-yl)propane-2-yl, 2-(adamantane-1-yl)propane-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl and the like are exemplified. As the trialkylsilyl group, specifically, trimethylsilyl, triethylsilyl, dimethyl-tert-butylsilyl and the like are exemplified. As the oxoalkyl group, specifically, 3-oxocyclohexyl, 4-methyl-2-oxooxane-4-yl, 5-methyl-2-oxooxolane-5-yl and the like are exemplified. "y" represents an integer of 0 to 6.

In the formula (L2-2), A is the following groups, and $R^{L04}$ represents the same as before.

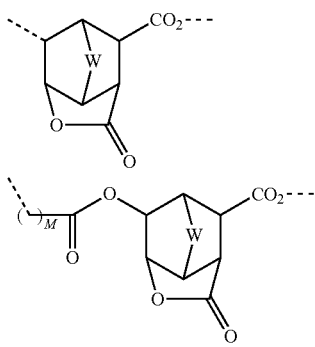

(In the formula, the broken lines represent bonding hands. W represents an oxygen atom or $CH_2$, and M represents an integer of 1 to 3.)

In the formula (L3), $R^{L05}$ represents a linear, a branched, or a cyclic alkyl group having 1 to 8 carbon atoms, optionally substituted, or an aryl group having 6 to 20 carbon atoms, optionally substituted. As the optionally substituted alkyl group, specifically, a linear, a branched or a cyclic alkyl group such as methyl, ethyl, propyl, isopropyl, n-butyl, sec-butyl, tert-butyl, tert-amyl, n-pentyl, n-hexyl, cyclopentyl, and cyclohexyl, and a group in which part of hydrogen atoms thereof is substituted with hydroxyl, alkoxy, carboxyl, alkoxycarbonyl, oxo, amino, alkylamino, cyano, mercapto, alkylthio, sulfo and the like are exemplified. As the optionally substituted aryl group, specifically, phenyl, methylphenyl, naphthyl, anthryl, phenanthryl, pyrenyl and the like are exemplified. "m" represents 0 or 1 and "n" is any of 0, 1, 2 or 3, which satisfy 2m+n=2 or 3.

In the formula (L4), $R^{L06}$ represents a linear, a branched, or a cyclic alkyl group having 1 to 8 carbon atoms, optionally substituted, or aryl group having 6 to 20 carbon atoms, optionally substituted, specifically the same as $R^{L05}$ and the like. Each $R^{L07}$ to $R^{L16}$ independently represents a hydrogen atom or a monovalent hydrocarbon group having 1 to 15 carbon atoms, specifically, a linear, a branched or a cyclic alkyl group such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, and cyclohexylbutyl, and a group in which part of hydrogen atoms thereof is substituted with hydroxyl, alkoxy, carboxyl, alkoxycarbonyl, oxo, amino, alkylamino, cyano, mercapto, alkylthio, sulfo and the like. Each two of $R^{L07}$ to $R^{L16}$ may be bonded with each other to form a ring together with a carbon atom to which they are bonded (for example, $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, etc.) In this case, a group which is related to the bond represents a divalent hydrocarbon group having 1 to 15 carbon atoms, specifically, a group that one hydrogen atom is removed from the above-mentioned examples of a monovalent hydrocarbon group and the like. In addition, each two of $R^{L07}$ to $R^{L16}$ in which carbon atoms to be bonded with them are located adjacently may be bonded without any groups between to form a double bond (for example, $R^{L07}$ and $R^{L09}$, $R^{L09}$ and $R^{L15}$, $R^{L13}$ and $R^{L15}$, etc.).

As linear or branched one among the acid-labile groups represented by the foregoing formula (L1), specifically following groups are exemplified.

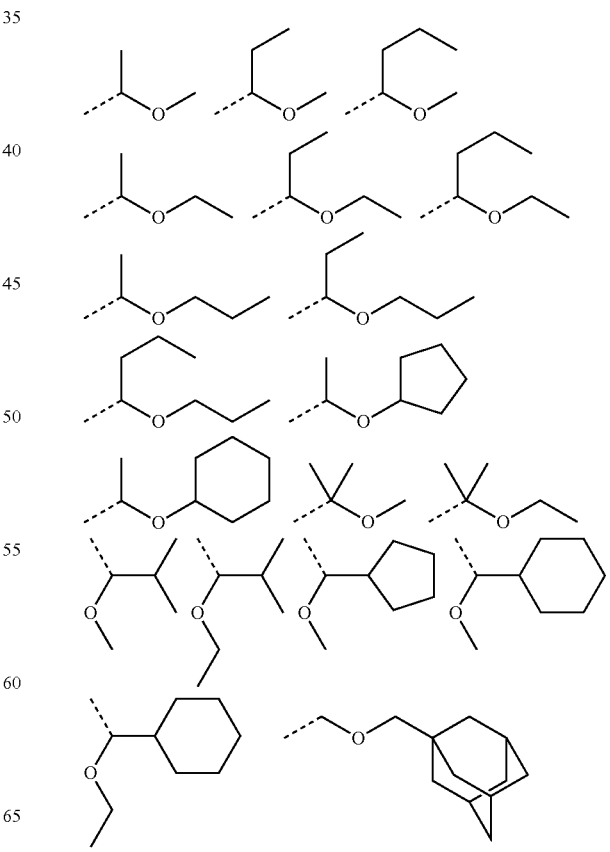

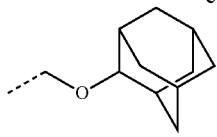

As cyclic one among the acid-labile groups represented by the foregoing formula (L1), specifically tetrahydrofuran-2-yl, 2-methyl tetrahydrofuran-2-yl, tetrahydropyran-2-yl, 2-methyltetrahydropyran-2-yl and the like are exemplified.

As the acid-labile group of the foregoing formula (L2), specifically tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, 2-tetrahydrofuranyloxycarbonylmethyl and the like are exemplified.

As the acid-labile group of the foregoing formula (L2-2), specifically 9-(tert-butyloxycarbonyl)-5-oxo-4-oxatricyclo[4.2.1.0$^{3,7}$]nonane-2-yl, 9-(tert-amyloxycarbonyl)-5-oxo-4-oxatricyclo[4.2.1.0$^{3,7}$]nonane-2-yl, 9-(2-(adamantane-1-yl)propane-2-yloxycarbonyl)-5-oxo-4-oxatricyclo[4.2.1.0$^{3,7}$]nonane-2-yl, 9-(1-ethylcyclopentyloxycarbonyl)-5-oxo-4-oxatricyclo[4.2.1.0$^{3,7}$]nonane-2-yl, 9-(1-butylcyclopentyloxycarbonyl)-5-oxo-4-oxatricyclo[4.2.1.0$^{3,7}$]nonane-2-yl, 9-(1-ethylcyclohexyloxycarbonyl)-5-oxo-4-oxatricyclo[4.2.1.0$^{3,7}$]nonane-2-yl, 9-(1-butylcyclohexyloxycarbonyl)-5-oxo-4-oxatricyclo[4.2.1.0$^{3,7}$]nonane-2-yl, 9-(2-methyl-2-adamantyloxycarbonyl)-5-oxo-4-oxatricyclo[4.2.1.0$^{3,7}$]nonane-2-yl, 9-(2-ethyl-2-adamantyloxycarbonyl)-5-oxo-4-oxatricyclo[4.2.1.0$^{3,7}$]nonane-2-yl, 9-(4-ethyltetracyclo[6.2.1.1$^{3,6}$.0$^{2,7}$]dodecane-4-yloxycarbonyl)-5-oxo-4-oxatricyclo[4.2.1.0$^{3,7}$]nonane-2-yl, 2-(9-(tert-butyloxycarbonyl)-5-oxo-4-oxatricyclo[4.2.1.0$^{3,7}$]nonane-2-yloxy)-2-oxoethyl, 2-(9-(tert-amyloxycarbonyl)-5-oxo-4-oxatricyclo[4.2.1.0$^{3,7}$]nonane-2-yloxy)-2-oxoethyl, 2-(9-(2-(adamantane-1-yl)propane-2-yloxycarbonyl)-5-oxo-4-oxatricyclo[4.2.1.0$^{3,7}$]nonane-2-yloxy)-2-oxoethyl, 2-(9-(1-ethylcyclopentyloxycarbonyl)-5-oxo-4-oxatricyclo[4.2.1.0$^{3,7}$]nonane-2-yloxy)-2-oxoethyl, 2-(9-(1-butylcyclopentyloxycarbonyl)-5-oxo-4-oxatricyclo[4.2.1.0$^{3,7}$]nonane-2-yloxy)-2-oxoethyl, 2-(9-(1-ethylcyclohexyloxycarbonyl)-5-oxo-4-oxatricyclo[4.2.1.0$^{3,7}$]nonane-2-yloxy)-2-oxoethyl, 2-(9-(1-butylcyclohexyloxycarbonyl)-5-oxo-4-oxatricyclo[4.2.1.0$^{3,7}$]nonane-2-yloxy)-2-oxoethyl, 2-(9-(2-methyl-2-adamantyloxycarbonyl)-5-oxo-4-oxatricyclo[4.2.1.0$^{3,7}$]nonane-2-yloxy)-2-oxoethyl, 2-(9-(2-ethyl-2-adamantyloxycarbonyl)-5-oxo-4-oxatricyclo[4.2.1.0$^{3,7}$]nonane-2-yloxy)-2-oxoethyl, 2-(9-(4-ethyltetracyclo[6.2.1.1$^{3,6}$.0$^{2,7}$]dodecane-4-yloxycarbonyl)-5-oxo-4-oxatricyclo[4.2.1.0$^{3,7}$]nonane-2-yloxy)-2-oxoethyl, 4-(9-(tert-butyloxycarbonyl)-5-oxo-4-oxatricyclo[4.2.1.0$^{3,7}$]nonane-2-yloxy)-4-oxobutyl, 4-(9-(tert-amyloxycarbonyl)-5-oxo-4-oxatricyclo[4.2.1.0$^{3,7}$]nonane-2-yloxy)-4-oxobutyl, 4-(9-(2-(adamantane-1-yl)propane-2-yloxycarbonyl)-5-oxo-4-oxatricyclo[4.2.1.0$^{3,7}$]nonane-2-yloxy)-4-oxobutyl, 4-(9-(1-ethylcyclopentyloxycarbonyl)-5-oxo-4-oxatricyclo[4.2.1.0$^{3,7}$]nonane-2-yloxy)-4-oxobutyl, 4-(9-(1-butylcyclopentyloxycarbonyl)-5-oxo-4-oxatricyclo[4.2.1.0$^{3,7}$]nonane-2-yloxy)-4-oxobutyl, 4-(9-(1-ethylcyclohexyloxycarbonyl)-5-oxo-4-oxatricyclo[4.2.1.0$^{3,7}$]nonane-2-yloxy)-4-oxobutyl, 4-(9-(1-butylcyclohexyloxycarbonyl)-5-oxo-4-oxatricyclo[4.2.1.0$^{3,7}$]nonane-2-yloxy)-4-oxobutyl, 4-(9-(2-methyl-2-adamantyloxycarbonyl)-5-oxo-4-oxatricyclo[4.2.1.0$^{3,7}$]nonane-2-yloxy)-4-oxobutyl, 4-(9-(2-ethyl-2-adamantyloxycarbonyl)-5-oxo-4-oxatricyclo[4.2.1.0$^{3,7}$]nonane-2-yloxy)-4-oxobutyl, 4-(9-(4-ethyltetracyclo[6.2.1.1$^{3,6}$.0$^{2,7}$]dodecane-4-yloxycarbonyl)-5-oxo-4-oxatricyclo[4.2.1.0$^{3,7}$]nonane-2-yloxy)-4-oxobutyl and the like are exemplified.

As the acid-labile group of the foregoing formula (L3), specifically 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopentene-3-yl, 3-ethyl-1-cyclopentene-3-yl, 3-methyl-1-cyclohexene-3-yl, 3-ethyl-1-cyclohexene-3-yl and the like are exemplified.

As the acid-labile group of the foregoing formula (L4), groups represented by the following formulae (L4-1) to (L4-4) are particularly preferable.

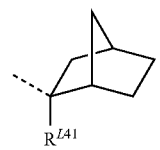

(L4-1)

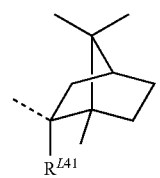

(L4-2)

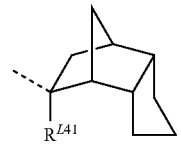

(L4-3)

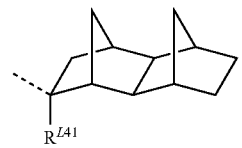

(L4-4)

In the above-mentioned general formulae (L4-1) to (L4-4), the broken lines represent bonding positions and bonding directions. Each $R^{L41}$ independently represents a monovalent hydrocarbon group such as a linear, a branched, or a cyclic alkyl group having 1 to 10 carbon atoms, and specifically methyl, ethyl, propyl, isopropyl, n-butyl, sec-butyl, tert-butyl, tert-amyl, n-pentyl, n-hexyl, cyclopentyl, cyclohexyl and the like can be exemplified.

There are possibilities of presence of an enantiomer and a diastereomer in the above-mentioned general formulae (L4-1) to (L4-4). The above-mentioned general formulae (L4-1) to (L4-4) represent all of these stereoisomers. These stereoisomers may be used solely or as a mixture of them.

For example, the above-mentioned general formula (L4-3) is to represent one kind or a mixture of two kinds selected from the groups represented by the following general formulae (L4-3-1) and (L4-3-2).

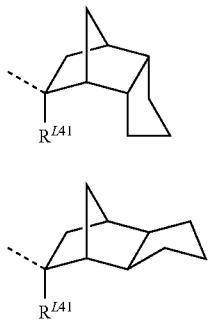
(L4-3-1)

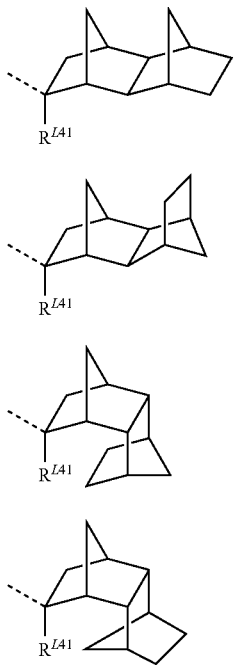
(L4-3-2)

In addition, the foregoing formula (L4-4) is to represent one kind or a mixture of two or more kinds selected from groups represented the following general formulae (L4-4-1) to (L4-4-4).

(L4-4-1)

(L4-4-2)

(L4-4-3)

(L4-4-4)

The foregoing general formulae (L4-1) to (L4-4), (L4-3-1), (L4-3-2), and (L4-4-1) to (L4-4-4) are to also represent all of these enantiomers and a mixture of the enantiomers.

Meanwhile, a high reactivity in the acid-catalyzed elimination reaction is realized when each of the bonding directions of (L4-1) to (L4-4), (L4-3-1), (L4-3-2), and (L4-4-1) to (L4-4-4) is to the exo-position of the bicyclo[2.2.1]heptane ring (see Japanese Patent Laid-Open (kokai) No. 2000-336121). In the preparation of a monomer containing a tertiary exo-alkyl group having these bicyclo[2.2.1]heptane skeletons as a substituent, there is a case to include a monomer that is substituted with an endo-alkyl group represented by the following general formulae (L4-1-endo) to (L4-4-endo). In such a case, to accomplish a good reactivity, the exo-ratio is preferably 50% or more by mole, or more preferably 80% or more by mole.

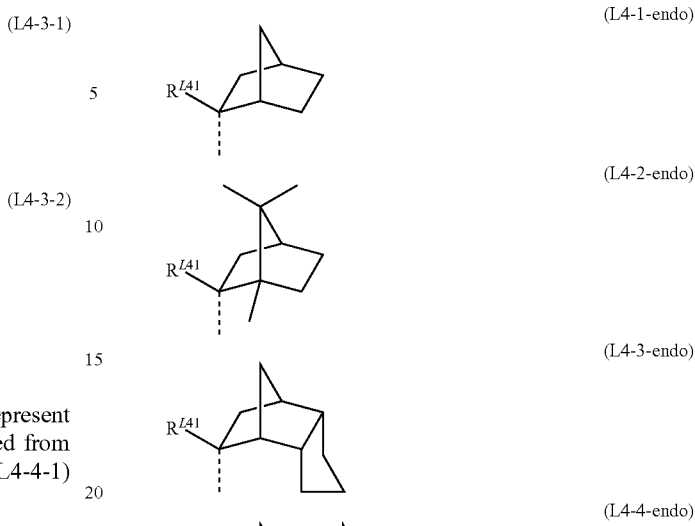
(L4-1-endo)
(L4-2-endo)
(L4-3-endo)
(L4-4-endo)

(See Japanese Patent Laid-Open (kokai) No. 2000-336121.)

As the acid-labile group of the foregoing formula (L4), specifically the following groups are exemplified.

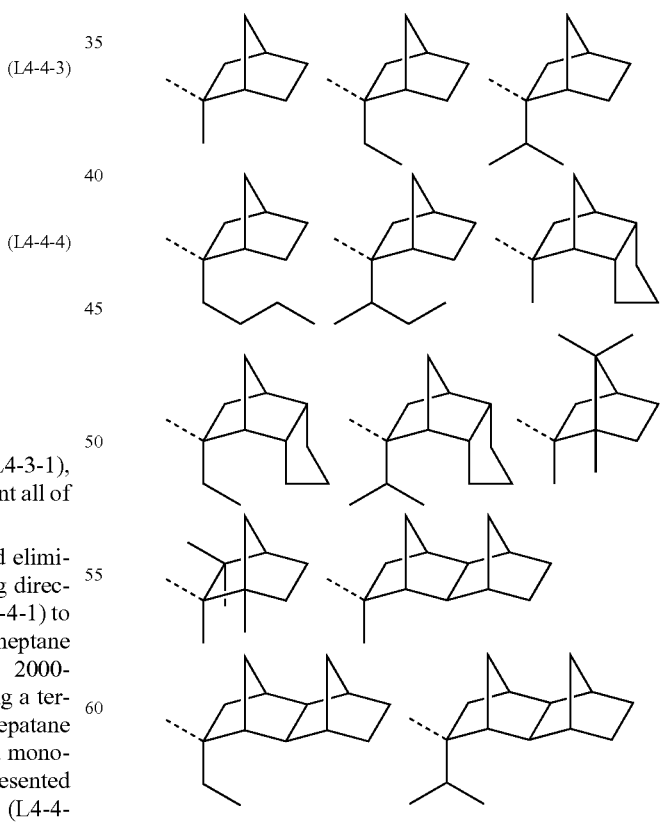

In addition, as a tertiary alkyl group having 4 to 20 carbon atoms, a trialkylsilyl group whose each alkyl group has 1 to 6 carbon atoms, and an oxoalkyl group having 4 to 20 carbon atoms, specifically the same as $R^{L04}$ and the like are exemplified.

Specifically, a repeating unit represented by the above-mentioned general formula (6) is exemplified by the following, but is not limited thereto. Although only a (meth)acrylic acid ester is shown, the one intervened by a divalent connector represented by the foregoing formula (L-2) or (L-2-2) may also be used.

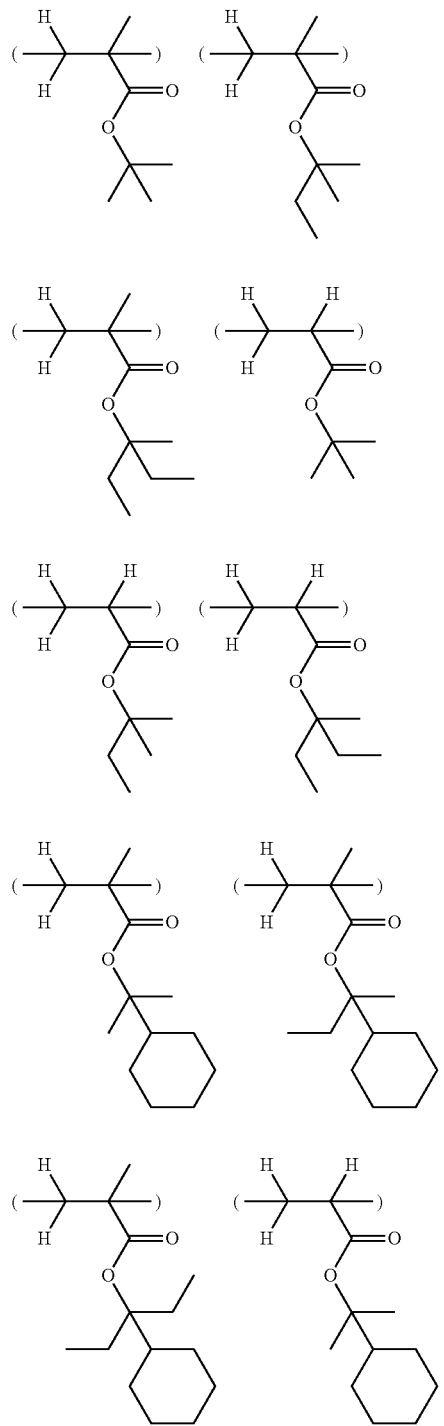
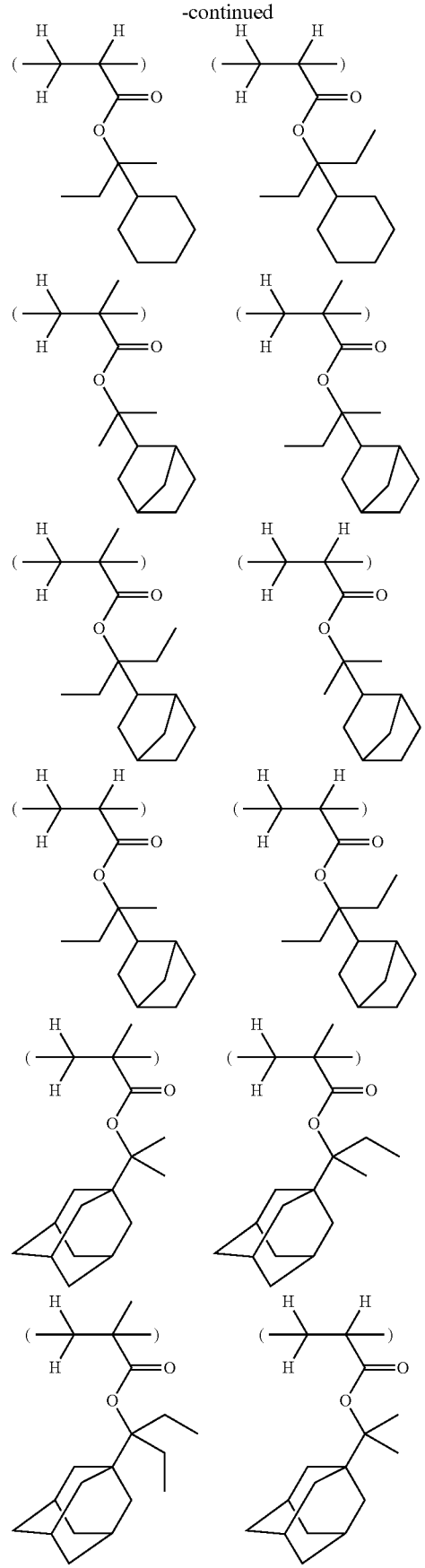

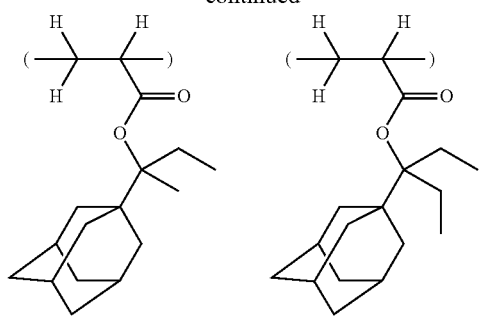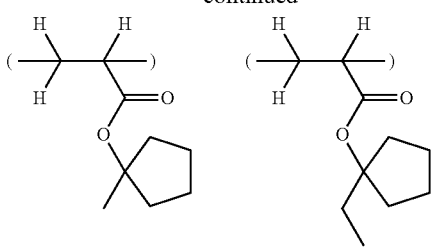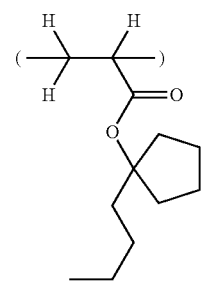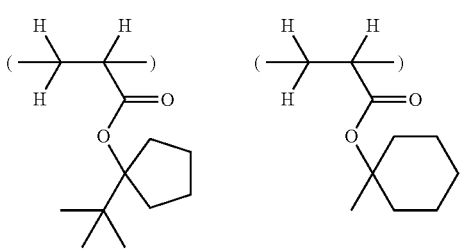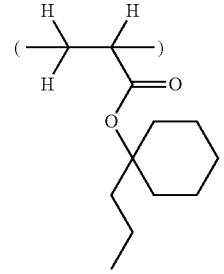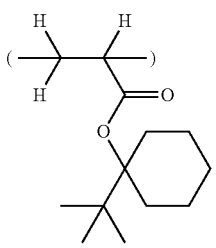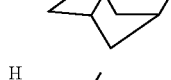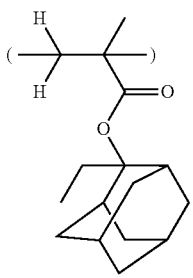

-continued
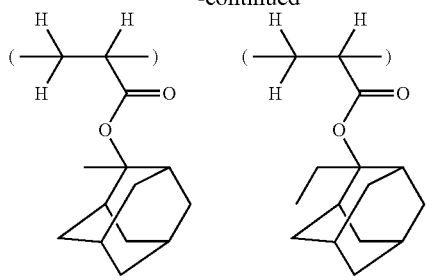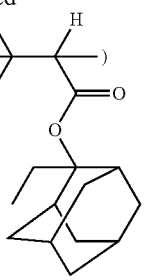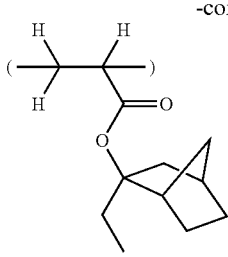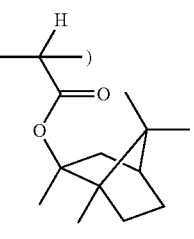
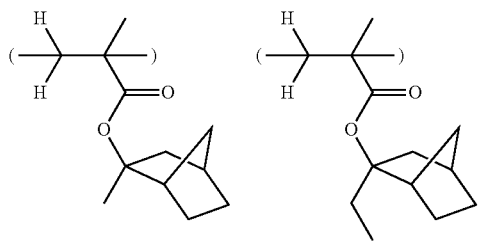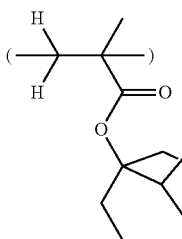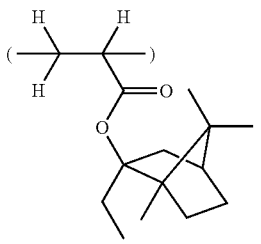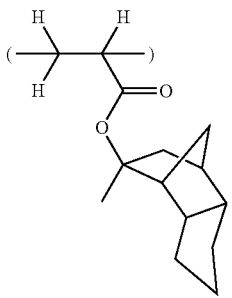
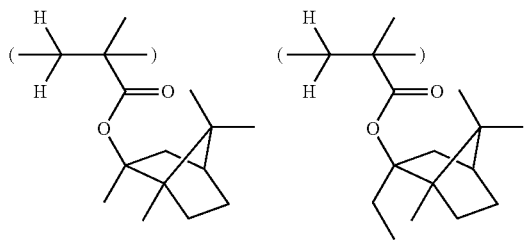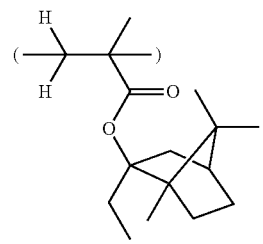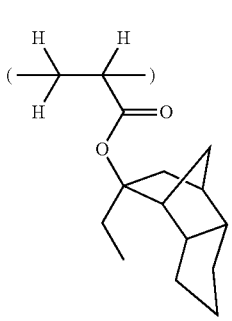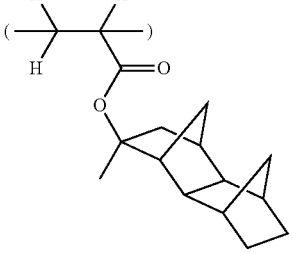
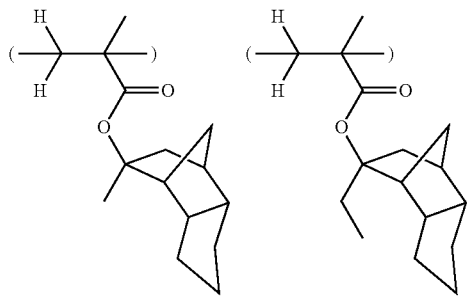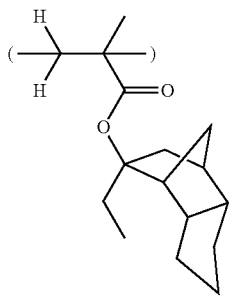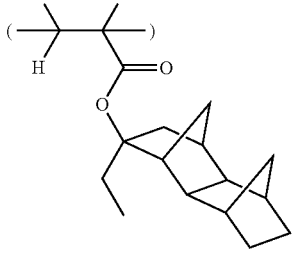
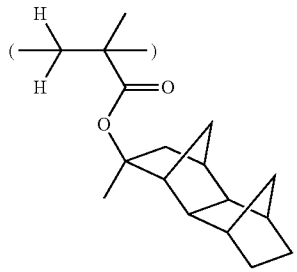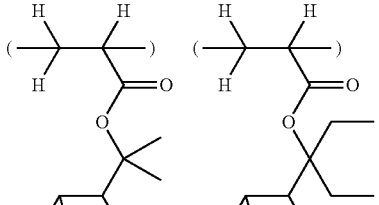
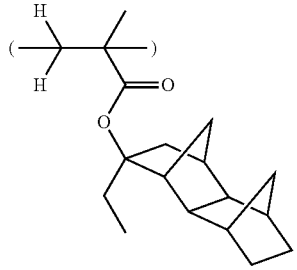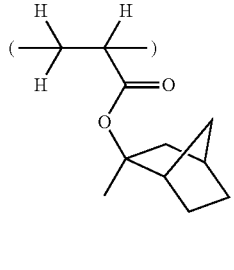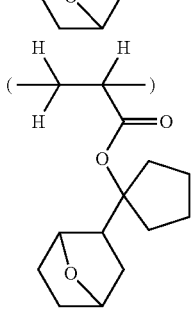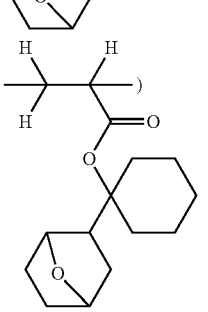

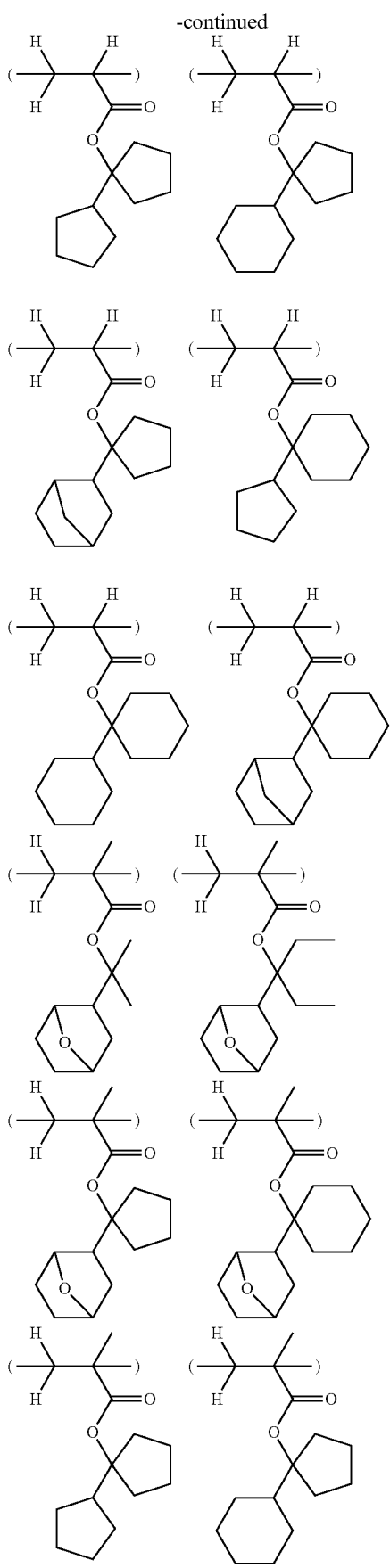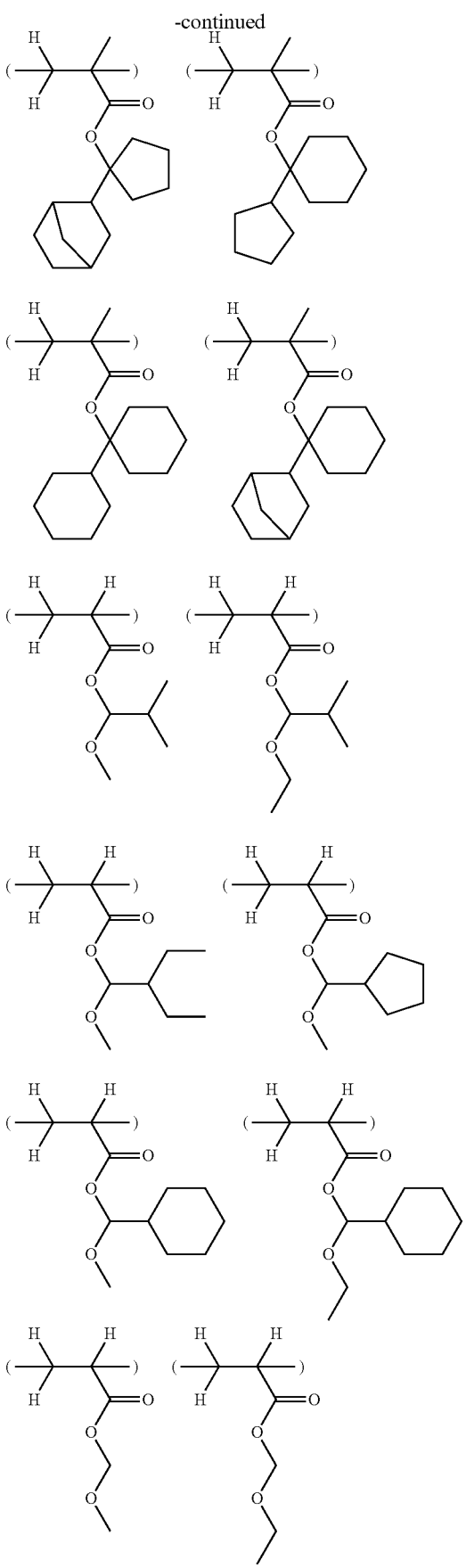

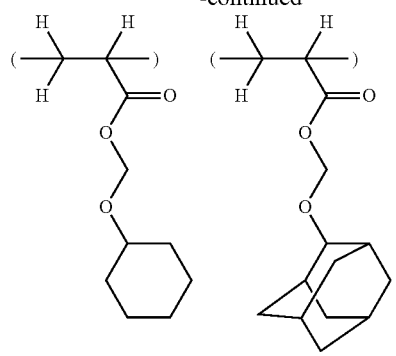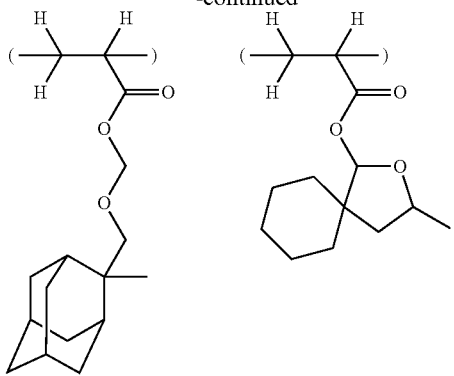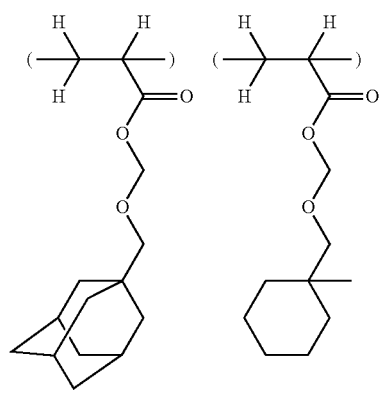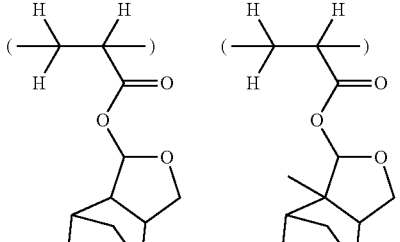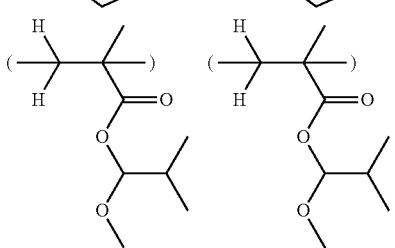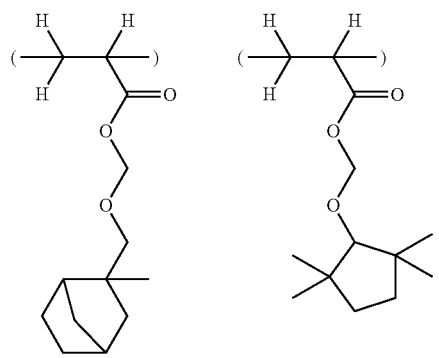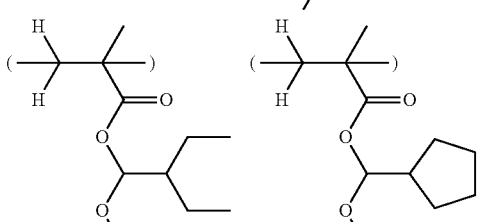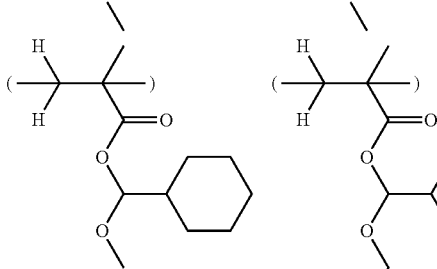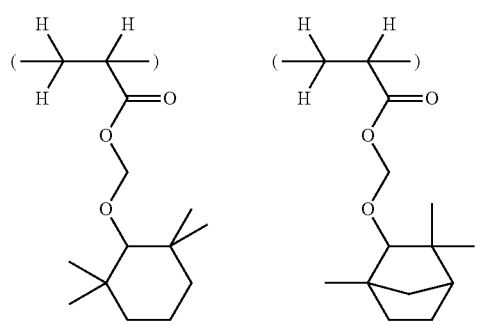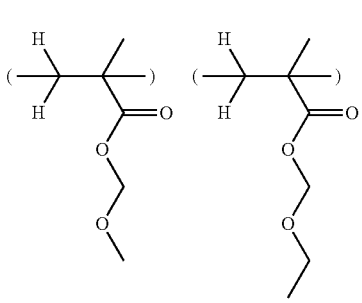

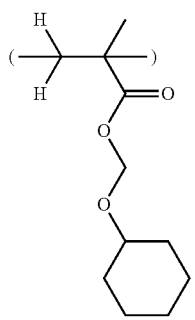
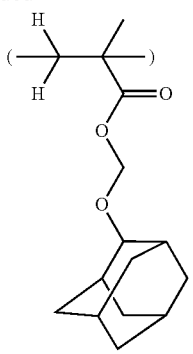
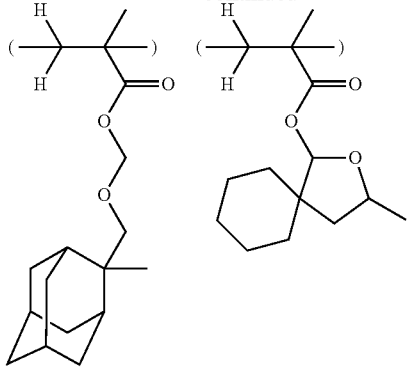
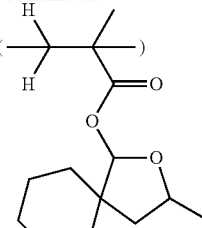
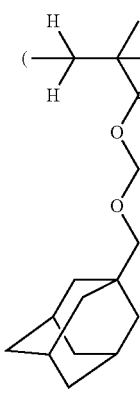
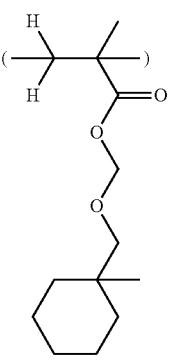
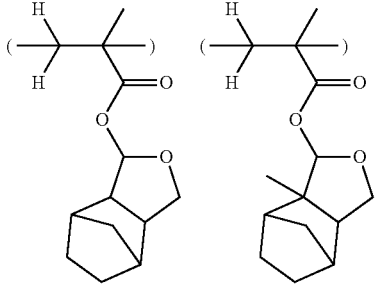
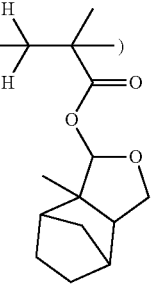
A repeating unit represented by the above-mentioned general formula (7) is specifically the following.
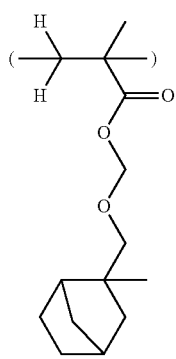
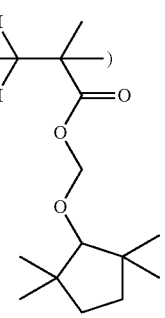
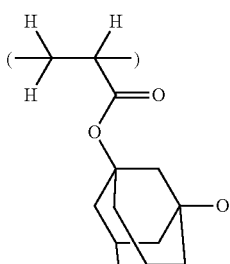
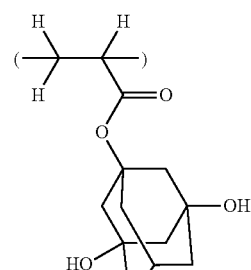
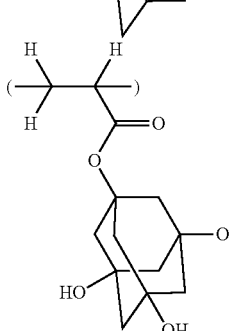
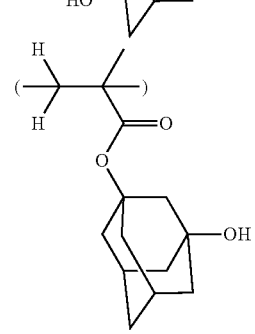
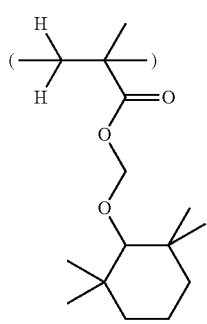
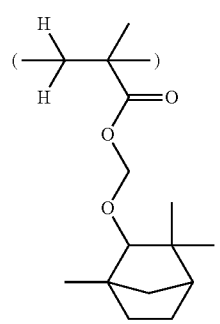
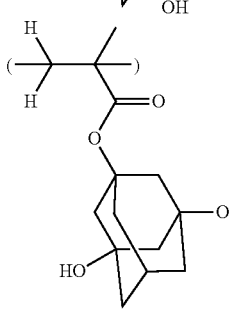
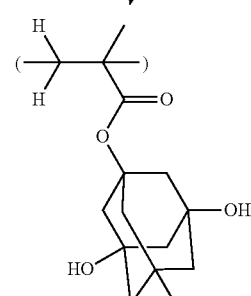

A repeating unit represented by the above-mentioned general formula (8) is specifically the following. Meanwhile, there can be a repeating unit having an acid-labile group. Specifically, the following are overlapped with the formula (L2-2) explained as the acid labile group, and may be used as a lactone unit or a unit having an acid labile group.
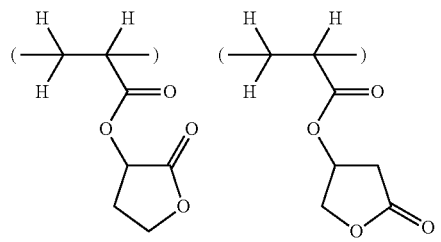
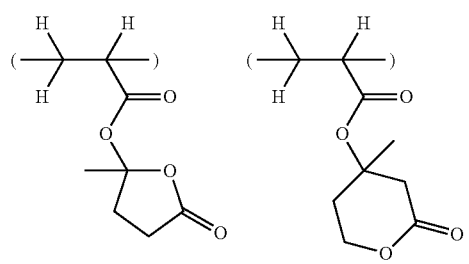
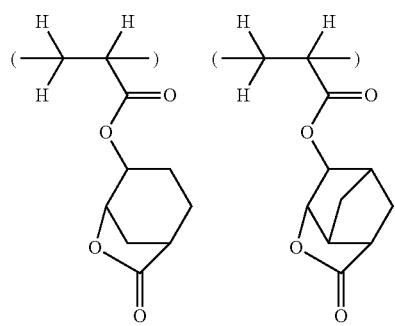
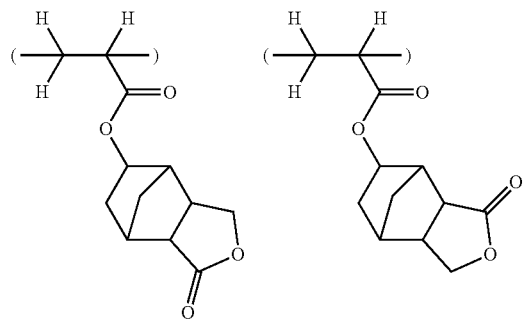
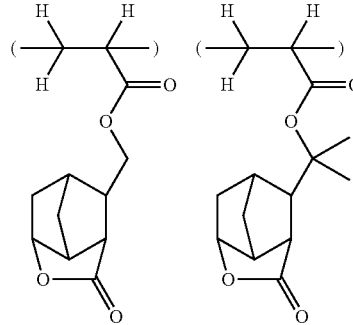
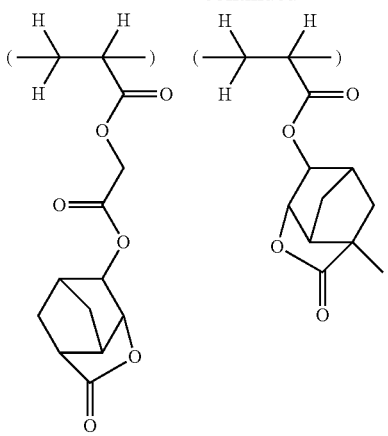
-continued
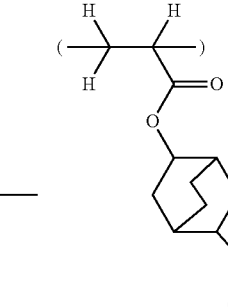
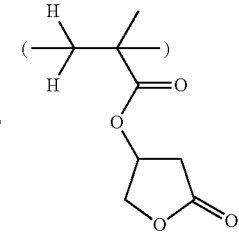
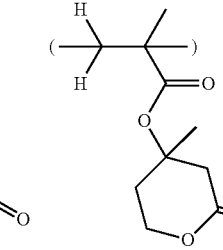
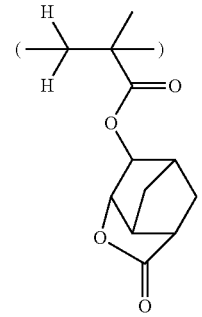
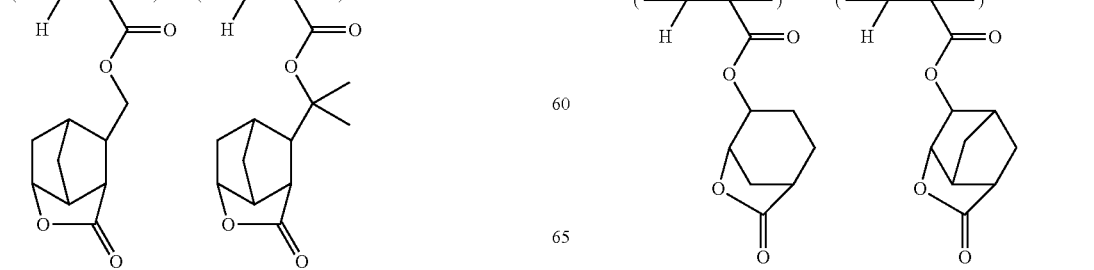

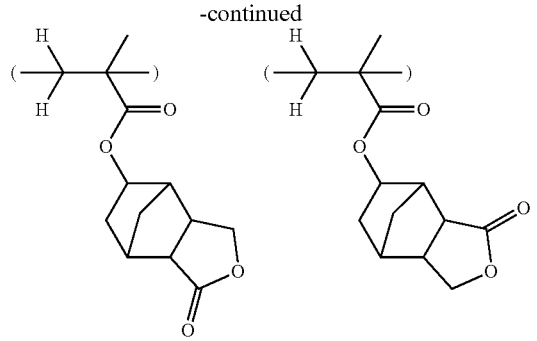
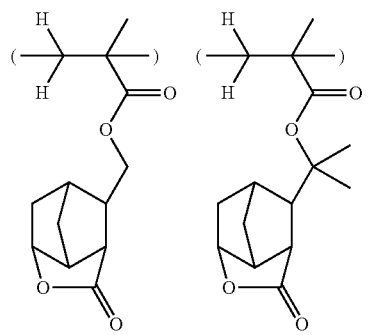
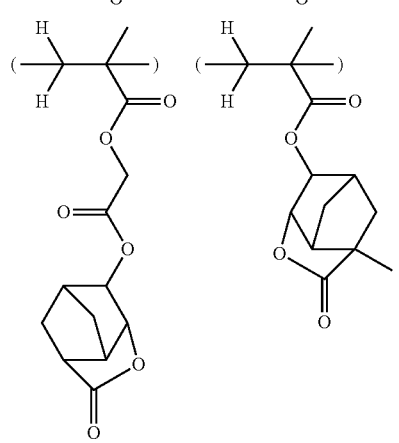
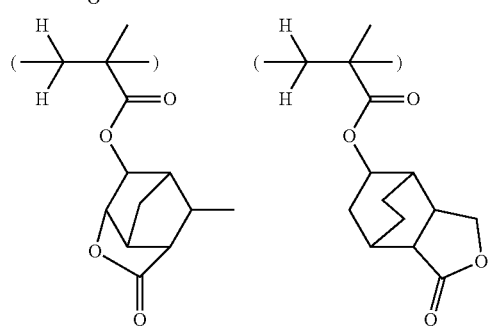
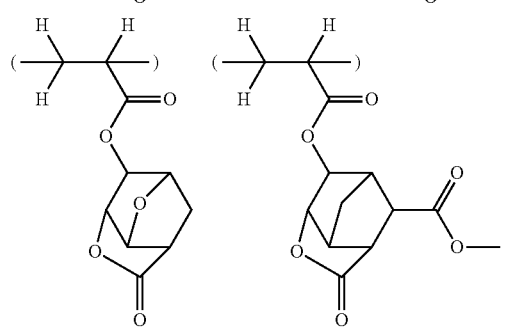
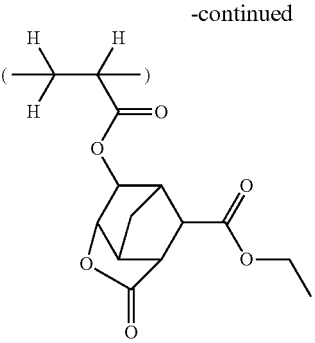
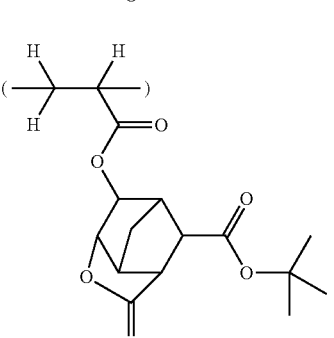
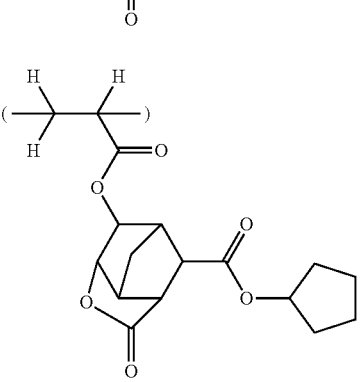
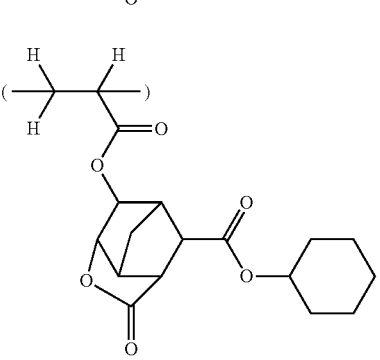
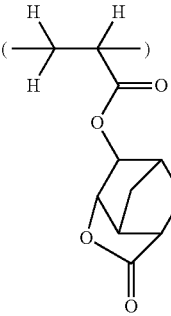

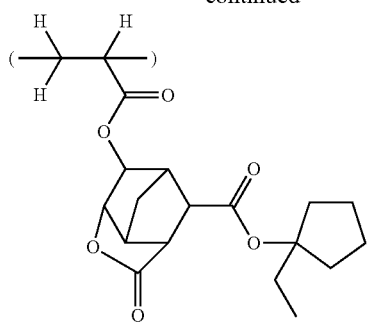
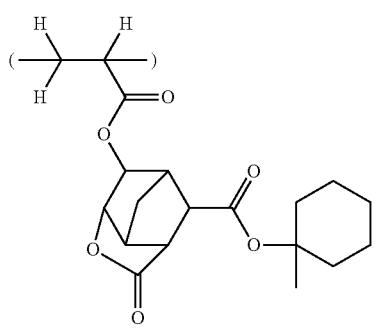
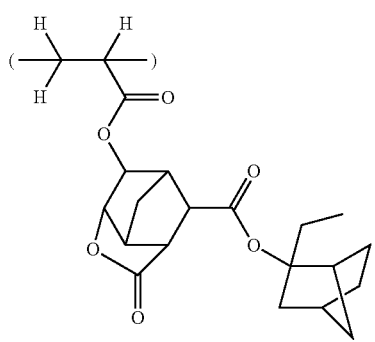
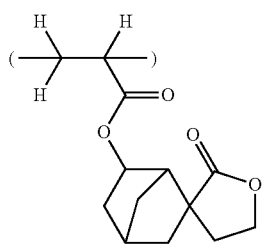
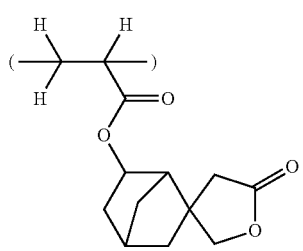
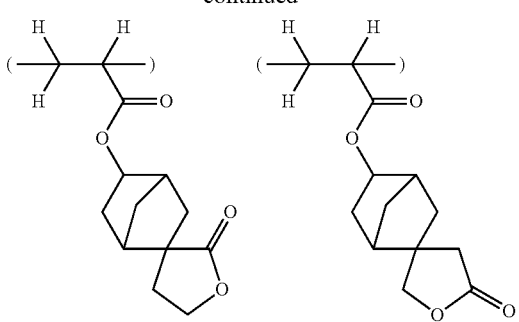
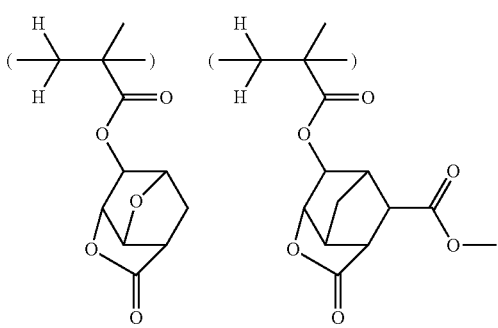
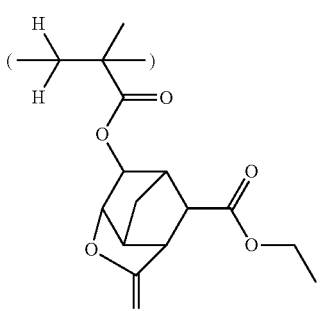
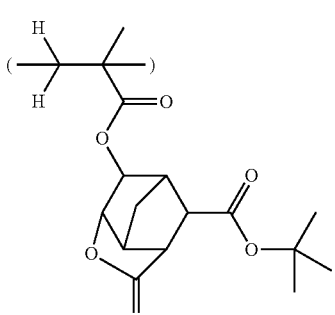
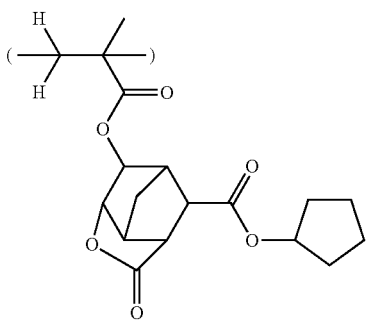

-continued

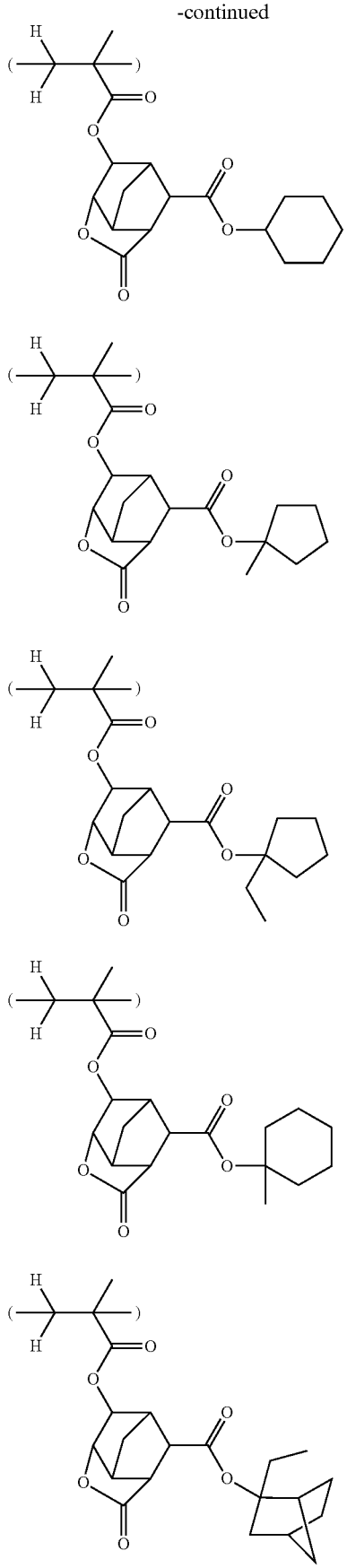

-continued

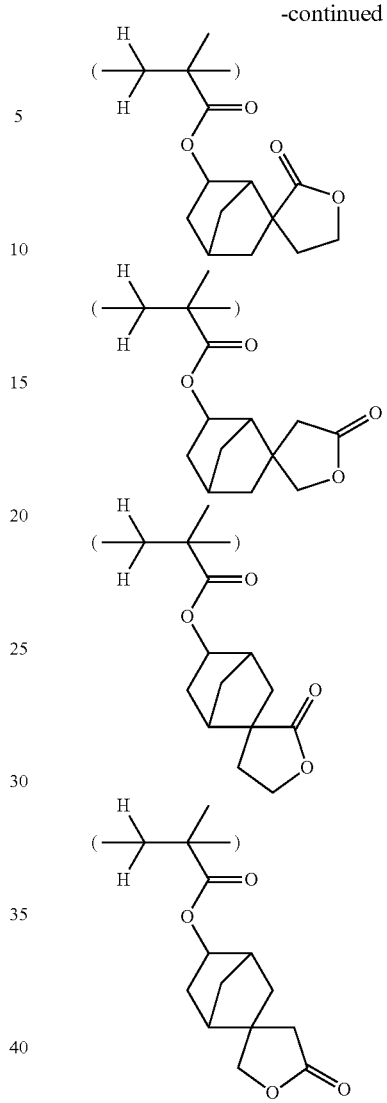

In addition, one represented by the following general formula (5L-1) can also be used preferably.

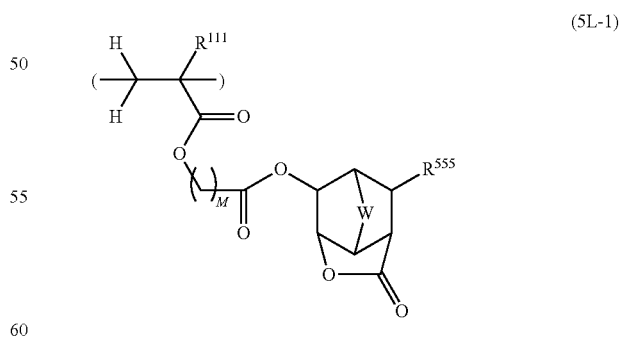

(5L-1)

Here, $R^{111}$ in the foregoing general formula (5L-1) represents a hydrogen atom, a fluorine atom, a methyl group or a trifluoromethyl group. More preferable is a methyl group. $R^{555}$ represents a hydrogen atom or $CO_2R^{555'}$. $R^{555'}$ represents a hydrogen atom, a linear, a branched, or a cyclic monovalent hydrocarbon group having 1 to 15 carbon atoms, optionally containing a halogen atom or an oxygen atom. W represents $CH_2$, O or S. M represents an integer of 1 to 3.

As $R^{555'}$, specifically hydrogen, methyl, ethyl, n-propyl, isopropyl, n-butyl, sec-butyl, isobutyl, tert-butyl, cyclopentyl, cyclohexyl, 1-methylcyclopentyl, 1-ethylcyclopentyl, 1-methylcyclohexyl, 1-ethylcyclohexyl, 2-ethylhexyl, n-octyl, 2-methylbicyclo[2.2.1]heptane-2-yl, 2-ethylbicyclo[2.2.1]heptane-2-yl, 2-methyladamantane-2-yl, 2-ethyladamantane-2-yl methyltricyclo[5.2.1.0$^{2,6}$]decane-8-yl, 8-ethyltricyclo[5.2.1.0$^{2,6}$]decane-8-yl, 4-methyltetracyclo[6.2.1.1$^{3,6}$.0$^{2,7}$]dodecane-4-yl, 4-ethyltetracyclo[6.2.1.1$^{3,6}$.0$^{2,7}$]dodecane-4-yl, methoxymethyl, ethoxymethyl, methoxyethyl, ethoxyethyl, methoxyethoxyethyl and the following groups, etc. are exemplified.

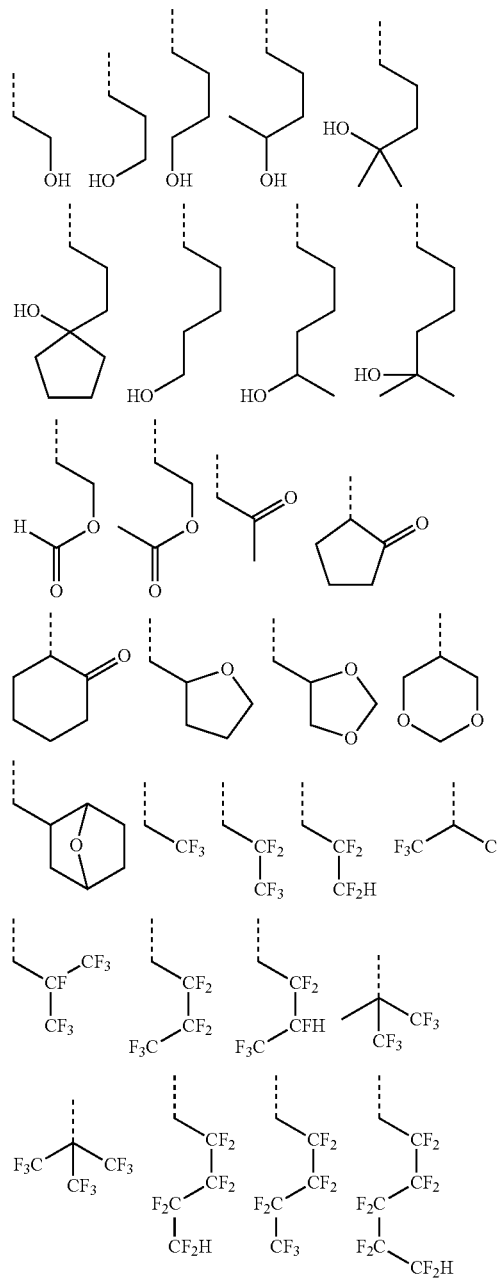

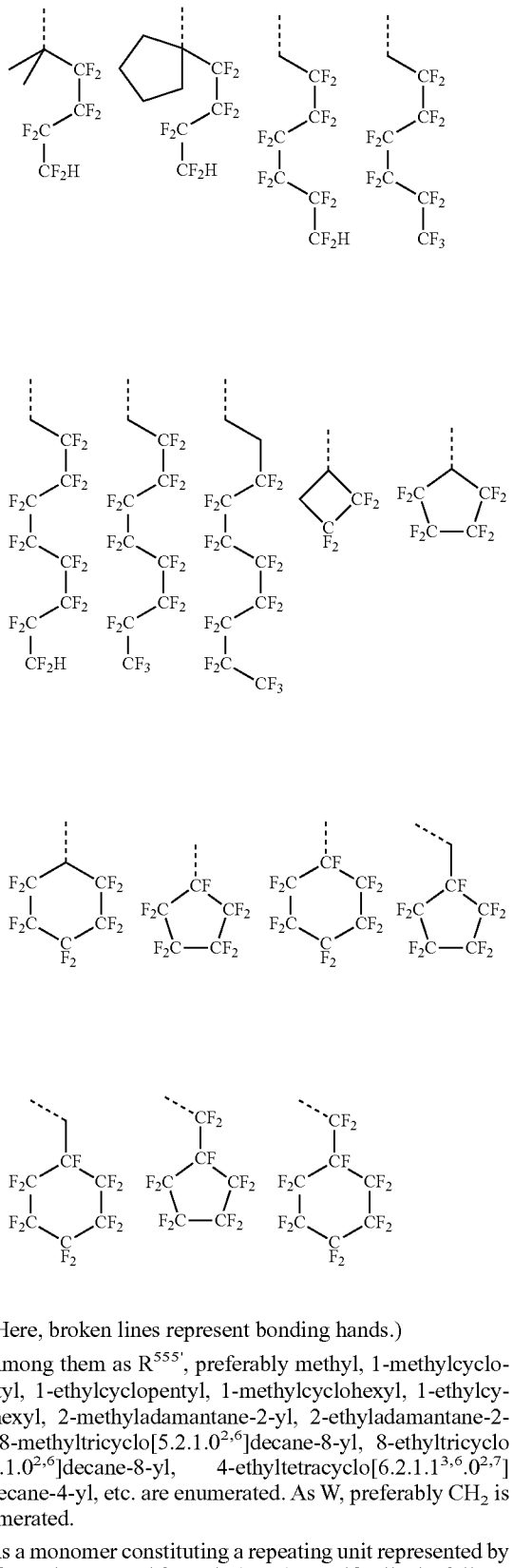

(Here, broken lines represent bonding hands.)

Among them as $R^{555'}$, preferably methyl, 1-methylcyclopentyl, 1-ethylcyclopentyl, 1-methylcyclohexyl, 1-ethylcyclohexyl, 2-methyladamantane-2-yl, 2-ethyladamantane-2-yl, 8-methyltricyclo[5.2.1.0$^{2,6}$]decane-8-yl, 8-ethyltricyclo[5.2.1.0$^{2,6}$]decane-8-yl, 4-ethyltetracyclo[6.2.1.1$^{3,6}$.0$^{2,7}$]dodecane-4-yl, etc. are enumerated. As W, preferably $CH_2$ is enumerated.

As a monomer constituting a repeating unit represented by the foregoing general formula (5L-1), specifically the following are exemplified.

-continued
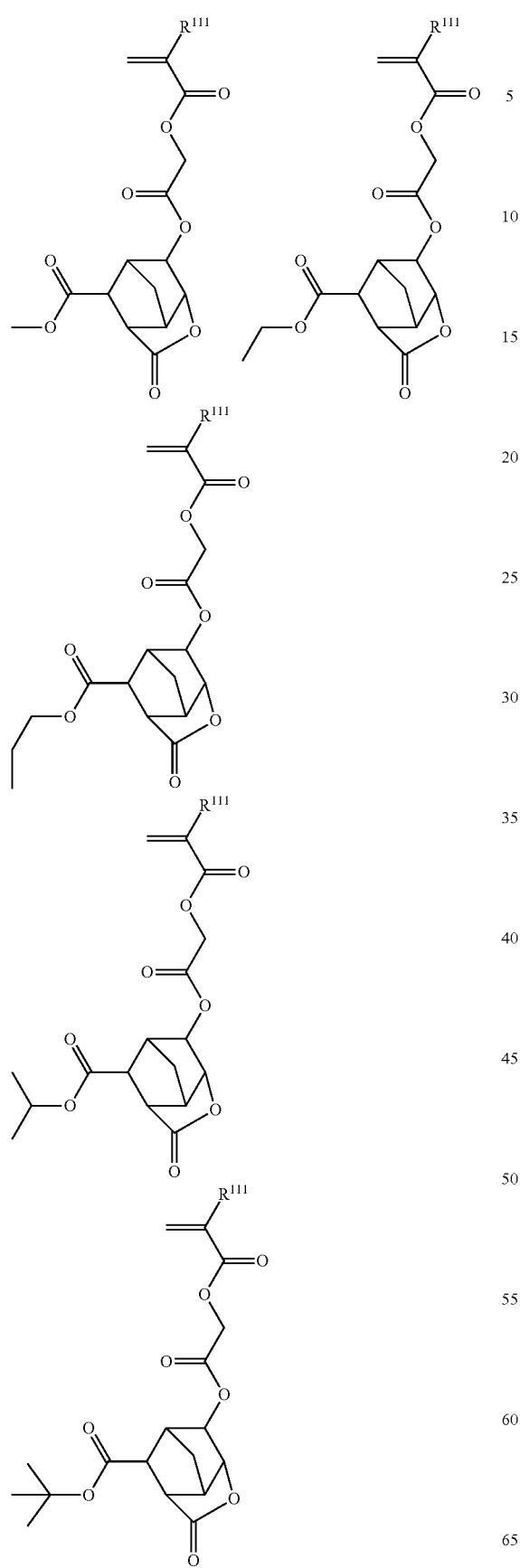
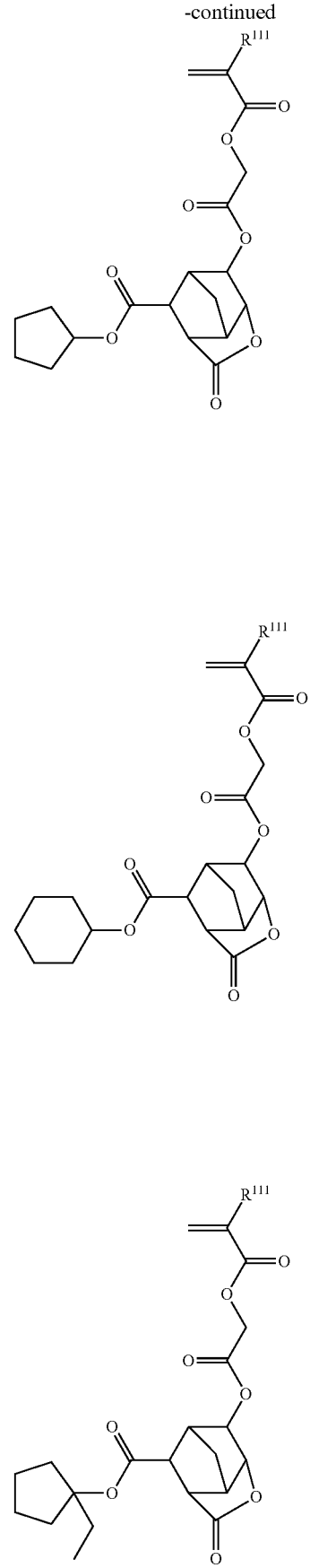

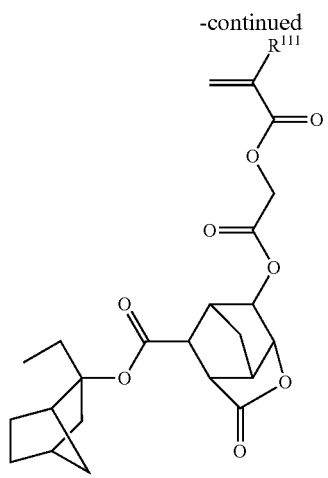
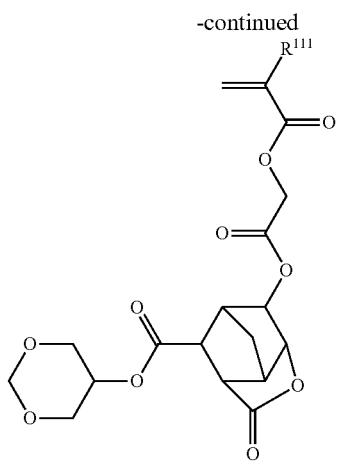
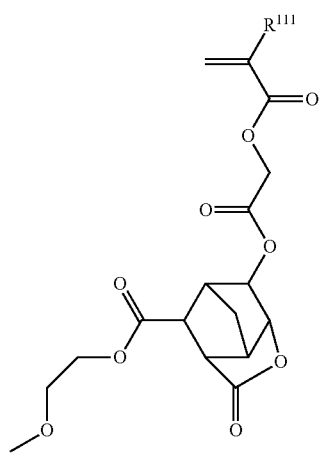
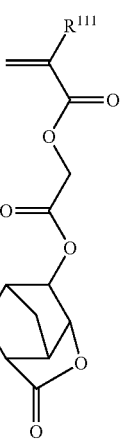
(In the formula, $R^{111}$ represents the same as before.)
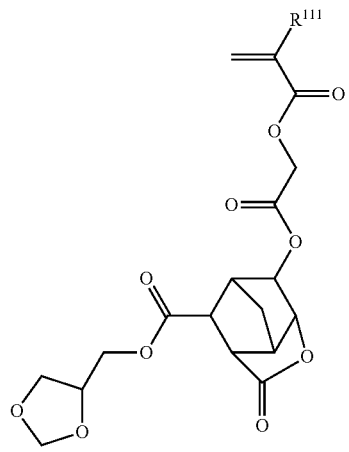
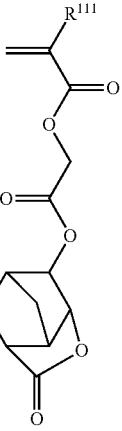

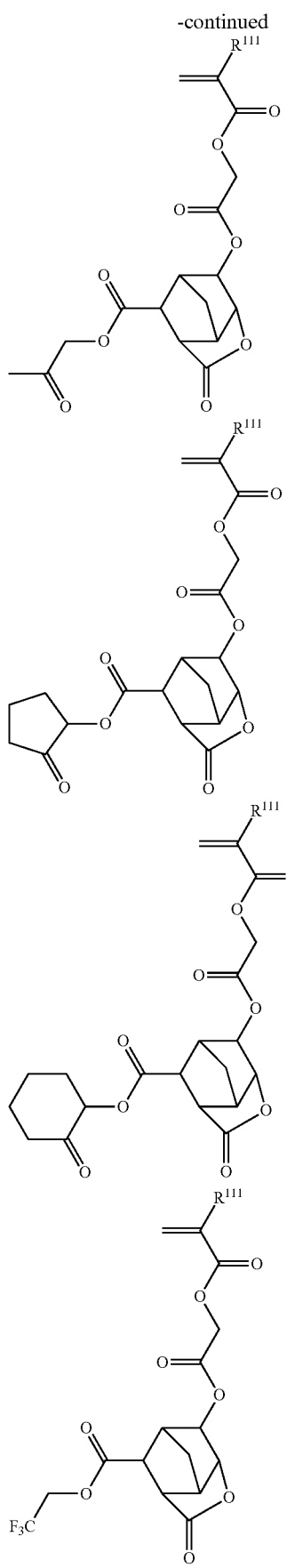

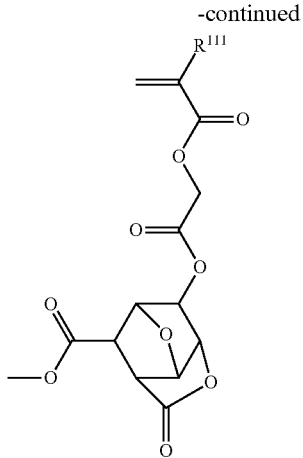
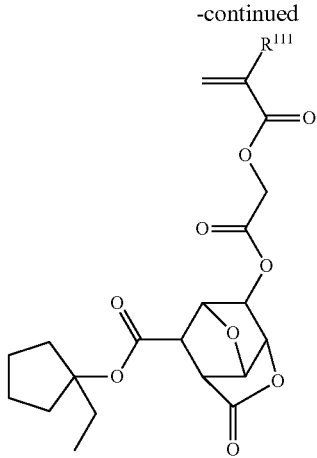
(In the formula, R$^{111}$ represents the same as before.)
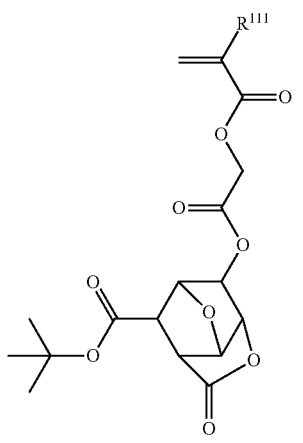
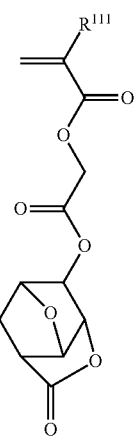
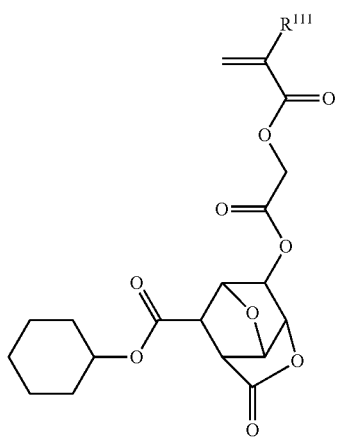
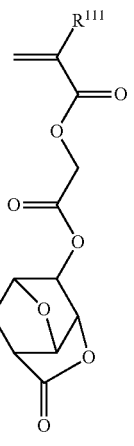

-continued
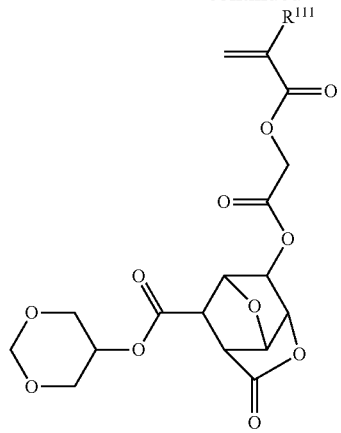
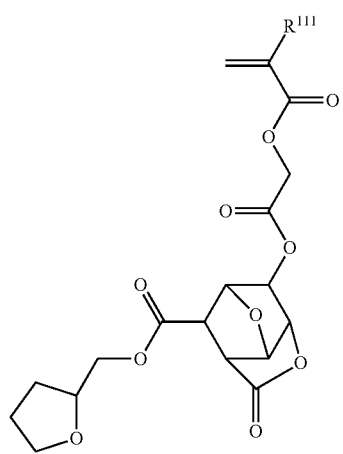
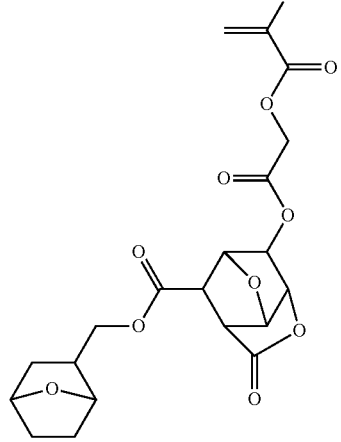
-continued
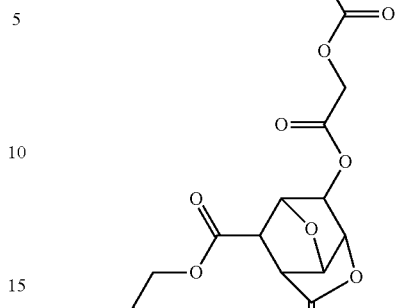
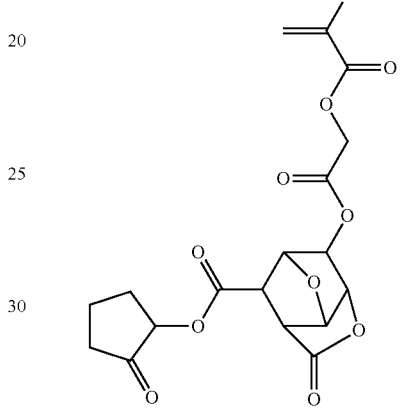
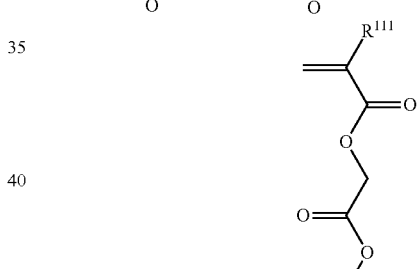
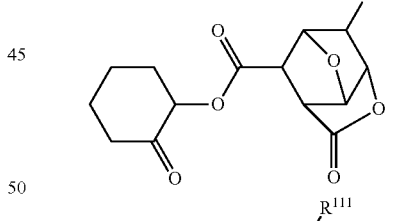
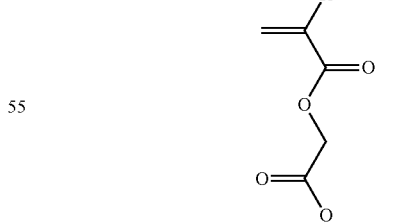
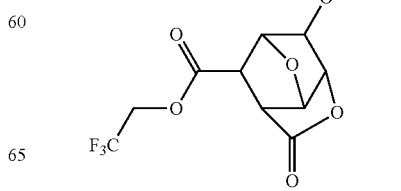

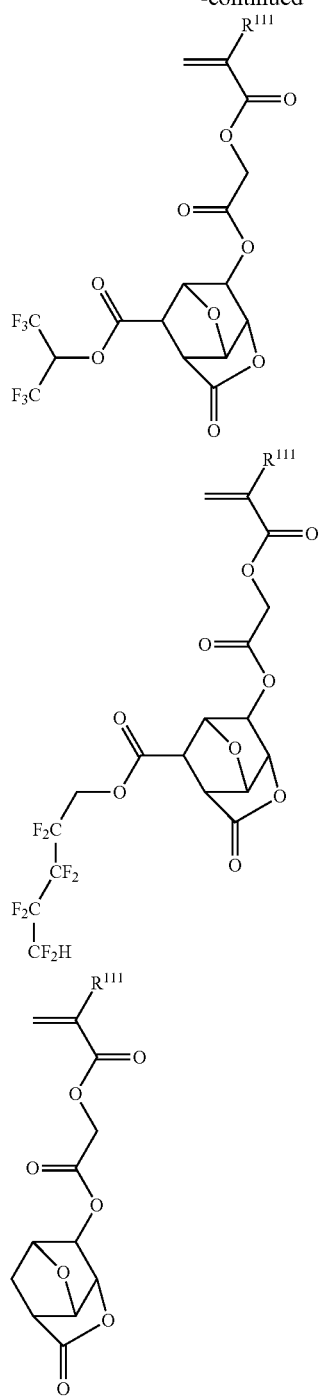

(In the formula, $R^{111}$ represents the same as before.)

In addition, among the monomers to constitute a repeating unit represented by the foregoing general formula (5L-1), details of the compound with M=1 are described in Japanese Patent Laid-Open (kokai) No. 2008-031298. The compound with M=3 can be synthesized in a similar manner by changing the starting material chloroacetyl chloride in the compound with M=1 to chlorobutyryl chloride.

A repeating unit represented by the above-mentioned general formula (9) is specifically the following.

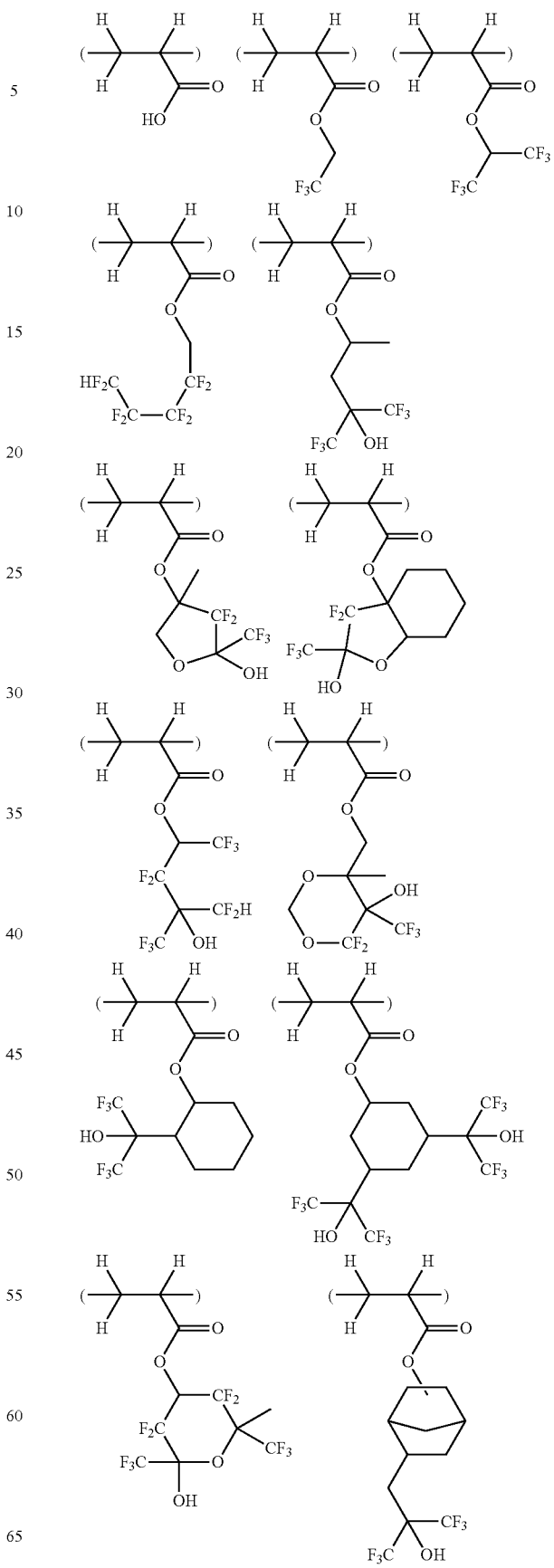

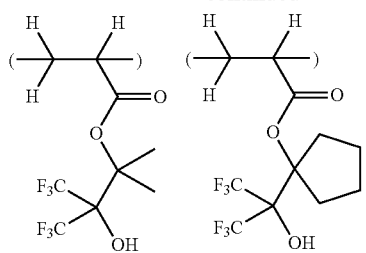
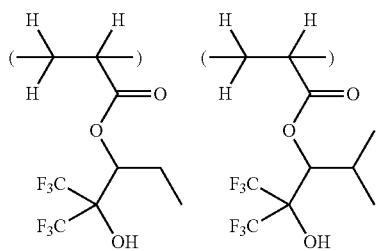
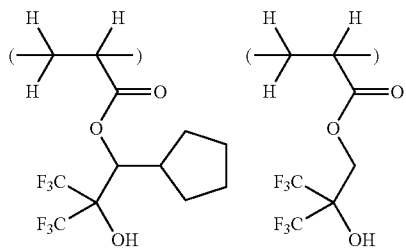
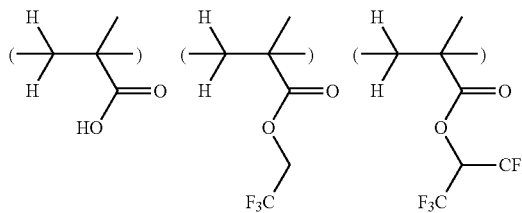
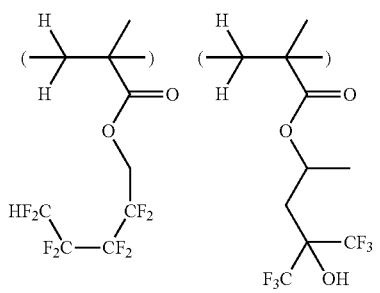
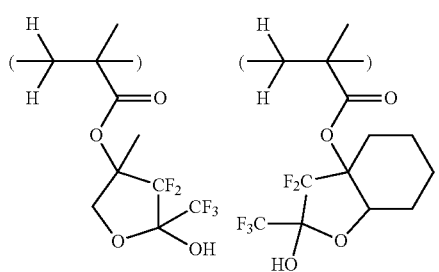
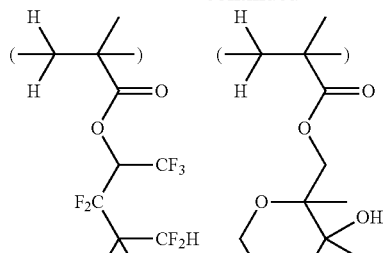
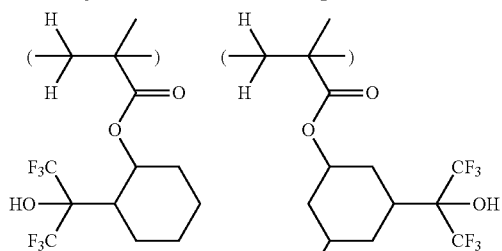
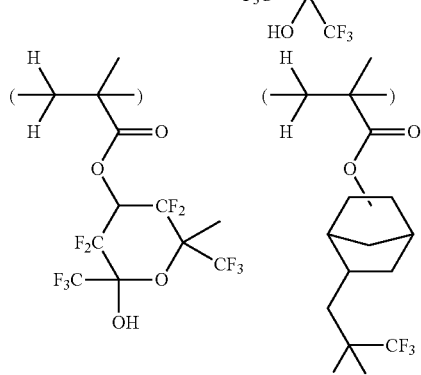
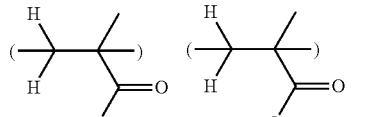
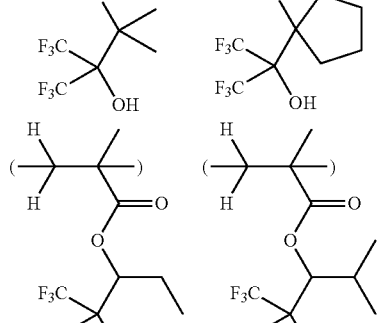
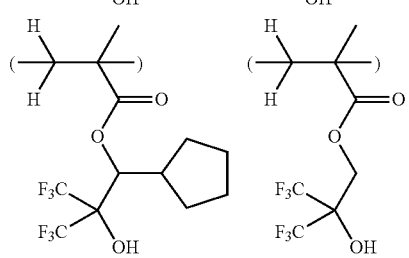

A repeating unit represented by the above-mentioned general formula (10) is specifically the following.
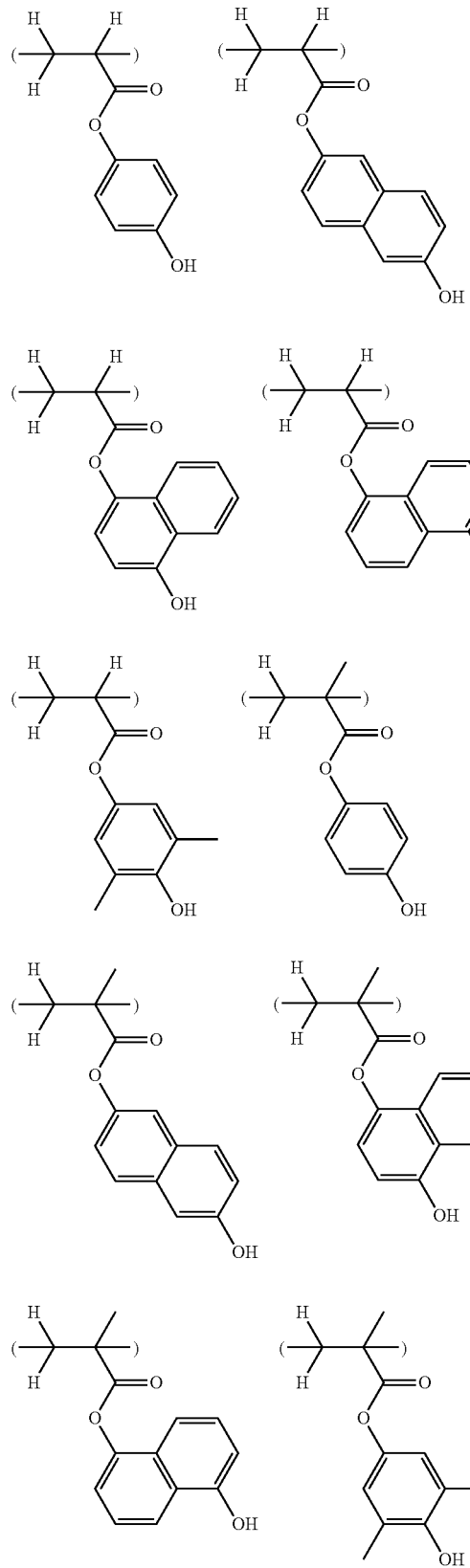
-continued
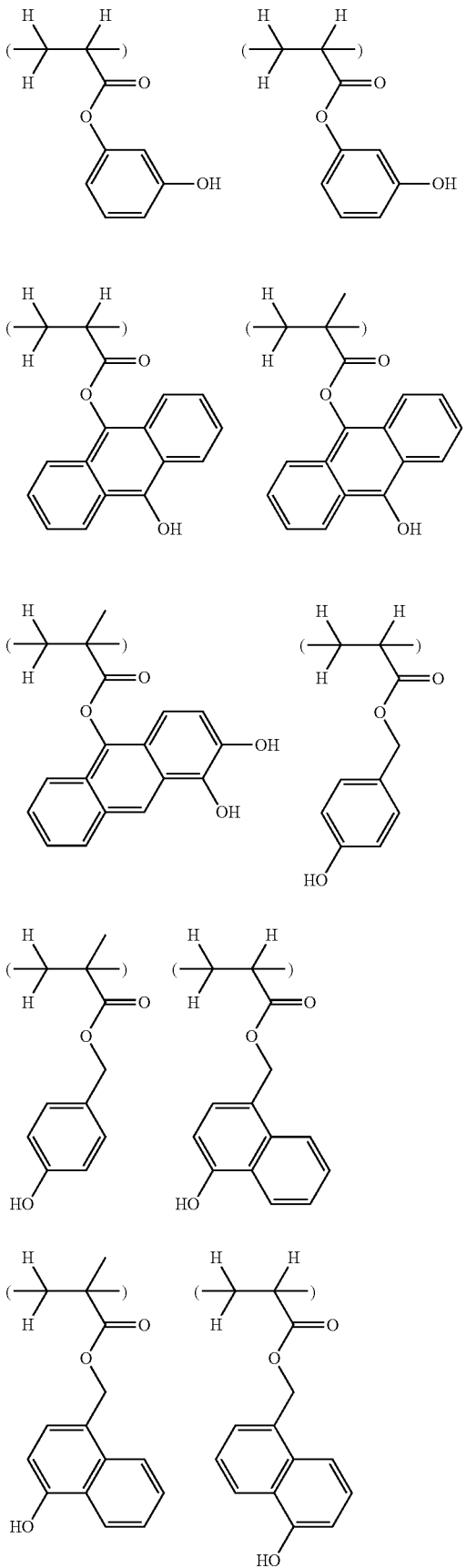

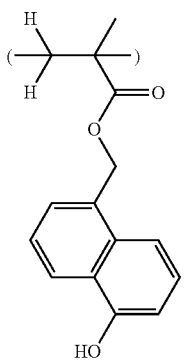

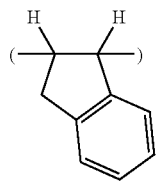

(13)

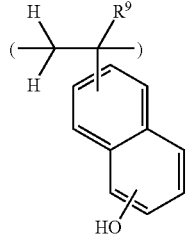

(14)

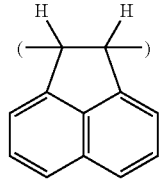

(15)

The polymer of the present invention may contain a repeating unit derived from a monomer having a carbon-carbon double bond other than those described above. For example, it may contain a repeating unit derived from substituted acrylic acid esters such as methyl methacrylate, methyl crotonate, dimethyl maleate and dimethyl itaconate; unsaturated carboxylic acids such as maleic acid, fumaric acid and itaconic acid; cyclic olefins such as norbornene, a norbornene derivative and a tetracyclo[6.2.1.1$^{3,6}$.0$^{2,7}$]dodecene derivative; unsaturated acid anhydrides such as itaconic anhydride; and other monomers.

Meanwhile, the polymer of the present invention can also be used in other lithography than a lithography of an ArF exposure such as a KrF lithography, an electron beam lithography and a EUV lithography.

The polymer of the present invention can further include, in addition to a repeating unit represented by the foregoing general formula (4) or preferably the foregoing general formula (5), any one or more kinds of repeating units represented by the following general formulae (11) to (15) and may further include any one or more kinds of repeating units represented by the above-mentioned general formulae (6) to (10).

(In the formulae, each R$^9$ independently represents a hydrogen atom, a fluorine atom, a methyl group or a trifluoromethyl group. X$^1$ represents an acid-labile group. G represents an oxygen atom or a carbonyloxy group (—C(=O)O—).)

The polymer including a repeating unit represented by the foregoing general formula (11) is decomposed by action of an acid to generate a phenolic hydroxyl group and/or a carboxylic acid thereby giving an alkaline-soluble polymer. Various groups can be used as the acid-labile group X$^1$, and specific examples of them include groups represented by the above-mentioned general formulae (L1) to (L4), tertiary alkyl groups having 4 to 20, preferably 4 to 15 carbon atoms, trialkylsilyl groups whose each alkyl group has 1 to 6 carbon atoms, and oxoalkyl groups having 4 to 20 carbon atoms.

Specifically, a repeating unit represented by the above-mentioned general formula (11) is exemplified by the following, but is not limited thereto.

(11)

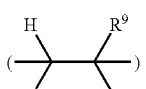

(12)

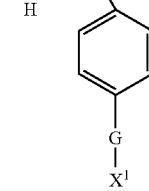

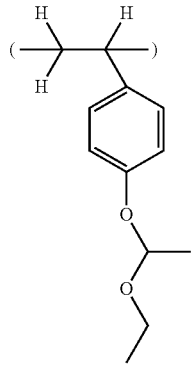

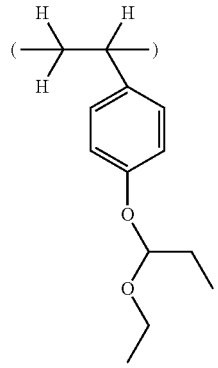

-continued

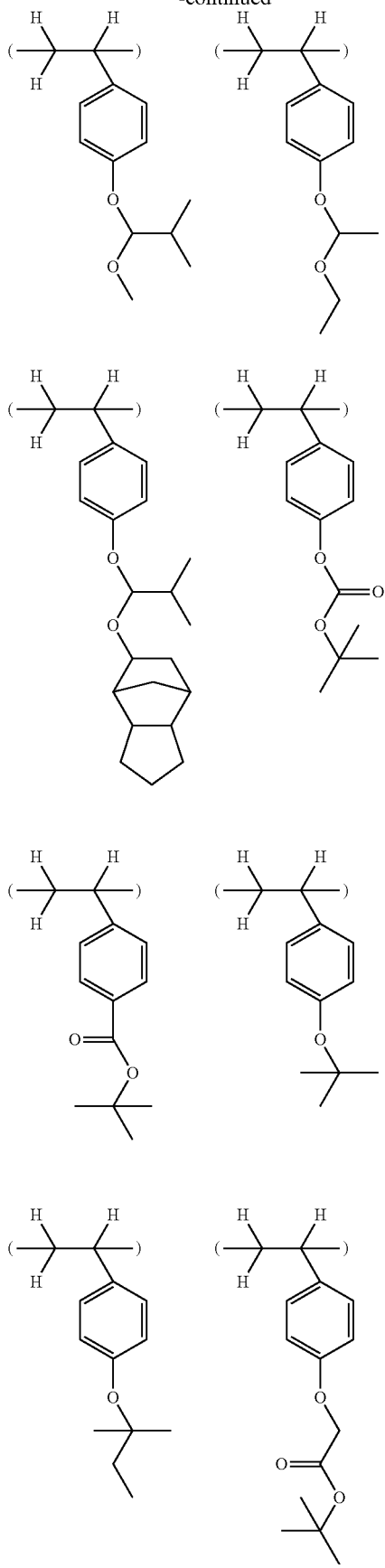

-continued

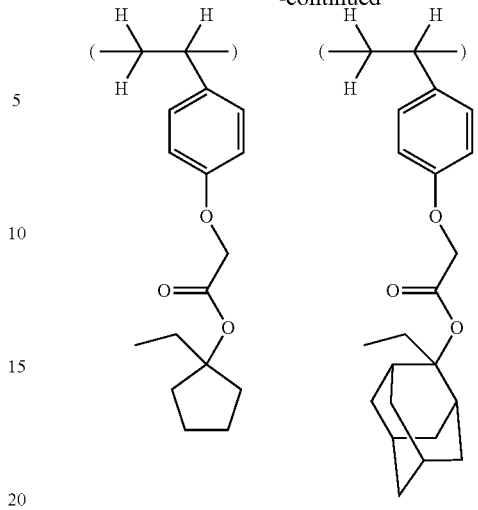

The position of substitution in the hydroxyvinylnaphthalene represented by the foregoing general formula (14) is arbitrary, but 6-hydroxy-2-vinylnaphthalene, 4-hydroxy-1-vinylnaphthalene and the like may be used, while especially 6-hydroxy-2-vinylnaphthalene is preferably used.

The polymer of the present invention can further include, in addition to a repeating unit represented by the foregoing general formula (4) or (5) and a repeating unit represented by the foregoing general formulae (11) to (15), a repeating unit represented by the foregoing general formulae (6) to (10). Especially, preferably usable is a polymer including a repeating unit represented by the foregoing general formula (6) among these repeating units represented by the formulae (6) to (10).

The polymer including a sulfonium salt of the present invention having a polymerizable functional group as a repeating unit and including any one or more kinds of repeating units represented by the foregoing general formulae (11) to (15) may contain a repeating unit derived from a monomer having a carbon-carbon double bond other than those described above. For example, it may contain a repeating unit derived from substituted acrylic acid esters such as methyl methacrylate, methyl crotonate, dimethyl maleate, and dimethyl itaconate; unsaturated carboxylic acids such as maleic acid, fumaric acid and itaconic acid; cyclic olefins such as norbornene, a norbornene derivative and a tetracyclo[6.2.1.1$^{3,6}$.0$^{2,7}$]dodecene derivative, norvornadiene; unsaturated acid anhydrides such as itaconic anhydride; styrene, acenaphthylene, vinylnaphthalene, and other monomers.

Meanwhile, the weight-average molecular weight of the polymer of the present invention is preferably 1,000 to 500,000, or more preferably 3,000 to 100,000. The weight-average molecular weight is preferably in this range, because there is no possibility that the etching resistance is extremely deteriorated and the difference in dissolution rates before and after the exposure cannot be secured and thereby resolution is deteriorated. As to the measurement method of the molecular weight, a gel permeation chromatography (GPC) with the polystyrene conversion and a light scattering method may be mentioned.

In the polymer of the present invention, the preferable ratio of each repeating unit derived from respective monomers can be made, for example, in the following ranges (% by mole), but is not limited to them.

(I) One kind, or two or more kinds of compositional units represented by the formula (4) based on a monomer of the foregoing general formula (2) can be contained in the range of more than 0% by mole to 100% or less by mole, preferably 0.1 to 30% by mole, or more preferably 1 to 20% by mole;

(II) One kind, or two or more kinds of compositional units represented by the foregoing formulae (6) to (10) and/or (11) to (15) may be contained in the range of 0% or more by mole to less than 100% by mole, preferably 70 to 99% by mole, or more preferably 80 to 95% by mole; and as appropriate, (III) One kind, or two or more kinds of compositional units derived from other monomers can be contained in the range of 0 to 80% by mole, preferably 0 to 70% by mole, or more preferably 0 to 50% by mole.

The polymer of the present invention is manufactured by copolymerizing reaction of a compound represented by the foregoing general formulae (1) to (3) as the first monomer and another compound having a polymerizable double bond as the second monomer and the monomers following thereafter.

Although various methods are exemplified as the copolymerization method for manufacturing the polymer of the present invention, a radical polymerization, an anionic polymerization or a coordination polymerization is preferable.

Preferable reaction conditions of the radical polymerization are as follows, though cases outside these ranges are not excluded:
(a) solvent: hydrocarbons such as benzene, ethers such as tetrahydrofuran, alcohols such as ethanol or ketones such as methyl isobutyl ketone,
(b) polymerization initiator: an azo compound such as 2,2'-azobisisobutyronitrile or a peroxide such as benzoyl peroxide and lauroyl peroxide,
(c) reaction temperature: about 0° C. to about 100° C., and
(d) reaction time: about 0.5 hour to about 48 hours.

Preferable reaction conditions of the anionic polymerization are as follows, though cases outside these ranges are not excluded:
(a) solvent: hydrocarbons such as benzene, ethers such as tetrahydrofuran or liquid ammonia,
(b) polymerization initiator: a metal such as sodium and potassium, an alkyl metal such as n-butyl lithium and sec-butyl lithium, a ketyl or a Grignard reagent,
(c) reaction temperature: about −78° C. to about 0° C.,
(d) reaction time: about 0.5 hour to about 48 hours, and
(e) terminator: a proton-donating compound such as methanol, a halogen compound such as methyl iodide, and other electrophilic substances.

Preferable reaction conditions of the coordination polymerization are as follows, though cases outside these ranges are not excluded:
(a) solvent: hydrocarbons such as n-heptane and toluene,
(b) catalyst: a Ziegler-Natta catalyst containing a transition metal such as titanium and an alkyl aluminum, a Philips catalyst having a chromium and a nickel compound supported on a metal oxide, an olefin-metathesis mixed catalyst typified by the mixed catalyst of tungsten and rhenium, and the like,
(c) reaction temperature: about 0° C. to about 100° C., and
(d) reaction time: about 0.5 hour to about 48 hours.

By deprotection of all or a part of the acid-labile groups of the polymer prepared by the polymerization methods, the polymer can be used for a negative-type composition which will be described later. In addition, the acid-labile group can be introduced again into the polymer whose acid-labile group was deprotected thereby enabling to introduce a substituent that is different from the acid-labile group introduced at the time of polymerization.

For example, 4-ethoxyethoxystyrene and a sulfonium salt having a polymerizable functional group represented by the foregoing general formulae (1) to (3) of the present invention are polymerized by the above radical polymerization to give a polymer, and then the ethoxyethoxy group is removed by acetic acid, pyridinium tosylate and the like to obtain a copolymer with polyhydroxystyrene. This can be used as a base resin for a negative resist composition. Further, by reacting the hydroxy styrene unit of the copolymer with di-tert-butyl dicarbonate, tert-butyl chloroacetate, various vinyl ethers and the like, an acid-labile group different from the acid-labile group attached at the time of the polymerization (the ethoxyethoxy group) can be introduced.

In addition to the above-mentioned polymer (the polymer of the present invention), other resin whose dissolution rate in an alkaline developer is changed by action of an acid may also be added to prepare the resist composition of the present invention as appropriate. Examples of the resin include (i) a poly(meth)acrylic acid derivative, (ii) a copolymer of a norbornene derivative and maleic anhydride, (iii) a hydrogenated ring-opening metathesis polymer, (iv) a copolymer of vinyl ether, maleic anhydride, and a (meth)acrylic acid derivative, and (v) a polyhydroxy styrene derivative, though are not limited to them.

(i) the poly(meth)acrylic acid derivative is a polymer formed of a combination of repeating units of the foregoing general formulae (6) to (10) and the like, and (v) the polyhydroxystyrene derivative is a polymer formed of a combination of repeating units of the foregoing general formulae (11) to (15), or a combination of any of repeating units of the formulae (6) to (10) and any of repeating units of the formulae (11) to (15). The ratio of the units relating to the acid-labile group in these polymers, for example, the ratio of one kind or two or more kinds of the monomer units of the foregoing general formula (6) and/or (11) is preferably in the range of more than 0% by mole to 80% or less by mole, more preferably 1 to 50% by mole, or further preferably 10 to 40% by mole. The ratio of the units relating to the group other than the acid-labile group in these polymers, for example, the ratio of one kind or two or more kinds of the monomer units of the foregoing general formulae (7) to (10) and/or (12) to (15), is in the range of 0% or more by mole to less than 100% by mole. However, when the group other than the acid-labile group is contained, preferable is 20% or more by mole to less than 100% by mole, more preferably 50 to 99% by mole, and particularly preferably 60 to 90% by mole.

Among these polymers, a synthetic method for the hydrogenated ring-opening metathesis polymer is specifically disclosed in Example of Japanese Patent Laid-Open (kokai) No. 2003-66612.

The blending ratio of the polymer of the present invention to other polymers is preferably in the range of mass ratio of 100:0 to 10:90, in particular 100:0 to 20:80. The blending ratio of the polymer of the present invention is preferably in this range, because a suitable performance as a resist composition can be obtained. Performance of the resist composition can be controlled by appropriately changing the blending ratio.

Here, not only one kind but also two or more kinds of the above polymers can be added. Performance of the resist composition can be controlled by using plural kinds of polymers.

The polymer of the present invention is suitably used as a base resin in a resist composition, especially a chemically amplified positive resist composition, and the present invention provides a resist composition containing the above polymer, especially a positive resist composition.

In this case, it is preferable that the positive resist composition contains,
(A) a base resin including the above polymer,
(B) an organic solvent,
and in addition, as appropriate,
(C) an acid generator,
(D) a quencher, and
(E) a surfactant.

The polymer of the present invention can also be used as a base resin in a chemically amplified negative resist composition.

In this case, it is preferable that the negative resist composition contains,
(A) a base resin including the above polymer,
(B) an organic solvent,
(F) a crosslinker crosslinked by an acid, and in addition, as appropriate,
(C) an acid generator,
(D) a quencher, and
(E) a surfactant.

As to the organic solvent of the (B) component used in the present invention, any organic solvent may be used as far as it can dissolve a base resin, an acid generator, other additive and the like. Specific examples of the organic solvent are disclosed in paragraphs [0144] to [0145] of Japanese Patent Laid-Open (kokai) No. 2008-111103. A use amount of the organic solvent is to be determined according to an intended film thickness and the like, but preferable is approximately 200 to 15,000 parts by mass, especially 400 to 8,000 parts by mass relative to 100 mass parts of the base resin.

Acid generators other than the photoacid generator made of a sulfonium salt represented by the following general formula (1) of the present invention may be added as the (C) component in the resist composition of the present invention as appropriate.

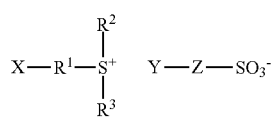 (1)

Any compound can be used as the photoacid generator of the (C) component as far as it generates an acid by exposure to a high energy beam. Suitable examples of the photoacid generator include an acid generator which is a sulfonium salt, an iodonium salt, sulfonyl diazomethane, N-sulfonyl oxyimide or oxime-O-sulfonate, and the like. These may be used solely or as a mixture of two or more kinds. These are elaborated in Japanese Patent Laid-Open (kokai) No. 2008-133448, Japanese Patent Laid-Open (kokai) No. 2007-145797, Japanese Patent Laid-Open (kokai) No. 2008-106045, Japanese Patent Laid-Open (kokai) No. 2009-7323, Japanese Patent Laid-Open (kokai) No. 2008-80474, and so on.

When two or more kinds of the photoacid generators are used mixedly and one of them is an onium salt generating a so-called weak acid, a function to control acid diffusion can also be given. For example, when a mixture of an onium salt generating a strong acid like a sulfonic acid substituted with fluorine at the α position and an onium salt generating a weak acid like a fluorine-unsubstituted sulfonic acid or a carboxylic acid is used, a strong acid generated from the photoacid generator by exposure to a high energy beam collides with the unreacted onium salt having a weak acid anion thereby releasing the weak acid and forming the onium salt having the strong acid anion by the salt-exchange. In this process, the strong acid is exchanged to the weak acid having a lower catalytic activity, and thus the acid is apparently deactivated thereby enabling to control acid diffusion.

Here, when the photoacid generator generating a strong acid is an onium salt, the strong acid generated by exposure to a high energy beam can exchange with a weak acid as mentioned above, but a weak acid generated by exposure to a high energy beam cannot undergo the salt exchange by collision with an unreacted onium salt generating a strong acid. These are caused by the phenomenon that an onium cation forms an ion pair more easily with an anion of a relatively stronger acid.

The amount of the photoacid generator added as the (C) component in the resist composition of the present invention is not particularly restricted as far as it is within a range not impairing the effects of the present invention, but preferable is 0.1 to 80 parts by mass, in particular 0.1 to 40 parts by mass relative to 100 parts by mass of the base resin in the resist composition. The ratio of the photoacid generator of the (C) component is preferably 80 parts by mass or less, because there is no possibility of deterioration in resolution and causing a problem of extraneous substances at the time of development and resist stripping. The photoacid generator of the (C) component may also be used solely or as a mixture of two or more kinds. In addition, transmittance in a resist film can also be controlled by using a photoacid generator having a low transmittance at the exposure wavelength and adjusting the adding amount.

Furthermore, a compound generating an acid by acidic decomposition (acid proliferation compound) may be added to the resist composition of the present invention. These compounds are disclosed in J. Photopolym. Sci. and Tech., 8. 43-44 and 45-46 (1995) and J. Photopolym. Sci. and Tech., 9. 29-30 (1996).

Examples of the acid proliferation compound include tert-butyl-2-methyl-2-tosyloxymethyl acetoacetate, 2-phenyl-2-(2-tosyloxyethyl)-1,3-dioxolane and the like, but are not limited to them. Among heretofore known photoacid generators, many compounds having a poor stability, especially a poor thermal stability, show the properties of the acid proliferation compound.

The adding amount of the acid proliferation compound in the resist composition of the present invention is preferably 20 or less parts by mass, especially 10 or less part by mass, relative to 100 parts by mass of the base resin in the resist composition. The adding amount is preferably 20 parts by mass or less, because diffusion control is easy and there is no possibility of deterioration in resolution and the pattern profile.

Moreover, in the resist composition of the present invention, one kind or two or more kinds of the quenchers of the component (D) may be blended.

The term "quencher" is widely used in this technical field, and means a compound that can suppress the diffusion rate of an acid and the like generated from an acid generator into a resist film. By blending a quencher, not only control of the resist sensitivity can be made easier but also the diffusion rate of an acid in the resist film can be suppressed thereby leading to improve resolution, and this in turn leads to suppressing the sensitivity change after exposure, decreasing dependency on a substrate and an environment, improving the exposure margin, the pattern profile and the like.

As such a quencher, primary, secondary and tertiary aliphatic amines, mixed amines, aromatic amines, heterocyclic amine, nitrogen-containing compound having a carboxyl group, a nitrogen-containing compound having sulfonyl group, a nitrogen-containing compound having a hydroxyl group, a nitrogen-containing compound having hydroxyphenyl group, an alcoholic nitrogen-containing compound, amides, imides, carbamates, ammonium salts, etc. are preferably used.

Specific examples of the quencher are described in paragraph [0146]-[0163] of Japanese Patent Laid-Open (kokai) No. 2008-111103.

Quencher used more preferably is tertiary amines, and specifically exemplified are tri-n-butylamine, tri-n-pentylamine, tri-n-hexylamine, tri-n-octylamine, N,N-dimethylaniline, tris(2-methoxyethoxyethyl)amine, triethanolamine, triisopropanolamine, tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4,1-aza-15-crown-5,1-aza-18-crown-6, tris(2-formyloxyethyl)amine, tris(2-acetoxyethyl)amine, tris(2-propyonyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, tris(2-benzoyloxyethyl)amine, tris[2-(4-methoxybenzoyloxy)ethyl]amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethyl amine, N,N-bis(2-acetoxyethyl)2-(2-acetoxyethoxycarbonyl)ethylamine, N,N-bis(2-hydroxyethyl)-2-[(methoxycarbonyl)methoxycarbonyl]ethylamine, N,N-bis(2-acetoxyethyl)-2-[(methoxycarbonyl)methoxycarbonyl]ethylamine, N,N-bis(2-hydroxyethyl)-2-(2-oxopropoxycarbonyl)ethylamine, N,N-bis(2-acetoxyethyl)-2-(2-oxopropoxycarbonyl) ethylamine, N,N-bis(2-hydroxyethyl) 2-(tetrahydrofurfuryloxycarbonyl) ethylamine, N,N-bis(2-acetoxyethyl)-2-(tetrahydrofurfuryloxycarbonyl)ethylamine, N,N-bis(2-hydroxyethyl)-2-[(2-oxotetrahydrofuran-3-yl)oxycarbonyl] ethylamine, N,N-bis(2-acetoxyethyl)-2-[(2-oxotetrahydrofuran-3-yl)oxycarbonyl]ethylamine, N,N-bis (2-hydroxyethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl)ethylamine, N,N-bis(2-methoxyethyl)-2-(methoxycarbonyl)ethylamine, N-(2-hydroxyethyl)bis[2-(methoxycarbonyl)ethyl]amine, N-(2-acetoxyethyl)bis[2-(methoxycarbonyl)ethyl]amine, N-(2-hydroxyethyl)bis[2-(ethoxycarbonyl)ethyl]amine, N-(2-acetoxyethyl)bis[2-(ethoxycarbonyl)ethyl]amine, N-(3-hydroxy-1-propyl)bis [2-(methoxycarbonyl)ethyl]amine, N-(3-acetoxy-1-propyl) bis[2-(methoxycarbonyl)ethyl]amine, N-(2-methoxyethyl) bis[2-(methoxycarbonyl)ethyl]amine, N-butylbis[2-(methoxycarbonyl)ethyl]amine, N-butylbis[2-(2-methoxyethoxycarbonyl)ethyl]amine, N-methylbis(2-acetoxyethyl)amine, N-ethylbis(2-acetoxyethyl)amine, N-methylbis(2-pivaloyloxyethyl)amine, N-ethylbis[2-(methoxycarbonyloxy)ethyl]amine, N-ethylbis[2-(tert-butoxycarbonyloxy)ethyl]amine, tris(methoxycarbonylmethyl) amine, tris(ethoxycarbonylmethyl)amine, N-butylbis (methoxycarbonylmethyl)amine, N-hexylbis (methoxycarbonylmethyl)amine, and β-(diethylamino)-δ-valerolactone.

Furthermore, exemplified are 1-[2-(methoxymethoxy) ethyl]pyrrolidine, 1-[2-(methoxymethoxy)ethyl]piperidine, 4-[2-(methoxymethoxy)ethyl]morpholine, 1-[2-(methoxymethoxy)ethyl]imidazole, 1-[2-(methoxymethoxy)ethyl] benzimidazole, 1-[2-(methoxymethoxy)ethyl]-2-phenylbenzimidazole, 1-[2-[(2-methoxyethoxy)methoxy]ethyl] pyrrolidine, 1-[(2-[(2-methoxyethoxy)methoxy]ethyl] piperidine, 4-[2-[(2-methoxyethoxy)methoxy]ethyl] morpholine, 1-[2-[(2-methoxyethoxy)methoxy]ethyl] imidazole, 1-[2-[(2-methoxyethoxy)methoxy]ethyl] benzimidazole, 1-[2-[(2-methoxyethoxy)methoxy]ethyl]-2-phenylbenzimidazole, 1-[2-[2-(2-methoxyethoxy)ethoxy] ethyl]pyrrolidine, 1-[2-[2-(2-methoxyethoxy)ethoxy]ethyl] piperidine, 4-[2-[2-(2-methoxyethoxy)ethoxy]ethyl] morpholine, 1-[2-[2-(2-methoxyethoxy)ethoxy]ethyl] imidazole, 1-[2-[2-(2-methoxyethoxy)ethoxy]ethyl] benzimidazole, 1-[2-[2-(2-methoxyethoxy)ethoxy]ethyl]-2-phenylbenzimidazole, 1-[2-[2-(2-butoxyethoxy)ethoxy] ethyl]pyrrolidine, 1-[2-[2-(2-butoxyethoxy)ethoxy]ethyl] piperidine, 4-[2-[2-(2-butoxyethoxy)ethoxy]ethyl] morpholine, 1-[2-[2-(2-butoxyethoxy)ethoxy]ethyl] imidazole, 1-[2-[2-(2-butoxyethoxy)ethoxy]ethyl] benzimidazole, 1-[2-[2-(2-butoxyethoxy)ethoxy]ethyl]-2-phenylbenzimidazole, 1-[2-[2-[2-(2-methoxyethoxy) ethoxy]ethoxy]ethyl]pyrrolidine, 1-[2-[2-[2-(2-methoxyethoxy)ethoxy]ethoxy]ethyl]piperidine, 4-[2-[2-[2-(2-methoxyethoxy)ethoxy]ethoxy]ethyl]morpholine, 1-[2-[2-[2-(2-methoxyethoxy)ethoxy]ethoxy]ethyl]imidazole, 1-[2-[2-[2-(2-methoxyethoxy)ethoxy]ethoxy]ethyl]benzimidazole, 1-[2-[2-[2-(2-methoxyethoxy)ethoxy]ethoxy] ethyl]-2-phenylbenzimidazole, 4-[2-[2-[2-(2-butoxyethoxy) ethoxy]ethoxy]ethyl]morpholine, 2-(1-pyrrolidinyl)ethyl acetate, 2-piperidinoethyl acetate, 2-morpholinoethyl acetate, 2-(1-imidazolyl)ethyl acetate, 2-(1-benzimidazolyl) ethyl acetate, 2-(2-phenyl-1-benzimidazolyl)ethyl acetate, 2-methoxyethyl morpholinoacetate, 2-(1-pyrrolidinyl)ethyl 2-methoxyacetate, 2-piperidinoethyl 2-methoxyacetate, 2-morpholinoethyl 2-methoxyacetate, 2-(1-imidazolyl)ethyl 2-methoxyacetate, 2-(1-benzimidazolyl)ethyl 2-methoxyacetate, 2-(2-phenyl-1-benzimidazolyl)ethyl 2-methoxyacetate, 2-(1-pyrrolidinyl)ethyl 2-(2-methoxyethoxy)acetate, 2-piperidinoethyl 2-(2-methoxyethoxy)acetate, 2-morpholinoethyl 2-(2-methoxyethoxy)acetate, 2-(1-imidazolyl)ethyl 2-(2-methoxyethoxy)acetate, 2-(1-benzimidazolyl)ethyl 2-(2-methoxyethoxy)acetate, 2-(2-phenyl-1-benzimidazolyl)ethyl 2-(2-methoxyethoxy)acetate, 2-(1-pyrrolidinyl) ethyl 2-[2-(2-methoxyethoxy)ethoxy]acetate, 2-piperidinoethyl 2-[2-(2-methoxyethoxy)ethoxy]acetate, 2-morpholinoethyl 2-[2-(2-methoxyethoxy)ethoxy]acetate, 2-(1-imidazolyl)ethyl 2-[2-(2-methoxyethoxy)ethoxy]acetate, 2-(1-benzimidazolyl)ethyl 2-[2-(2-methoxyethoxy) ethoxy]acetate, 2-(2-phenyl-1-benzimidazolyl)ethyl 2-[2-(2-methoxyethoxy)ethoxy]acetate, 2-morpholinoethyl butyrate, 2-morpholinoethyl hexanoate, 2-morpholinoethyl octanoate, 2-morpholinoethyl decanoate, 2-morpholinoethyl laurate, 2-morpholinoethyl myristate acid, 2-morpholinoethyl palmitate, 2-morpholinoethyl stearate, 2-morpholinoethyl behenate, 2-morpholinoethyl cholate, 2-morpholinoethyl tris(O-acetyl)cholate, 2-morpholinoethyl tri(O-formyl)cholate, 2-morpholinoethyl dehydrocholate, 2-morpholinoethyl cyclopentanecarboxylate, 2-morpholinoethyl cyclohexanecarboxylate, 2-(1-pyrrolidinyl)ethyl 7-oxanorbornane-2-carboxylate, 2-piperidinoethyl 7-oxanorbornane-2-carboxylate, 2-morpholinoethyl 7-oxanorbornane-2-carboxylate, 2-(1-imidazolyl)ethyl 7-oxanorbornane-2-carboxylate, 2-(1-benzimidazolyl)ethyl 7-oxanorbornane-2-carboxylate, 2-(2-phenyl-1-benzimidazolyl)ethyl 7-oxanorbornane-2-carboxylate, 2-morpholinoethyl adamantanecarboxylate, 2-(1-pyrrolidinyl)ethyl formate, 2-piperidinoethyl propionate, 2-morpholinoethyl acetoxyacetate, 2-(1-pyrrolidinyl)ethyl methoxyacetate, 2-(1-pyrrolidinyl)ethyl benzoate, 2-piperidinoethyl benzoate, 2-morpholinoethyl benzoate, 2-(1-imidazolyl)ethyl benzoate, 2-(1-benzimidazolyl)ethyl benzoate, 2-(2-phenyl)-1-benzimidazolyl)ethyl benzoate, 2-(1-pyrrolidinyl)ethyl 4-methoxybenzoate, 2-piperidinoethyl 4-methoxy benzoate, 2-morpholinoethyl 4-methoxybenzoate, 2-(1-imidazolyl)ethyl 4-methoxybenzoate, 2-(1-benzimidazolyl) ethyl 4-methoxybenzoate, 2-(2-phenyl-1-benzimidazolyl) ethyl 4-methoxybenzoate, 2-(1-pyrrolidinyl)ethyl 4-phenylbenzoate, 2-piperidinoethyl 4-phenylbenzoate, 2-morpholinoethyl 4-phenylbenzoate, 2-(1-imidazolyl)ethyl 4-phenylbenzoate, 2-(1-benzimidazolyl)ethyl 4-phenylbenzoate, 2-(2-phenyl-1-benzimidazolyl)ethyl 4-phenylbenzoate, 2-(1-pyrrolidinyl)ethyl 1-naphthalenecarboxylate, 2-piperidinoethyl 1-naphthalenecarboxylate, 2-morpholinoethyl 1-naphthalenecarboxylate, 2-(1-imidazolyl)ethyl 1-naphthalenecarboxylate, 2-(1-benzimidazolyl)ethyl 1-naphthalenecarboxylate, 2-(2-phenyl-1-benzimidazolyl) ethyl 1-naphthalenecarboxylate, 2-(1-pyrrolidinyl)ethyl 2-naphthalenecarboxylate, 2-piperidinoethyl 2-naphthalenecarboxylate, 2-morpholinoethyl 2-naphthalenecarboxylate, 2-(1-imidazolyl)ethyl 2-naphthalenecarboxylate, 2-(1-benzimidazolyl)ethyl 2-naphthalenecarboxylate, 2-(2-phenyl-1-benzimidazolyl)ethyl 2-naphthalenecarboxylate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino) propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl) propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, etc.

Here, the blending amount of the quencher is preferably 0.01 to 20 parts by mass, in particular 0.1 to 10 parts by mass, relative to 100 parts by mass of the total base resins. The blending amount is preferably 0.01 parts by mass or more, because blending effects can be realized efficiently. In addition, the amount is preferably 20 parts by mass or less, because there is no possibility that the sensitivity becomes too low.

In the resist composition of the present invention, in order to improve the coating properties, in addition to the above components, a conventionally used surfactant (E) may be added as an arbitrary component.

Here, the adding amount of the arbitrary component is usual in the range not impairing the effects of the present invention.

Specific examples of the surfactant are disclosed in the paragraphs [0165] to [0166] of Japanese Patent Laid-Open (kokai) No. 2008-111103. In addition, a surfactant of a partially fluorinated oxetane ring-opened polymer as represented by the following structural formula (surf-1) may also be preferably used.

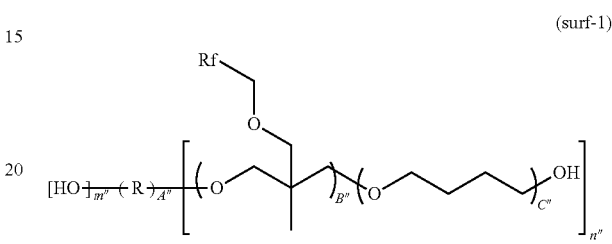

(surf-1)

Here, R, Rf, A", B", C", m" and n" are applied only to the above formula (surf-1) regardless of the description made on substances other than the above surfactants. R represents a 2- to 4-valent aliphatic group having 2 to 5 carbon atoms, specifically ethylene, 1,4-butylene, 1,2-propylene, 2,2-dimethyl-1,3-propylene, and 1,5-pentylene as the divalent group. As the 3 or 4-valent group, the following are enumerated.

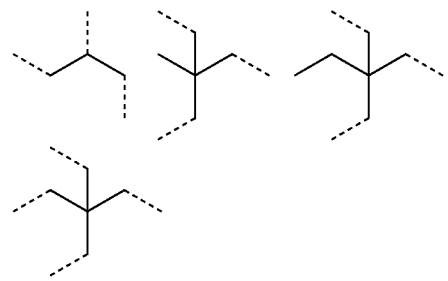

(In the formulae, the broken lines represent bonding hands and each represents a partial structure derived from glycerol, trimethylol ethane, trimethylol propane, and pentaerythritol.)

Among them, 1,4-butylene or 2,2-dimethyl-1,3-propylene is preferably used.

Rf represents a trifluoromethyl group or a pentafluoroethyl group, and preferably a trifluoromethyl group. m" represents an integer of 0 to 3 and n" represents an integer of 1 to 4, wherein the sum of m" and n" is the valency of R and is an integer of 2 to 4. A" represents 1, B" represents an integer of 2 to 25, and C" represents an integer of 0 to 10. Preferably, B" represents an integer of 4 to 20 and C" represents 0 or 1. Each structural unit in the above structures does not stipulate the sequence of them, and they may be bonded in blocks or randomly. Manufacturing of the partially fluorinated oxetane ring-opened polymer surfactant is elaborated in the description of U.S. Pat. No. 5,650,483 and so on.

Among the surfactants, FC-4430, Surflon S-381, Surfynol E1004, KH-20, KH-30, and the oxetane ring-opened polymer represented by the structural formula (surf-1) are preferable. These may be used solely or in a combination of two or more kinds.

The adding amount of the surfactant in the resist composition of the present invention is 2 or less parts by mass, or preferably 1 or less parts by mass, and when blended, preferably 0.01 or more part by mass, relative to 100 parts by mass of the base resin in the resist composition.

In the resist composition of the present invention, a surfactant having a function to reduce water penetration and leaching by orientating on the resist surface after spin coating may be added in the case of the immersion exposure using water, especially when a resist top coat is not used. This surfactant is preferably a polymer-type surfactant having a property to be dissolved in an alkaline developer but not in water, and in particular the one giving a high water-repellent property with an improved sliding property.

The adding amount of the polymer-type surfactant is 0.001 to 20 parts by mass, or preferably 0.01 to 10 parts by mass, relative to 100 parts by mass of the base resin of the resist composition. These are elaborated in Japanese Patent Laid-Open (kokai) No. 2007-297590.

When the polymer of the present invention is used for a chemically amplified negative resist composition, it is necessary that the composition has a repeating unit having a substituent crosslinkable by an acid crosslinker. More specific examples of the repeating unit include a repeating unit derived from acrylic acid, methacrylic acid, hydroxystyrene (position of substitution is arbitrary), and hydroxyvinylnaphthalene (position of substitution is arbitrary) and the like, though it is not limited to them.

In addition, an alkaline-soluble resin other than the above polymers may be added.

Examples of the resin include poly(p-hydroxystyrene), poly(m-hydroxystyrene), poly(4-hydroxy-2-methylstyrene), poly(4-hydroxy-3-methylstyrene), poly($\alpha$-methyl-p-hydroxystyrene), partially hydrogenated (p-hydroxystyrene) copolymer, (p-hydroxystyrene-$\alpha$-methyl-p-hydroxystyrene) copolymer, (p-hydroxystyrene-$\alpha$-methylstyrene) copolymer, (p-hydroxystyrene-styrene) copolymer, (p-hydroxystyrene-m-hydroxystyrene) copolymer, (p-hydroxystyrene-styrene) copolymer, (p-hydroxystyrene-acrylic acid) copolymer, (p-hydroxystyrene-methacrylic acid) copolymer, (p-hydroxystyrene-methyl acrylate) copolymer, (p-hydroxystyrene-acrylic acid-methyl methacrylate) copolymer, (p-hydroxystyrene-methyl acrylate) copolymer, (p-hydroxystyrene-methacrylic acid-methyl methacrylate) copolymer, polymethacrylic acid, polyacylic acid, (acrylic acid-methyl acrylate) copolymer, (methacrylic acid-methyl methacrylate) copolymer, (acrylic acid-maleimide) copolymer, (methacrylic acid-maleimide) copolymer, (p-hydroxystyrene-acrylic acid-maleimide) copolymer, (p-hydroxystyrene-methacrylic acid-maleimide) copolymer, etc., but are not limited to them.

The blending ratio of the polymer of the present invention to the other alkaline-soluble resin is preferably in the range of mass ratio of 100:0 to 10:90, in particular 100:0 to 20:80. The blending ratio of the polymer of the present invention is preferably in this range, because suitable performance as the resist composition can be obtained efficiently. By appropriately changing the blending ratio, performance of the resist composition can be controlled.

Here, not only one kind but also two or more kinds of the alkaline-soluble resin can be added. Performance of the resist composition can be controlled by using plural kinds of polymers.

Examples of a crosslinker of the component (F) that crosslinks by an acid, that is, an acid crosslinker that forms a crosslinking structure by action of an acid, include a compound having two or more groups selected from hydroxymethyl, alkoxymethyl, epoxy and vinyl ether groups in the molecule. A substituted glycouril derivative, a urea derivative, hexa(methoxymethyl) melamine and the like can be suitably used as the acid crosslinker of the chemically amplified negative resist composition of the present invention. Examples of the crosslinker include N,N,N',N'-tetramethoxymethyl urea, hexamethoxymethyl melamine, tetrahydroxymethyl-substituted glycolurils, tetraalkoxymethyl-substituted glycolurils such as tetramethoxymethyl glycoluril, substituted or unsubstituted bis-hydroxymethyl phenols, and a condensate of a phenolic compound such as bisphenol A and epichlorohydrin and the like. Particularly preferable crosslinkers include 1,3,5,7-tetraalkoxymethyl glycoluril such as 1,3,5,7-tetramethoxymethyl glycoluril, 1,3,5,7-tetrahydroxymethyl glycoluril, 2,6-dihydroxymethyl-p-cresol, 2,6-dihydroxymethyl phenol, 2,2',6,6'-tetrandyroxymethyl-bisphenol A, 1,4-bis[2-(2-hydroxypropyl)]-benzene, N,N,N',N'-tetramethoxymethyl urea, hexamethoxymethyl melamine, etc.

The adding amount of the acid crosslinker of the component (F) in the resist composition of the present invention is arbitrary, but preferable is 1 to 20 parts by mass or especially 5 to 15 parts by mass, relative to 100 parts by mass of the base resin in the resist composition. These crosslinkers may be used solely or in a combination of two or more kinds.

In addition to the above components, other components such as a dissolution inhibitor, an acidic compound, a stabilizer, and pigments may also be added in the resist composition of the present invention as the arbitrary components as appropriate. Here, each adding amount of these arbitrary components is usual in the range not impairing the effects of the present invention.

Patterning by using the resist composition of the present invention may be carried out with a heretofore known lithography technology. One example is shown below, but the patterning process of the present invention is not limited to this.

For example, coating is done on a substrate for integrated circuit manufacturing (Si, $SiO_2$, SiN, SiON, TiN, WSi, BPSG, SOG, an organic anti-reflection film, and the like) or on a substrate for mask circuit manufacturing (Cr, CrO, CrON, MoSi, and the like) by a technique such as spin-coating to make the film thickness of 0.05 to 2.0 pm, and then a pre-bake is done on a hot plate at 60 to 150° C. for 1 to 20 minutes, or preferably at 80 to 140° C. for 1 to 10 minutes. After that, a high energy beam such as a deep-ultraviolet beam, an excimer laser, and an X-ray, or an electron beam is irradiated onto a mask that covers the resist film to form an intended pattern. Alternatively, an electron beam is directly irradiated for drawing without via the mask for patterning. The exposure dose is 1 to 200 $mJ/cm^2$, or preferably about 10 $mJ/cm^2$ to about 100 $mJ/cm^2$ in the case of the light exposure, and is about 0.1 $\mu C/cm^2$ to about 20 $\mu C/cm^2$, or preferably about 3 $\mu C/cm^2$ to about 10 $\mu C/cm^2$ in the case of the electron beam exposure. Exposure is done by a usual exposure method, and as appropriate, an immersion method in which the space between a mask and a resist film is immersed with a liquid can also be used. In that case, a top coat not soluble in water can also be used. After that, a post-exposure bake (PEB) is done on a hot plate at 60 to 150° C. for 1 to 20 minutes, or preferably at 80 to 140° C. for 1 to 10 minutes. Further, development is done by using a developer of an alkaline aqueous solution such as tetramethyl ammonium hydroxide (TMAH) with a concentration of 0.1 to 3% by mass, or preferably 2 to 3% by mass, for 0.1 to 3 minutes, or preferably 0.5 to 2 minutes by a usual method such as a dip method, a puddle method, and a spray method to form an intended pattern on the substrate. Meanwhile, the resist composition of the present invention is most suitable, for fine patterning especially by a deep-ultraviolet beam or an excimer laser with 250 to 190 nm wavelength, EUV, an X-ray, and an electron beam, among the high energy beams.

The above-mentioned water-insoluble top coat is used to prohibit dissolution from a resist film and to improve water-repellent properties on the film surface. It can be classified into two types; one is the type in which delamination by an organic solvent not dissolving a resist film is necessary before the alkaline development, and the other is the alkaline-soluble type in which the top coat is soluble in an alkaline developer and removed together with a soluble part of the resist film.

In the latter case, in particular, a composition, in which a polymer having a 1,1,1,3,3,3-hexafluoro-2-propanol residue that is insoluble in water and soluble in an alkaline developer is dissolved in an alcoholic solvent having 4 or more carbon atoms, an ether solvent having 8 to 12 carbon atoms or a mixture thereof, is preferable.

A composition may also be made by dissolving the surfactant that is insoluble in water and soluble in an alkaline developer into an alcoholic solvent having 4 or more carbon atoms, an ether solvent having 8 to 12 carbon atoms, or a mixture of them.

Further, as the means for the patterning, after formation of the photoresist film, an acid generator and the like may be extracted from the film surface or particles may be washed out by rinsing with pure water (post-soak), or rinsing may be done to remove the water remained on the film after exposure (post-soak).

In manufacturing a photomask by forming the resist pattern on a photomask blanks, especially when used for processing of the photomask blanks having a chromium material on the outermost surface, the resist pattern is not easily affected by the substrate dependency, and thus the patterning process of the present invention can be applied advantageously. Further, also when the resist pattern is formed on the material containing an oxygen- or nitrogen-containing silicone including a molybdenum-silicon compound, a high resolution and a temporal stability can be obtained, and thus a photomask with a high reliability can be manufactured.

The processing of a photomask blanks using a resist pattern as an etching mask may be made by any heretofore known method, but it is general that a chlorine-type dry etching containing an oxygen is done in the case that the outermost surface is made of a chromium compound, and a fluorine-type dry etching is done in the case that the outermost surface is made of a transition metal-silicon compound.

EXAMPLES

Hereinafter, the present invention will be explained specifically by Examples and Comparative Examples, but the present invention is not limited to these descriptions.

Synthesis Example 1-1

Synthesis of 4-(2-methacryloyloxyethoxy)phenyldiphenylsulfonium 4-methylbenzenesulfonate 4-hydroxyphenyldiphenylsulfonium 4-methylbenzene-sulfonate was used as a starting material, and the intended substance was synthesized according to the method disclosed in WO2007/069640. The intended substance was used for the next reaction as a crude substance.

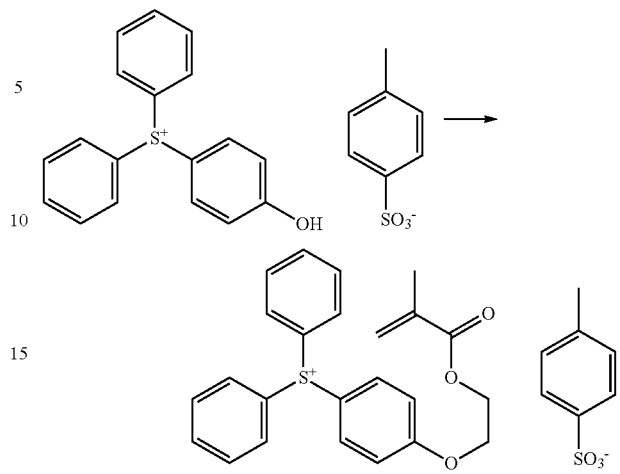

Synthesis Example 1-2

Synthesis of triethylammonium 1,1,3,3,3-pentafluoro-2-(methacryloyloxy)propane-1-sulfonate Triethylammonium 1,1,3,3,3-pentafluoro-2-(pivaloyloxy) propane-1-sulfonate prepared by the method disclosed in Japanese Patent Laid-Open (kokai) No. 2007-304490 is dissolved in methanol and 2 equivalents of 25 wt % aqueous solution of sodium hydrate was added thereto. After confirming a separation of a pivaloyloxy group by $^{19}$F-NMR, 2.1 equivalents of 12N hydrochloric acid was added and both methanol and water were removed by evaporation under reduced pressure, and then ethyl ether was added to the obtained residue to perform recrystallization. The crude substance containing sodium chloride was filtrated and then triethylamine (1.5 equivalents), 4-dimethylamino pyridine (0.025 equivalent) and acetonitrile (4 fold of the crude substance by weight) were added and the mixture was iced-cooled. Then, methacrylic acid anhydride (1.0 equivalent) was dropped and the mixture was stirred overnight. 3N hydrochloric acid was added to the reaction solution to make the solution acidic, and acetonitrile was removed by evaporation under reduced pressure at low temperature, and thereafter, the solution was dissolved in dichloromethane and then washed by water. After dichloromethane was removed by evaporation under reduced pressure, the obtained crude substance was used for the next reaction without purification.

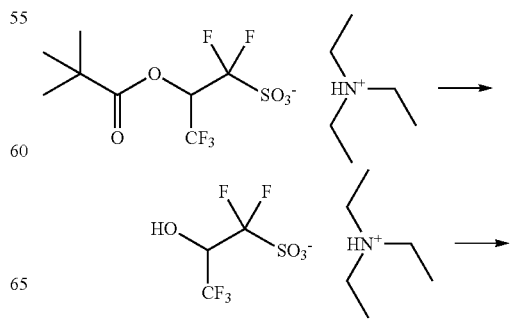

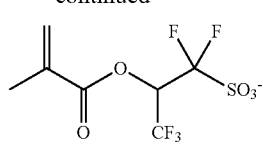

Synthesis Example 1-3

Synthesis of 4-(2-methacryloyloxyethoxy)phenyldiphenylsulfonium 1,1,3,3,3-pentafluoro-2-(methacryloyloxy)propane-1-sulfonate (PAG-1)

4-(2-methacryloyloxyethoxy)phenyldiphenylsulfonium 4-methylbenzenesulfonate of Synthesis Example 1-1 and triethylammonium 1,1,3,3,3-pentafluoro-2-(methacryloyloxy)propane-1-sulfonate of Synthesis Example 1-2 are mixed and ion-changed in a dichloromethane-water system. An organic layer after washing by water was concentrated under reduced pressure, the residue was purified by silica gel column chromatograph, and thereby the intended substance was obtained as an oily substance. The structure of the intended substance is shown below.

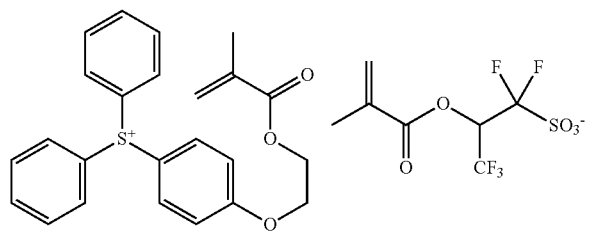

Figure 2:
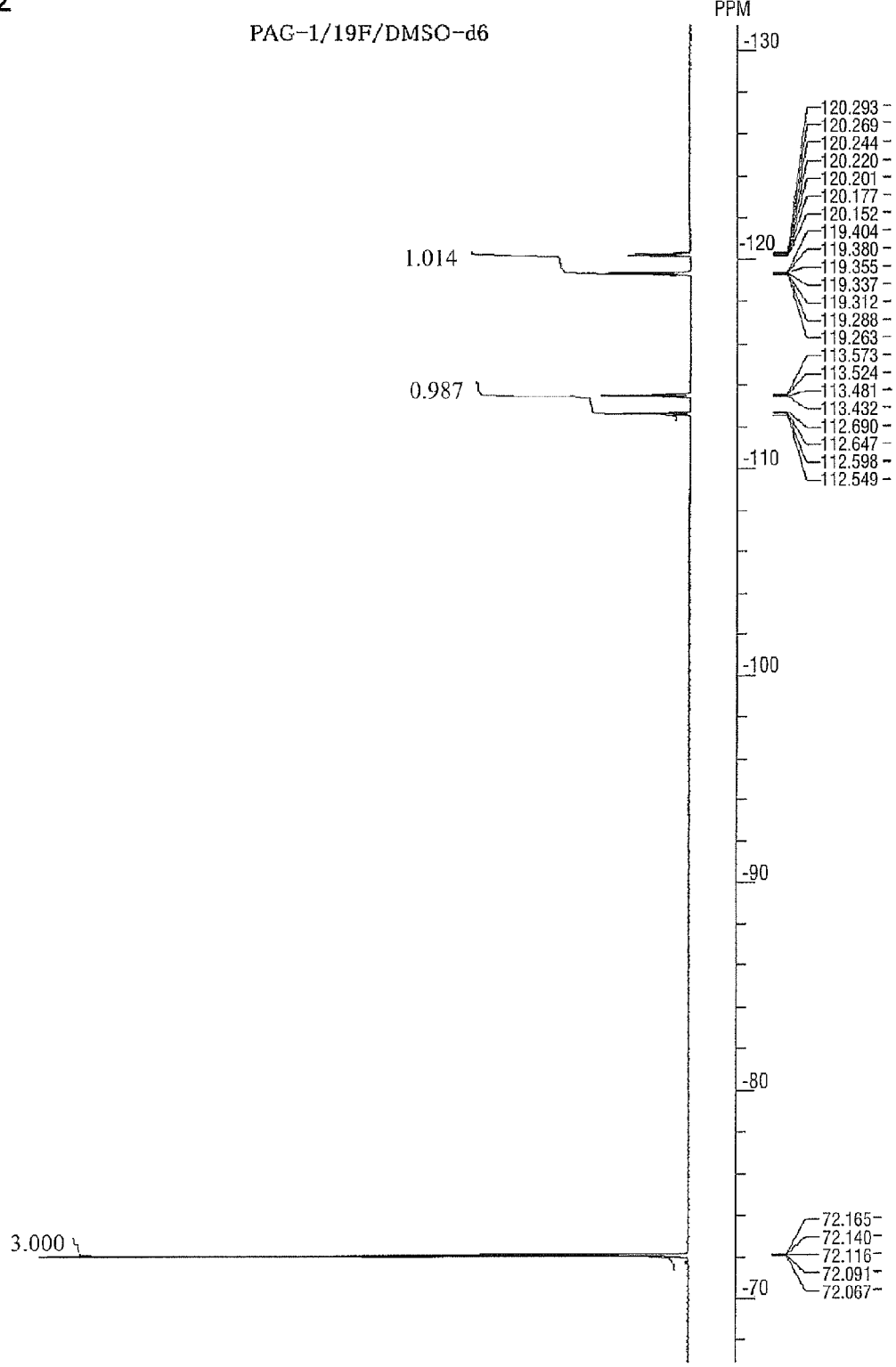
FIG. 2 is a diagram showing the $^{19}$F-NMR spectrum of PAG-1 in Synthesis Example 1-3.

Spectrum data of the intended substance thus obtained are shown below. Results of the nuclear magnetic resonance spectra ($^1$H-NMR, $^{19}$F-NMR/DMSO-$d_6$) are shown in FIG. 1 and FIG. 2, respectively. Meanwhile, trace amounts of residual solvents (diisopropyl ether and water) are detected in $^1$H-NMR.

IR Spectrum (IR(KBr); cm$^{-1}$): 1743, 1717, 1590, 1496, 1477, 1448, 1372, 1311, 1296, 1264, 1215, 1169, 1133, 1069, 994, 949, 902, 839, 750, 684 and 642 cm$^{-1}$ Time-of-Flight Mass Spectrum Analysis (TOFMS; MARDI): POSITIVE: M$^{+}$ 391 (corresponding to $C_{24}H_{23}O_3S$) NEGATIVE: M$^{-}$ 297 (corresponding to $C_7H_6F_5O_5S$)

Synthesis Example 1-4

Synthesis of 4-hydroxyphenyldiphenylsulfonium 1,1,3,3,3-pentafluoro-2-(methacryloyloxy)propane-1-sulfonate 4-hydroxyphenyldiphenylsulfonium 4-methylbenzenesulfonate and triethylammonium 1,1,3,3,3-pentafluoro-2-(methacryloyloxy)propane-1-sulfonate of Synthesis Example 1-2 are mixed and ion-changed in a dichloromethane-water system. An organic layer after washing by water was concentrated under reduced pressure and was used for the next reaction as a crude substance.

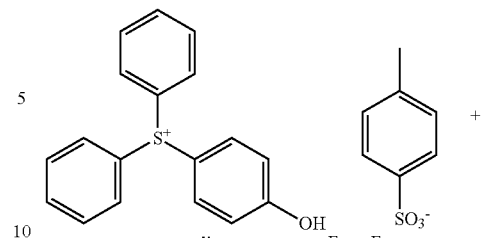

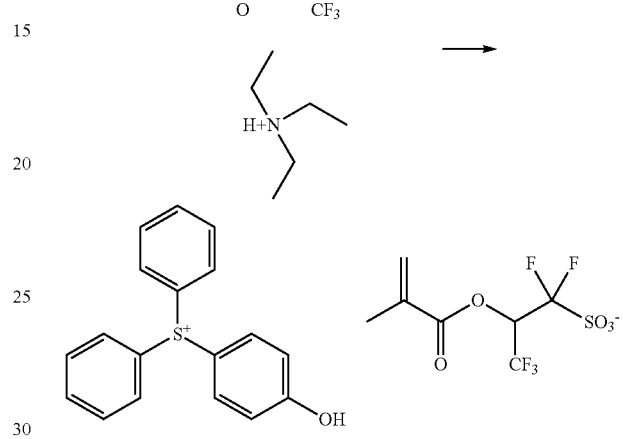

Synthesis Example 1-5

Synthesis of 4-methacryloyloxyphenyldiphenylsulfonium 1,1,3,3,3-pentafluoro-2-(methacryloyloxy)propane-1-sulfonate (PAG-2)

After 20 mmoles of 4-hydroxyphenyldiphenylsulfonium 1,1,3,3,3-pentafluoro-2-(methacryloyloxy)propane-1-sulfonate obtained in Synthesis Example 1-4, 22 mmoles of methacrylic acid anhydride, 24 mmoles of triethylamine and 4 mmoles of N,N-dimethylaminopyridine were mixed and stirred overnight, the reaction was terminated by adding dilute hydrochloric acid to the reaction solution. Thereafter, an organic layer of the quenched reaction solution was separated, and then washed by water, and dichloromethane was removed by evaporation under reduced pressure. Methyl isobutyl ketone was added into the residue, and an organic layer was separated and then washed by water, and methyl isobutyl ketone was removed by evaporation under reduced pressure. The obtained residue was washed by diisopropyl ether, and thereby the intended substance was obtained as an oily substance (with yield of 76%). The structure of the intended substance is shown below.

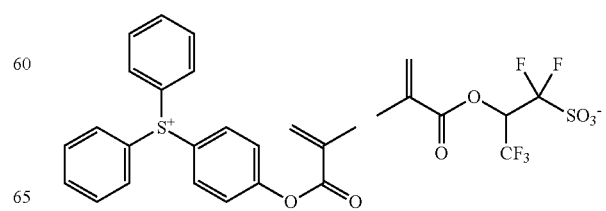

Figure 3:
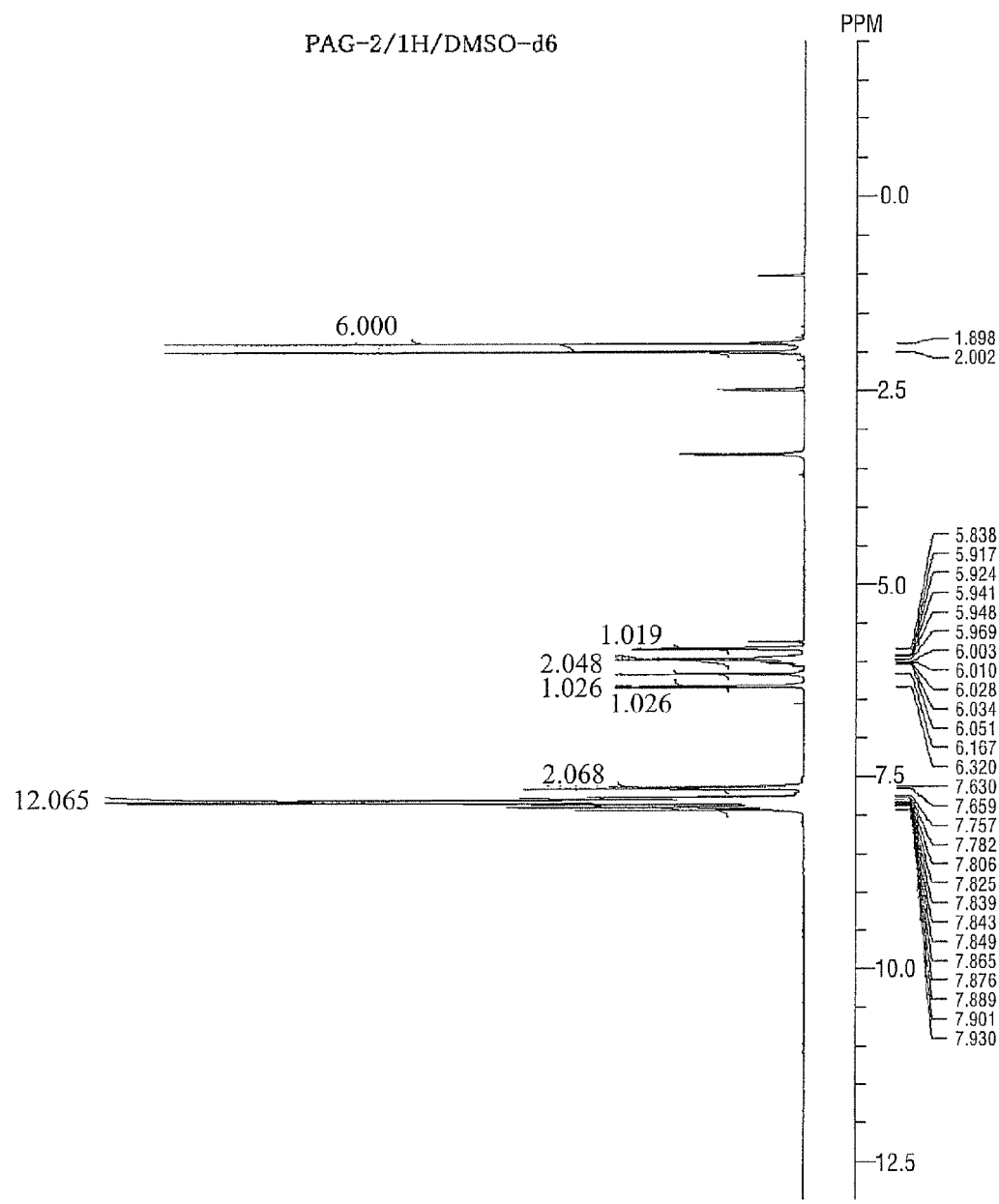
FIG. 3 is a diagram showing the $^1$H-NMR spectrum of PAG-2 in Synthesis Example 1-5.
Figure 4:
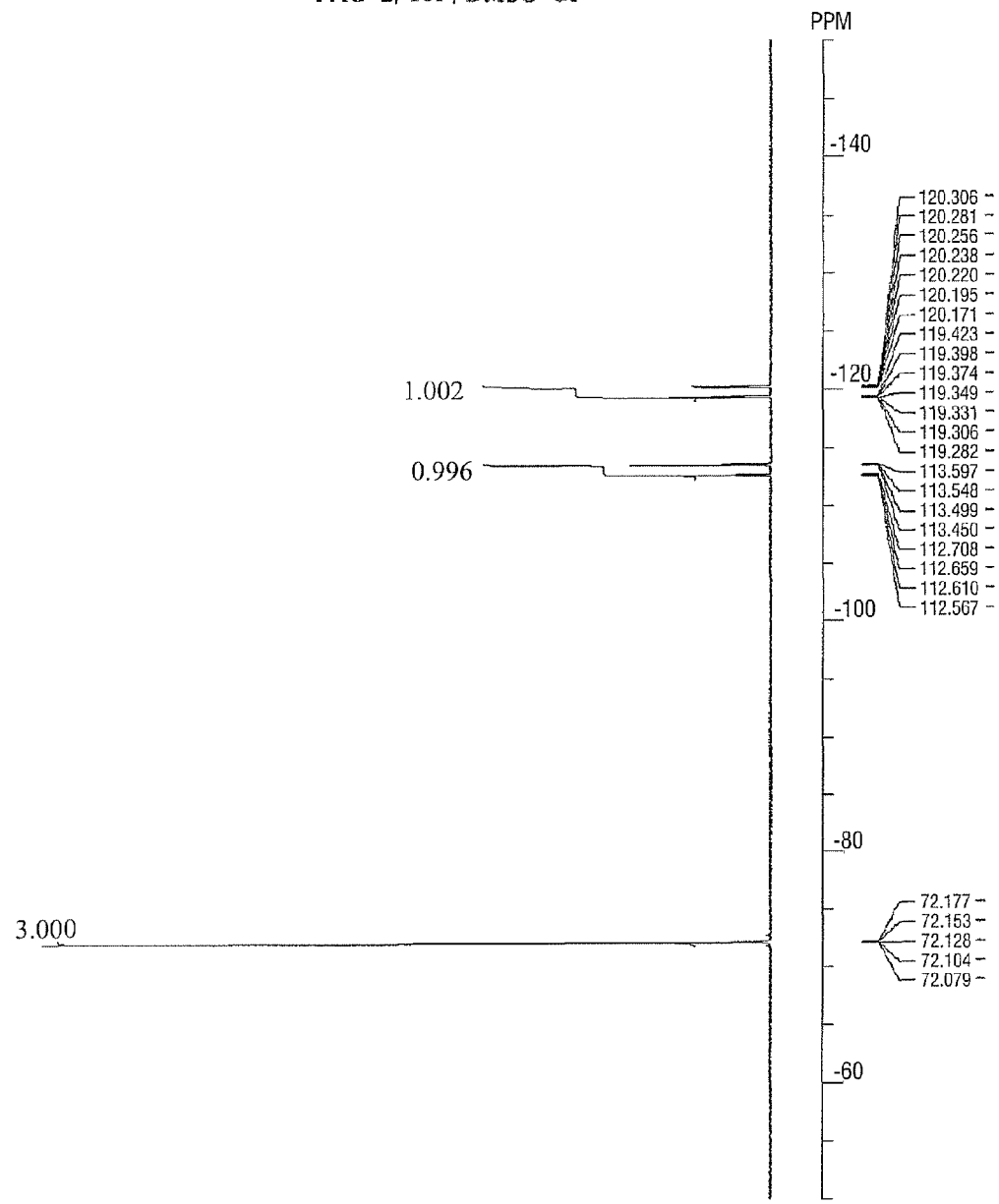
FIG. 4 is a diagram showing the $^{19}$F-NMR spectrum of PAG-2 in Synthesis Example 1-5.

Spectrum data of the intended substance thus obtained are shown below. Results of the nuclear magnetic resonance spectra ($^1$H-NMR, $^{19}$F-NMR/DMSO-$d_6$) are shown in FIG. 3 and FIG. 4, respectively. Meanwhile, trace amounts of residual solvents (diisopropyl ether, dichloromethane and water) are detected in $^1$H-NMR.

IR Spectrum (IR(D-ATR); cm$^{-1}$): 1741, 1637, 1584, 1489, 1477, 1447, 1406, 1376, 1321, 1251, 1215, 1185, 1170, 1116, 1070, 996, 948, 902, 883, 839, 808, 750, 684 and 642 cm$^{-1}$ Time-of-Flight Mass Spectrum Analysis (TOFMS; MALDI): POSITIVE: M$^+$ 347 (corresponding to $C_{22}H_{19}O_2S$) NEGATIVE: M$^-$ 297 (corresponding to $C_7H_6F_5O_5S$)

Synthesis Example PAG-3 to PAG-8

PAG-3 to PAG-8 shown below can be synthesized in a similar manner to that of Synthesis Examples 1-1 to 1-5 except that 2,6-dimethyl-4-hydroxyphenyldiphenylsulfonium 4-methylbenzenesulfonate, bis(4-methylphenyl)(4-hydroxyphenyl)sulfonium 4-methylbenzenesulfonate or bis(4-tert-butylphenyl)(4-hydroxyphenyl)sulfonium 4-methylbenzenesulfonate was used instead of 4-hydroxyphenyldiphenylsulfonium 4-methylbenzenesulfonate.

PAG-3
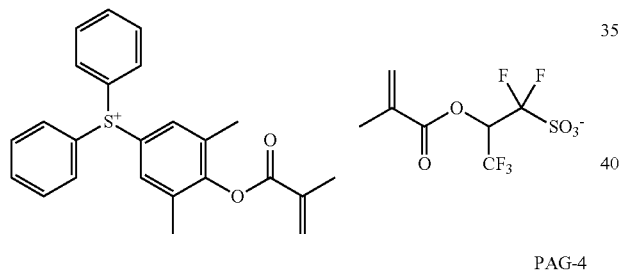

PAG-4
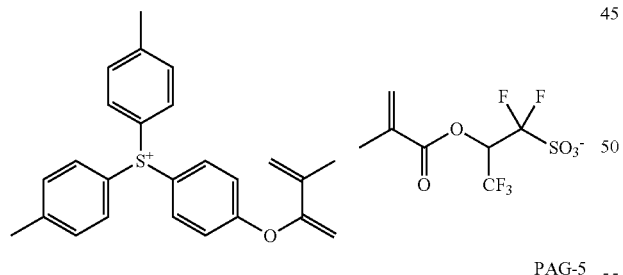

PAG-5
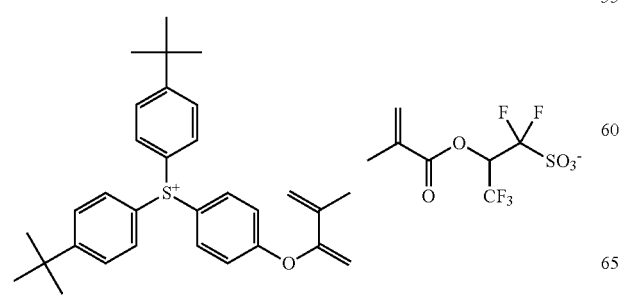

PAG-6
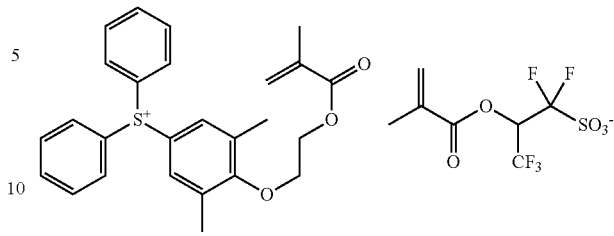

PAG-7
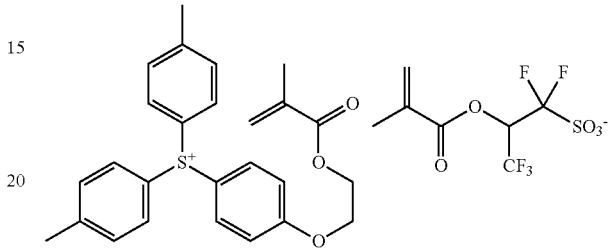

PAG-8
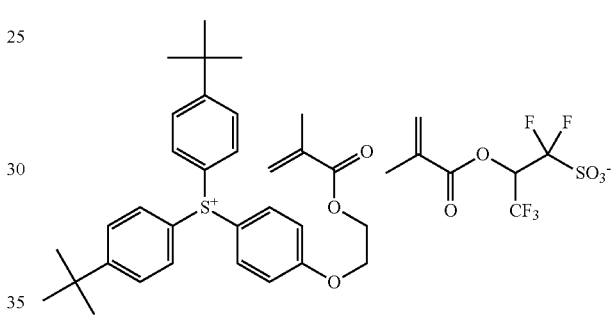

Polymers of the present invention were synthesized according to the following prescriptions.

Synthesis Example 2-1

Synthesis of Polymer 1

Poured into a flask in nitrogen ambient were 4.78 g of 4-(2-methacryloyloxyethoxy)phenyldiphenylsulfonium 1,1,3,3,3-pentafluoro-2-(methacryloyloxy)propane-1-sulfonate (PAG-1), 6.87 g of 6-methyl-spiro[4.5]deca-6-yl methacrylate, 1.37 g of 3-hydroxy-1-adamantyl methacrylate, 4.41 g of 4,8-dioxatricyclo[4.2.1.0$^{3,7}$]nonane-5-one-2-yl methacrylate, 0.67 g of 2-2'-azobis(2-methylpropionate), 0.14 g of 2-mercaptoethanol and 23.9 g of MEK (methyl ethyl ketone), to prepare a monomer solution. Poured into another flask in nitrogen ambient was 8.8 g of MEK, and heated to 80° C. while stirring, followed by dropping of the monomer solution over for 4 hours. After dropping, the polymerization solution was continuously stirred for 2 hours while keeping the temperature thereof at 80° C., and then cooled to a room temperature. The thus obtained polymerization solution was dropped into a mixed solvent of 10 g of MEK and 150 g of hexane, and a separated copolymer was filtered out. The obtained copolymer was washed two times by a mixed solvent of 30.0 g of MEK and 60.0 g of hexane and then vacuum dried at 50° C. for 20 hours, to obtain the polymer represented by the following formula Polymer 1 as a white powder solid. The yield was 12.42 g (yield: 83%).

(Polymer 1)

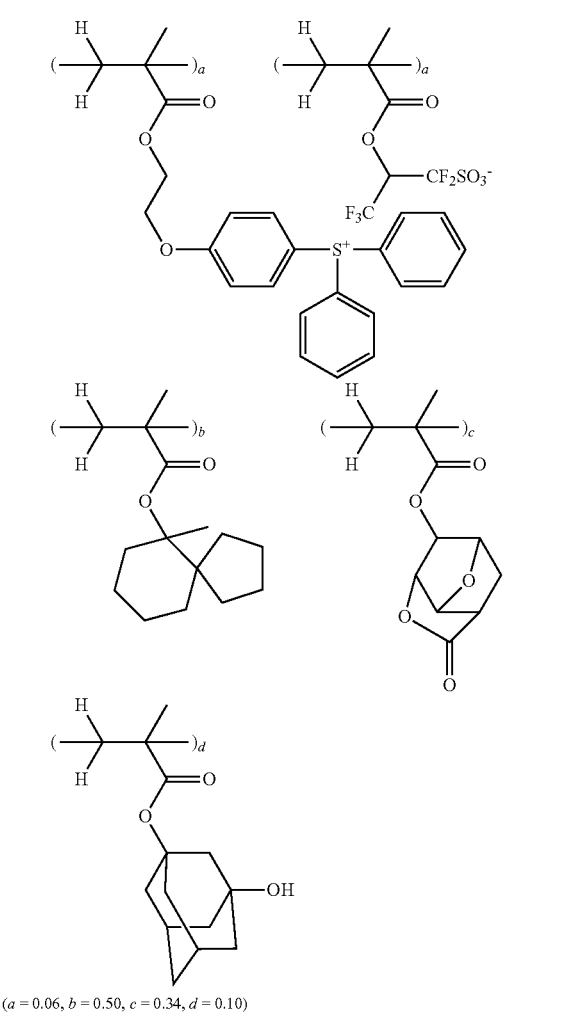

($a = 0.06, b = 0.50, c = 0.34, d = 0.10$)

Synthesis Examples 2-2 to 2-22 and 2-44 to 2-49

Synthesis of Polymers 2 to 22 and 44 to 49

Polymers shown by Tables 1 and 2 were synthesized in a similar manner to that of Synthesis Example 2-1 except that each monomer and their blending ratios were changed.

Synthesis Example 2-23

Synthesis of Polymer 23

Poured into a flask in nitrogen ambient were 2.70 g of 4-(2-methacryloyloxyethoxy)phenyldiphenylsulfonium 1,1,3,3,3-pentafluoro-2-(methacryloyloxy)propane-1-sulfonate, 12.0 g of 4-amyloxystyrene, 12.5 g of 4-hydroxyphenyl methacrylate, 2.80 g of acenaphthylene, 2.90 g of 2-2'-azobis (2-methylpropionate), and 30.0 g of MEK (methyl ethyl ketone), to prepare a monomer solution. Poured into another flask in nitrogen ambient was 40 g of MEK, and heated to 80° C. while stirring, followed by dropping of the monomer solution over for 4 hours. After dropping, the polymerization solution was continuously stirred for 16 hours while keeping the temperature thereof at 80° C., and then cooled to a room temperature. The thus obtained polymerization solution was dropped into a mixed solvent of 250 g of toluene and 500 g of hexane, and a separated copolymer was filtered out. The copolymer filtered out was washed two times by 100 g of hexane and then vacuum dried at 40° C. for 20 hours, to obtain the polymer represented by the following formula Polymer 23 as a white powder solid. The yield was 28.5 g (yield: 95%).

(Polymer 23)

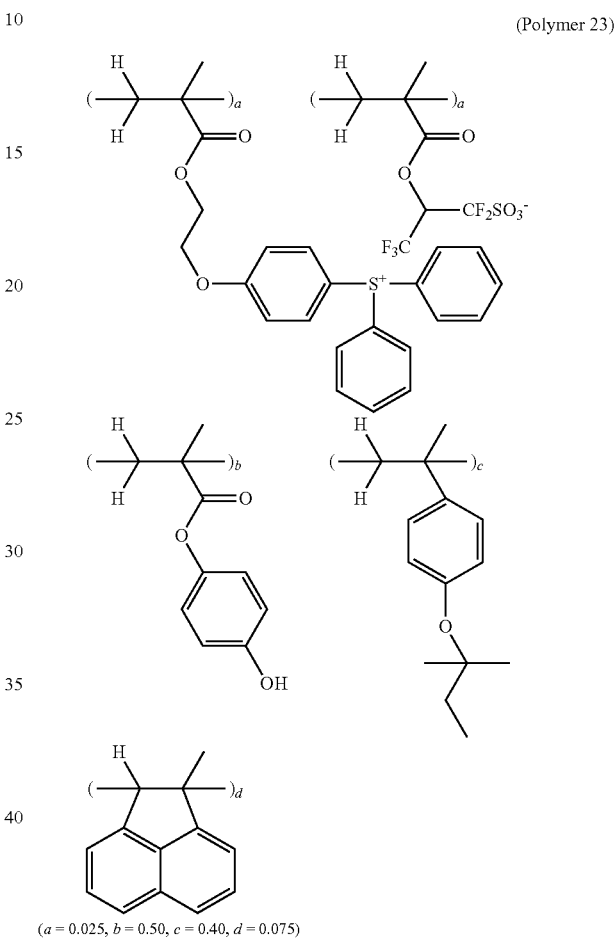

($a = 0.025, b = 0.50, c = 0.40, d = 0.075$)

Synthesis Examples 2-24 to 2-34 and 2-50

Synthesis of Polymers 24 to 34 and 50

Polymers shown by Tables 1 and 2 were produced in a similar manner to that of Synthesis Example 2-23 except that each monomer and their blending ratios were changed.

Synthesis Examples 2-35 to 2-41 and 2-51

Synthesis of Polymers 35 to 41 and 51

Each Polymers 27 to 34 obtained by the above-mentioned prescription was dissolved in a mixed solvent of methanol and tetrahydrofuran, and oxalic acid was added thereto to perform a deprotection reaction at 40° C. Usual reprecipitation purification was performed after a neutralization treatment with pyridine to obtain Polymers 35 to 41 and 51 having a hydroxystyrene unit.

Synthesis Examples 2-42, 2-43 and 2-52

Synthesis of Polymers 42, 43 and 52

Polymer 40 was reacted with 1-chloro-1-methoxy-2-methylpropane under a basic condition to obtain the intended polymer 42. Polymers 41 and 35 are reacted with 8-(1-chloro-2-methylpropyloxy)-tricyclo[5.2.1.0$^{2,6}$]decane under a basic condition to obtain the intended polymers 43 and 52 respectively.

Deprotection and protection of polyhydroxystyrene derivatives in Synthesis Examples 2-27 to 2-43, 2-51 and 2-52 are elaborated in Japanese Patent Laid-Open (kokai) No. 2004-115630, Japanese Patent Laid-Open (kokai) No. 2005-8766 and the like.

The synthesized polymers are shown in Tables 1 and 2, and structures of each unit are shown in Tables 3 to 7. Here, the introduction ratio in Tables 1 and 2 is shown by mole ratio.

TABLE 1

| Synthesis Example No. | Resin | Unit 1 (introduction ratio) | Unit 2 (introduction ratio) | Unit 3 (introduction ratio) | Unit 4 (introduction ratio) | Unit 5 (introduction ratio) |
| --- | --- | --- | --- | --- | --- | --- |
| 2-1 | Polymer 1 | PAG-1 (0.06) | A-1M (0.50) | B-2M (0.34) | B-1M (0.10) | — |
| 2-2 | Polymer 2 | PAG-1 (0.05) | A-1M (0.50) | B-3M (0.35) | B-1M (0.10) | — |
| 2-3 | Polymer 3 | PAG-1 (0.05) | A-1M (0.50) | B-4M (0.35) | B-1M (0.10) | — |
| 2-4 | Polymer 4 | PAG-1 (0.05) | A-1M (0.45) | B-4M (0.30) | B-1M (0.10) | B-5M (0.10) |
| 2-5 | Polymer 5 | PAG-1 (0.05) | A-2M (0.50) | B-2M (0.35) | B-1M (0.10) | — |
| 2-6 | Polymer 6 | PAG-1 (0.05) | A-2M (0.50) | B-3M (0.35) | B-1M (0.10) | — |
| 2-7 | Polymer 7 | PAG-1 (0.05) | A-2M (0.50) | B-4M (0.35) | B-1M (0.10) | — |
| 2-8 | Polymer 8 | PAG-1 (0.05) | A-2M (0.45) | B-4M (0.30) | B-1M (0.10) | B-5M (0.10) |
| 2-9 | Polymer 9 | PAG-1 (0.05) | A-2M (0.50) | B-2M (0.35) | B-7M (0.10) | — |
| 2-10 | Polymer 10 | PAG-1 (0.05) | A-2M (0.40) | B-2M (0.35) | B-1M (0.10) | C-1M (0.10) |
| 2-11 | Polymer 11 | PAG-1 (0.05) | A-3M (0.50) | B-2M (0.35) | B-1M (0.10) | — |
| 2-12 | Polymer 12 | PAG-1 (0.05) | A-2M (0.35) | B-2M (0.35) | B-1M (0.10) | A-3M (0.15) |
| 2-13 | Polymer 13 | PAG-1 (0.05) | A-3M (0.40) | B-2M (0.35) | B-1M (0.10) | C-2M (0.10) |
| 2-14 | Polymer 14 | PAG-2 (0.05) | A-1M (0.50) | B-2M (0.35) | B-1M (0.10) | — |
| 2-15 | Polymer 15 | PAG-2 (0.05) | A-2M (0.50) | B-2M (0.35) | B-1M (0.10) | — |
| 2-16 | Polymer 16 | P-1M (0.02) | P-2M (0.02) | A-2M (0.50) | B-2M (0.36) | B-1M (0.10) |
| 2-17 | Polymer 17 | PAG-1 (0.05) | A-2M (0.40) | B-2M (0.35) | B-6M (0.20) | — |
| 2-18 | Polymer 18 | PAG-1 (0.05) | A-2M (0.40) | B-4M (0.35) | B-6M (0.20) | — |
| 2-19 | Polymer 19 | PAG-2 (0.05) | A-2M (0.40) | B-2M (0.35) | B-6M (0.20) | — |
| 2-20 | Polymer 20 | PAG-2 (0.05) | A-2M (0.40) | B-4M (0.35) | B-6M (0.20) | — |
| 2-21 | Polymer 21 | PAG-1 (0.02) | A-2M (0.50) | B-2M (0.38) | B-1M (0.10) | — |
| 2-22 | Polymer 22 | PAG-2 (0.02) | A-2M (0.50) | B-2M (0.38) | B-1M (0.10) | — |
| 2-23 | Polymer 23 | PAG-1 (0.025) | B-6M (0.50) | D-3M (0.40) | D-5M (0.075) | — |
| 2-24 | Polymer 24 | PAG-2 (0.025) | B-6M (0.50) | D-3M (0.40) | D-5M (0.075) | — |
| 2-25 | Polymer 25 | PAG-1 (0.01) | B-6M (0.50) | D-3M (0.40) | D-5M (0.09) | — |
| 2-26 | Polymer 26 | PAG-2 (0.01) | B-6M (0.50) | D-3M (0.40) | D-5M (0.09) | — |
| 2-27 | Polymer 27 | D-2M (0.50) | D-3M (0.40) | D-5M (0.10) | — | — |
| 2-28 | Polymer 28 | D-2M (0.90) | D-5M (0.10) | — | — | — |
| 2-29 | Polymer 29 | PAG-1 (0.025) | D-2M (0.50) | D-3M (0.40) | D-4M (0.075) | — |
| 2-30 | Polymer 30 | PAG-1 (0.025) | D-2M (0.50) | D-3M (0.40) | D-5M (0.075) | — |
| 2-31 | Polymer 31 | PAG-1 (0.01) | D-2M (0.50) | D-3M (0.40) | D-5M (0.09) | — |
| 2-32 | Polymer 32 | PAG-2 (0.01) | D-2M (0.50) | D-3M (0.40) | D-5M (0.09) | — |
| 2-33 | Polymer 33 | PAG-1 (0.025) | D-2M (0.90) | D-4M (0.075) | — | — |
| 2-34 | Polymer 34 | PAG-1 (0.025) | D-1M (0.90) | D-5M (0.075) | — | — |
| 2-35 | Polymer 35 | D-1M (0.90) | D-5M (0.10) | — | — | — |
| 2-36 | Polymer 36 | PAG-1 (0.025) | D-1M (0.50) | D-3M (0.40) | D-4M (0.075) | — |
| 2-37 | Polymer 37 | PAG-1 (0.025) | D-1M (0.50) | D-3M (0.40) | D-5M (0.075) | — |
| 2-38 | Polymer 38 | PAG-1 (0.01) | D-1M (0.50) | D-3M (0.40) | D-5M (0.09) | — |
| 2-39 | Polymer 39 | PAG-2 (0.01) | D-1M (0.50) | D-3M (0.40) | D-5M (0.09) | — |
| 2-40 | Polymer 40 | PAG-1 (0.025) | D-1M (0.90) | D-4M (0.075) | — | — |
| 2-41 | Polymer 41 | PAG-1 (0.025) | D-1M (0.90) | D-5M (0.075) | — | — |
| 2-42 | Polymer 42 | PAG-1 (0.025) | D-1M (0.70) | D-6M (0.20) | D-4M (0.075) | — |
| 2-43 | Polymer 43 | PAG-1 (0.025) | D-1M (0.70) | D-7M (0.20) | D-5M (0.075) | — |

TABLE 2

| Synthesis Example No. | Resin | Unit 1 (introduction ratio) | Unit 2 (introduction ratio) | Unit 3 (introduction ratio) | Unit 4 (introduction ratio) | Unit 5 (introduction ratio) |
| --- | --- | --- | --- | --- | --- | --- |
| 2-44 | Polymer 44 | A-1M (0.55) | B-1M (0.10) | B-2M (0.35) | — | — |
| 2-45 | Polymer 45 | A-2M (0.55) | B-1M (0.10) | B-2M (0.35) | — | — |
| 2-46 | Polymer 46 | P-1M (0.05) | A-2M (0.50) | B-2M (0.35) | B-1M (0.10) | — |
| 2-47 | Polymer 47 | P-2M (0.05) | A-2M (0.50) | B-2M (0.35) | B-1M (0.10) | — |
| 2-48 | Polymer 48 | A-2M (0.45) | B-2M (0.35) | B-6M (0.20) | — | — |
| 2-49 | Polymer 49 | A-2M (0.45) | B-2M (0.35) | B-6M (0.20) | — | — |
| 2-50 | Polymer 50 | B-6M (0.50) | D-3M (0.40) | D-5M (0.07) | P-1M (0.03) | — |

TABLE 2-continued
| Synthesis Example No. | Resin | Unit 1 (introduction ratio) | Unit 2 (introduction ratio) | Unit 3 (introduction ratio) | Unit 4 (introduction ratio) | Unit 5 (introduction ratio) |
|---|---|---|---|---|---|---|
| 2-51 | Polymer 51 | D-1M (0.50) | D-3M (0.40) | D-5M (0.10) | — | — |
| 2-52 | Polymer 52 | D-1M (0.70) | D-7M (0.20) | D-5M (0.10) | — | — |
TABLE 3
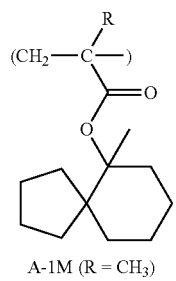
A-1M (R = CH₃)
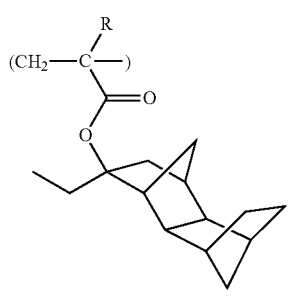
A-2M (R = CH₃)
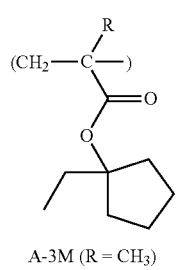
A-3M (R = CH₃)
TABLE 4
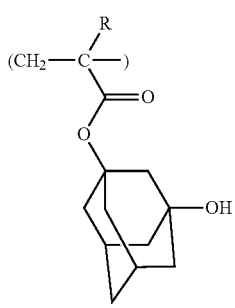
B-1M (R = CH₃)
TABLE 4-continued
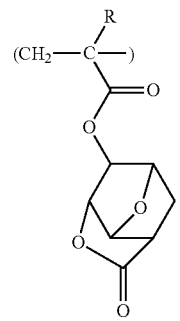
B-2M (R = CH₃)
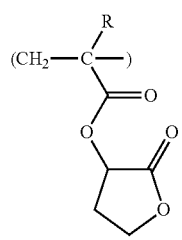
B-3M (R = CH₃)
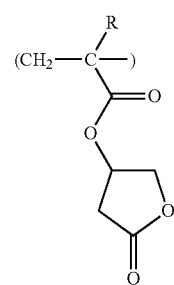
B-4M (R = CH₃)
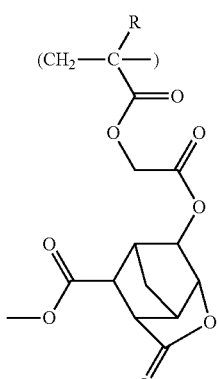
B-5M (R = CH₃)

TABLE 4-continued
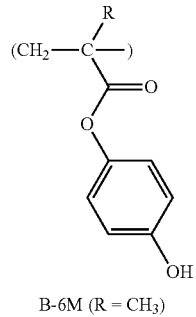
B-6M (R = CH₃)
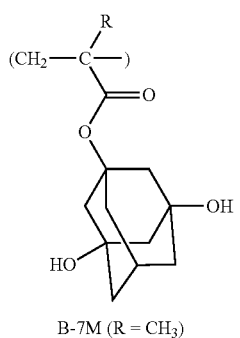
B-7M (R = CH₃)
TABLE 5
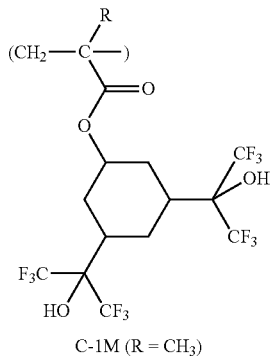
C-1M (R = CH₃)
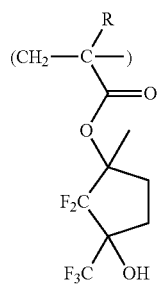
C-2M (R = CH₃)
TABLE 6
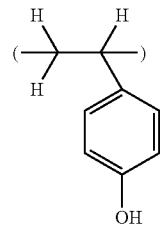
D-1M
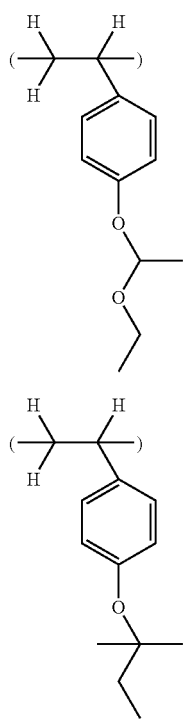
D-2M
D-3M
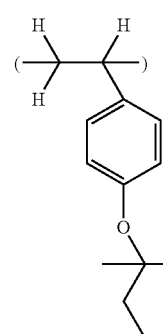
D-4M
D-5M
D-6M

TABLE 6-continued

D-7M

TABLE 7

P-1M

P-2M

Examples 1-1 to 1-24 and Comparative Examples 1-1 to 1-9

Preparation of Resist Compositions

Polymers 1 to 3, 5, 8, 9, 14 to 26, 37 to 39, 43, 46 and 47 (for following Examples) and Polymers 44 to 52 (for following Comparative Examples) produced as described above were each used as the base resin, and an acid generator, a quencher (a base) and a solvent were added according to the composition shown in Table 8. After they were mixed and dissolved, the solution was filtrated by a filter (pore diameter of 0.2 pm) made of Teflon (registered trade mark) to obtain each resist composition (R-01 to R-24 for Examples, and R-25 to R-33 for Comparative Examples). Here, the solvent containing 0.01% by mass of the surfactant manufactured by Omnova Inc. (surfactant-1), which will be mentioned later, was used in all of the compositions.

TABLE 8

|  | Resist | Resin (parts by mass) | Acid generator (parts by mass) | Base (parts by mass) | Solvent 1 (parts by mass) | Solvent 2 (parts by mass) | Solvent 3 (parts by mass) |
| --- | --- | --- | --- | --- | --- | --- | --- |
| Ex. 1-1 | R-01 | Polymer 1 (80) | — | Base-1 (1.18) | PGMEA (896) | CyHO (364) | — |
| Ex. 1-2 | R-02 | Polymer 2 (80) | — | Base-1 (1.18) | PGMEA (896) | CyHO (364) | — |
| Ex. 1-3 | R-03 | Polymer 3 (80) | — | Base-1 (1.18) | PGMEA (896) | CyHO (364) | — |
| Ex. 1-4 | R-04 | Polymer 5 (80) | — | Base-1 (1.18) | PGMEA (896) | CyHO (364) | — |
| Ex. 1-5 | R-05 | Polymer 8 (80) | — | Base-1 (1.18) | PGMEA (896) | CyHO (364) | — |
| Ex. 1-6 | R-06 | Polymer 9 (80) | — | Base-1 (1.18) | PGMEA (896) | CyHO (364) | — |
| Ex. 1-7 | R-07 | Polymer 46 (40) Polymer 47 (40) | — | Base-1 (1.18) | PGMEA (896) | CyHO (364) | — |
| Ex. 1-8 | R-08 | Polymer 16 (80) | — | Base-1 (1.18) | PGMEA (896) | CyHO (364) | — |
| Ex. 1-9 | R-09 | Polymer 14 (80) | — | Base-1 (1.18) | PGMEA (896) | CyHO (364) | — |
| Ex. 1-10 | R-10 | Polymer 15 (80) | — | Base-1 (1.18) | PGMEA (896) | CyHO (364) | — |
| Ex. 1-11 | R-11 | Polymer 17 (80) | — | Base-1 (1.18) | PGMEA (896) | CyHO (364) | — |
| Ex. 1-12 | R-12 | Polymer 18 (80) | — | Base-1 (1.18) | PGMEA (896) | CyHO (364) | — |
| Ex. 1-13 | R-13 | Polymer 19 (80) | — | Base-1 (1.18) | PGMEA (896) | CyHO (364) | — |
| Ex. 1-14 | R-14 | Polymer 20 (80) | — | Base-1 (1.18) | PGMEA (896) | CyHO (364) | — |
| Ex. 1-15 | R-15 | Polymer 21 (80) | PAG-A (5.1) | Base-1 (1.18) | PGMEA (896) | CyHO (364) | — |
| Ex. 1-16 | R-16 | Polymer 22 (80) | PAG-A (5.1) | Base-1 (1.18) | PGMEA (896) | CyHO (364) | — |
| Ex. 1-17 | R-17 | Polymer 23 (80) | — | Base-2 (0.2) | PGMEA (1000) | EL (1000) | PGME (1300) |
| Ex. 1-18 | R-18 | Polymer 24 (80) | — | Base-2 (0.2) | PGMEA (1000) | EL (1000) | PGME (1300) |
| Ex. 1-19 | R-19 | Polymer 25 (80) | PAG-B (3.2) | Base-2 (0.2) | PGMEA (1000) | EL (1000) | PGME (1300) |
| Ex. 1-20 | R-20 | Polymer 26 (80) | PAG-B (3.2) | Base-2 (0.2) | PGMEA (1000) | EL (1000) | PGME (1300) |

TABLE 8-continued

| | Resist | Resin (parts by mass) | Acid generator (parts by mass) | Base (parts by mass) | Solvent 1 (parts by mass) | Solvent 2 (parts by mass) | Solvent 3 (parts by mass) |
|---|---|---|---|---|---|---|---|
| Ex. 1-21 | R-21 | Polymer 37 (80) | — | Base-2 (0.2) | PGMEA (1000) | EL (1000) | PGME (1300) |
| Ex. 1-22 | R-22 | Polymer 38 (80) | PAG-B (3.2) | Base-2 (0.2) | PGMEA (1000) | EL (1000) | PGME (1300) |
| Ex. 1-23 | R-23 | Polymer 39 (80) | PAG-B (3.2) | Base-2 (0.2) | PGMEA (1000) | EL (1000) | PGME (1300) |
| Ex. 1-24 | R-24 | Polymer 43 (80) | — | Base-2 (0.2) | PGMEA (1000) | EL (1000) | PGME (1300) |
| Com. Ex. 1-1 | R-25 | Polymer 44 (80) | PAG-A (12.7) | Base-1 (1.18) | PGMEA (896) | CyHO (364) | — |
| Com. Ex. 1-2 | R-26 | Polymer 45 (80) | PAG-A (12.7) | Base-1 (1.10) | PGMEA (896) | CyHO (364) | — |
| Com. Ex. 1-3 | R-27 | Polymer 46 (80) | — | Base-1 (1.18) | PGMEA (896) | CyHO (364) | — |
| Com. Ex. 1-4 | R-28 | Polymer 47 (80) | — | Base-1 (1.18) | PGMEA (896) | CyHO (364) | — |
| Com. Ex. 1-5 | R-29 | Polymer 48 (80) | PAG-A (12.7) | Base-1 (1.18) | PGMEA (896) | CyHO (364) | — |
| Com. Ex. 1-6 | R-30 | Polymer 49 (80) | PAG-A (12.7) | Base-1 (1.18) | PGMEA (896) | CyHO (364) | — |
| Com. Ex. 1-7 | R-31 | Polymer 50 (80) | PAG-B (8.0) | Base-2 (0.2) | PGMEA (1000) | EL (1000) | PGME (1300) |
| Com. Ex. 1-8 | R-32 | Polymer 51 (80) | PAG-B (8.0) | Base-2 (0.2) | PGMEA (1000) | EL (1000) | PGME (1300) |
| Com. Ex. 1-9 | R-33 | Polymer 52 (80) | PAG-B (8.0) | Base-2 (0.2) | PGMEA (1000) | EL (1000) | PGME (1300) |

In Table 8, acid generators, quenchers (bases), and solvents represent as follows respectively.

PAG-A: triphenylsulfonium 2-(adamantane-1-carbonyloxy)-1,1,3,3,3-pentafluoropropane-1-sulfonate (a compound described in a Japanese Patent Laid-Open (kokai) No 2007-145797)
PAG-B: triphenylsulfonium 2,4,6-triisopropylbenzenesulfonate
Base-1: lauric acid 2-morpholinoethyl
Base-2: tris(2-methoxymethoxyethyl)amine N-oxide
PGMEA: propylene glycol monomethyl ether acetate
CyHO: cyclohexanone
EL: ethyl lactate
PGME: propylene glycol monomethyl ether
Surfactant-1: 3-methyl-3-(2,2,2-trifluoroethoxymethyl)oxetane tetrahydrofuran 2,2-dimethyl-1,3-propanediol copolymer (manufactured by Omnova Inc.)

Examples 2-1 to 2-12, and Comparative Examples 2-1 to 2-4

Evaluation of Resolution, Exposure Margin, and Line Edge Roughness (LER): ArF Exposure A solution for an anti-reflection film (ARC-29A, manufactured by Nissan Chemical Industries, Ltd.) was applied on a silicon substrate and baked at 200° C. for 60 seconds to prepare an anti-reflection film (film thickness of 78 nm). On it, resist compositions of the present invention (R-1 to R-10, R-15 and R-16) and resist compositions for Comparative Examples (R-25 and R-28) were each applied by spin coating and baked on a hot plate for 60 seconds to prepare a resist film with the film thickness of 100 nm. This was exposed by using an ArF excimer laser scanner (NSR-S307E, NA-0.85, 4/5 annular illumination, and 6% half tone phase shift mask, manufactured by Nikon, Corp.), baked at 100° C. for 60 seconds (PEB: post exposure bake), and then developed by an aqueous tetramethyl ammonium hydroxide solution (2.38% by mass) for 60 seconds.

The resists were evaluated as follows: the exposure dose to resolve the line-and-space of the 80 nm group at 1:1 was taken as the optimum exposure dose (Eop, mJ/cm$^2$), and the minimum line width (nm) of the line-and-space separated at this exposure dose was taken as the resolution of the evaluated resist. The exposure margin was evaluated as follows: the exposure dose range to allow the pattern size change within 80 nm±10% with the change of the optimum exposure dose was obtained, and this value was divided by the optimum exposure dose and then expressed by the percentage. When the percentage value is larger, the performance change due to the exposure dose change is smaller and the exposure margin is better. The line edge roughness (LER) of the line-and-space with 80 nm was measured by the length measuring SEM (S-9380, manufactured by Hitachi High-Technologies Corp.). The results are shown in Table 9.

TABLE 9

| | Resist | Optimum Exposure Dose (mJ/cm$^2$) | Resolution Limit (nm) | Exposure Margin (%) | LER (nm) |
|---|---|---|---|---|---|
| Ex. 2-1 | R-01 | 30 | 70 | 14.2 | 5.0 |
| Ex. 2-2 | R-02 | 32 | 70 | 13.5 | 4.5 |
| Ex. 2-3 | R-03 | 30 | 75 | 14.2 | 5.3 |
| Ex. 2-4 | R-04 | 34 | 75 | 13.7 | 5.3 |
| Ex. 2-5 | R-05 | 33 | 70 | 13.6 | 5.0 |
| Ex. 2-6 | R-06 | 33 | 75 | 14.0 | 4.7 |
| Ex. 2-7 | R-07 | 35 | 70 | 14.5 | 4.6 |
| Ex. 2-8 | R-08 | 31 | 75 | 13.6 | 5.1 |
| Ex. 2-9 | R-09 | 33 | 70 | 13.7 | 4.3 |
| Ex. 2-10 | R-10 | 31 | 75 | 14.2 | 5.5 |
| Ex. 2-11 | R-15 | 32 | 75 | 13.5 | 4.5 |
| Ex. 2-12 | R-16 | 30 | 75 | 14.2 | 5.0 |
| Com. Ex. 2-1 | R-25 | 30 | 80 | 12.5 | 7.2 |
| Com. Ex. 2-2 | R-26 | 37 | 80 | 11.8 | 7.8 |
| Com. Ex. 2-3 | R-27 | 37 | 80 | 12.6 | 6.2 |
| Com. Ex. 2-4 | R-28 | 40 | 80 | 12.8 | 7.0 |

From the results of Examples in Table 9, it was confirmed that in the ArF excimer laser exposure, the resist composition of the present invention is not only excellent in resolution, but also has small line edge roughness and is excellent in exposure margin.

Examples 3-1 to 3-8, and Comparative Examples 3-1 to 3-3

Evaluation of Resolution and Line Edge Roughness (LER): EB Lithography

Resist compositions of the present invention (R-17 to R-24) and resist compositions for comparison (R-31 to R-33) were each applied onto a mask blank of 152 mm square having an outermost surface made of a chromium oxynitride film by a spin coating method by ACT-M (manufactured by Tokyo Electron Ltd.) and prebaked on a hot plate at 110° C. for 600 seconds to obtain a resist film with a thickness of 60 nm. The measurement of a thickness of each obtained resist film was conducted by an optical measurement device Nano-Spec (manufactured by Nanometrics Inc.). The measurement was conducted at 81 in-plane points of the blank substrate except for the outer peripheral region within 10 mm from the outer edge to the inner extent, so as to calculate the average film thickness and the film thickness range.

Then, the exposure was made with an electron beam exposure instrument EBM 5000 plus (manufactured by NuFlare Technology, Inc., acceleration voltage of 50 keV), which was followed by the bake (PEB: post exposure bake) at 110° C. for 600 seconds and then development in a 2.38% aqueous solution of tetramethyl ammonium hydroxide to obtain a positive pattern. The resist patterns thus obtained were evaluated as follows.

The prepared wafer with a pattern was observed under SEM (a scanning electron microscope). The exposure dose at which 200 nm line-and-space was resolved at 1:1 was taken as the optimum exposure dose ($\mu C/cm^2$), and the minimum size at this exposure dose was taken as the resolution. In addition, edge roughness (LER) of 100 nm LS was measured by SEM. As for pattern profile, whether it is rectangular or not was evaluated by visual observation. The evaluation results of the resist compositions of the present invention and the resist compositions for comparison in the EB lithography are shown in Table 10.

TABLE 10

| | Resist | Optimum Exposure Dose ($\mu C/cm^2$) | Limit Resolution (nm) | LER (nm) | Pattern Profile |
|---|---|---|---|---|---|
| Ex. 3-1 | R-17 | 24 | 35 | 4.5 | Rectangular |
| Ex. 3-2 | R-18 | 25 | 35 | 4.6 | Rectangular |
| Ex. 3-3 | R-19 | 29 | 40 | 4.3 | Rectangular |
| Ex. 3-4 | R-20 | 28 | 40 | 4.7 | Rectangular |
| Ex. 3-5 | R-21 | 26 | 35 | 3.9 | Rectangular |
| Ex. 3-6 | R-22 | 27 | 35 | 4.0 | Rectangular |
| Ex. 3-7 | R-23 | 24 | 40 | 4.2 | Rectangular |
| Ex. 3-8 | R-24 | 22 | 40 | 4.1 | Rectangular |
| Com. Ex. 3-1 | R-31 | 26 | 60 | 6.2 | rounding + footing |
| Com. Ex. 3-2 | R-32 | 27 | 60 | 6.2 | rounding + footing |
| Com. Ex. 3-3 | R-33 | 26 | 60 | 6.0 | rounding + footing |

From the results in Table 10, it was confirmed that in the EB lithography, the resist composition of the present invention is excellent in resolution and LER.

Examples 4-1 to 4-4 and Comparative Examples 4-1 and 4-2

Evaluation of Sensitivity and Resolution: EUV exposure

Resist compositions of the present invention (R-11 to R-14) and resist compositions for comparison (R-29 and R-30) were each applied on a silicon wafer treated with hexamethyldisilazane (HMDS) by a spin coating method and heat treated at 110° C. for 60 seconds to form a resist film with a thickness of 50 nm. Each obtained resist film was exposed by using the EUV micro stepper (NA=0.3, monopole illumination), heat treated (PEB: post exposure bake) at 95° C. for 60 seconds, and developed for 30 seconds in 2.38% aqueous solution of tetramethylammonium hydroxide, to obtain a positive pattern.

The obtained resist pattern was evaluated as follows.

The exposure dose to resolve a top and a bottom of the 32 nm line-and-space at 1:1 was taken as the optimum exposure dose (sensitivity: Eop), and the minimum line width of the line-and-space separated at this exposure dose was taken as the resolution of the evaluated resist. The results are shown in Table 11.

TABLE 11

| | Resist | Eop ($mJ/cm^2$) | Resolution (nm) |
|---|---|---|---|
| Ex. 4-1 | R-11 | 17 | 26 |
| Ex. 4-2 | R-12 | 17 | 25 |
| Ex. 4-3 | R-13 | 18 | 25 |
| Ex. 4-4 | R-14 | 18 | 26 |
| Com. Ex. 4-1 | R-29 | 26 | 38 |
| Com. Ex. 4-2 | R-30 | 24 | 36 |

From the results in Table 11, it was confirmed that also in the EUV exposure, the resist composition of the present invention has high sensitivity and is excellent in resolution performance.

The present invention is not limited to the above embodiments. The above embodiments are merely illustrative, and whatever having the substantially same configurations as the technical concept recited in the claims of the present application and exhibiting the same functions and effects are embraced within the technical scope of the present invention.

What is claimed is:

1. A sulfonium salt represented by the following general formula (2),

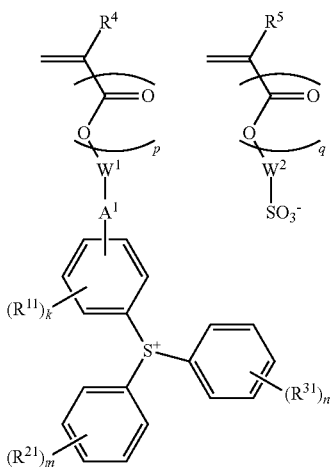

(2)

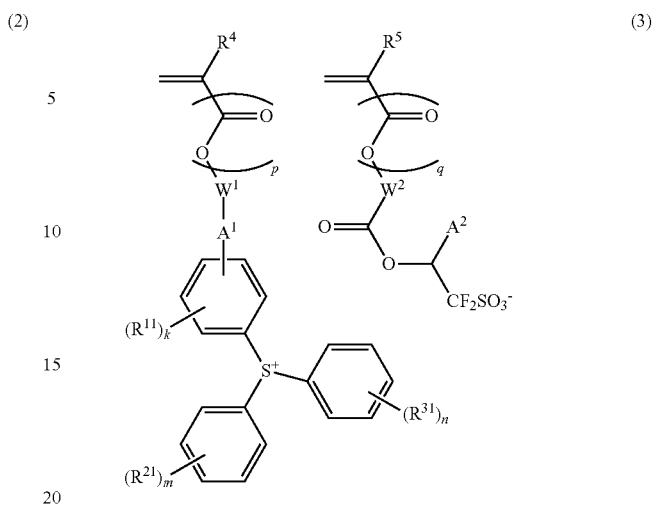

(3)

wherein, $W^1$ represents a single bond or a divalent hydrocarbon group having 1 to 30 carbon atoms optionally containing a hetero atom; $W^2$ represents a single bond or a divalent hydrocarbon group having 1 to 33 carbon atoms optionally containing a hetero atom; $A^1$ represents a single bond, an ether bond or an ester bond; each $R^{11}$, $R^{21}$ and $R^{31}$ independently represents a linear, a branched, or a cyclic alkyl group or alkoxy group having 1 to 10 carbon atoms; $R^{21}$ and $R^{31}$ may be bonded with each other to form a ring together with a sulfur atom in the formula; each $R^4$ and $R^5$ independently represents a hydrogen atom, a fluorine atom, a methyl group or a trifluoromethyl group; k represents 0 to 4; each m and n independently represents 0 to 5; and each p and q independently represents 0 or 1.

2. The sulfonium salt according to claim 1, wherein the sulfonium salt is represented by the following general formula (3), wherein, each $W^1$ and $W^{21}$ independently represents a single bond or a divalent hydrocarbon group having 1 to 30 carbon atoms optionally containing a hetero atom; $A^1$ represents a single bond, an ether bond or an ester bond; $A^2$ represents a hydrogen atom or a trifluoromethyl group; each $R^{11}$, $R^{21}$ and $R^{31}$ independently represents a linear, a branched, or a cyclic alkyl group or alkoxy group having 1 to 10 carbon atoms; $R^{21}$ and $R^{31}$ may be bonded with each other to form a ring together with a sulfur atom in the formula; each $R^4$ and $R^5$ independently represents a hydrogen atom, a fluorine atom, a methyl group or a trifluoromethyl group; k represents 0 to 4; each m and n independently represents 0 to 5; and each p and q independently represents 0 or 1.

* * * * *